US007605154B2

(12) United States Patent
Binnun et al.

(10) Patent No.: US 7,605,154 B2
(45) Date of Patent: Oct. 20, 2009

(54) SUBSTITUTED THIAZOLO [4,5-D]PYRIMIDINES AS PROTEIN KINASE INHIBITORS

(75) Inventors: Eva Binnun, Somerville, MA (US); Peter J. Connolly, New Providence, NJ (US); Sigmond G. Johnson, Flemington, NJ (US); Ronghui Lin, East Brunswick, NJ (US); Steven A. Middleton, Flemington, NJ (US); Sandra J. Moreno-Mazza, Colonia, NJ (US); Niranjan B. Pandey, Flemington, NJ (US); Steven K. Wetter, Flemington, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 234 days.

(21) Appl. No.: 11/498,221

(22) Filed: Aug. 2, 2006

(65) Prior Publication Data

US 2007/0185139 A1 Aug. 9, 2007

Related U.S. Application Data

(60) Provisional application No. 60/706,840, filed on Aug. 8, 2005.

(51) Int. Cl.

| | |
|---|---|
| ***C07D 401/10*** | (2006.01) |
| ***C07D 417/10*** | (2006.01) |
| ***C07D 413/10*** | (2006.01) |
| ***A61K 31/55*** | (2006.01) |
| ***A61K 31/541*** | (2006.01) |
| ***A61K 31/5355*** | (2006.01) |
| ***A61K 31/497*** | (2006.01) |
| ***A61K 31/519*** | (2006.01) |
| *A61P 35/04* | (2006.01) |
| *A61P 25/28* | (2006.01) |
| *A61P 25/16* | (2006.01) |

(52) U.S. Cl. ............................ 514/217.06; 514/260.1; 514/234.2; 514/252.16; 514/227.8; 544/61; 544/117; 544/255; 540/524

(58) Field of Classification Search ................ 544/255, 544/61, 117; 514/260.1, 217.06, 234.2, 227.8, 514/252.16; 540/524

See application file for complete search history.

(56) References Cited

U.S. PATENT DOCUMENTS

2004/0053908 A1 3/2004 Funahashi et al.
2007/0244133 A1 * 10/2007 Bower et al. ............. 514/260.1

OTHER PUBLICATIONS

CAS printout, pp. 1-9, downloaded Apr. 24, 2008.*
Goldenberg-Furmanov, et al., Cancer Research, Feb. 1, 2004, 64, 1058-1064.
Shah, et al., Science, Jul. 16, 2004, vol. 305, 399-401.
Donato, et al., Blood, Jan. 15, 2003, 101(2), 690-698.
Wobig, D., Liebigs Ann. Chem., 1989, 409-412 (See English Abstract).
McKee RL and Bost RW, *J. Am. Chem. Soc.*, 1946, 68, 2506-7.
International Search Report re: PCT/US06/30149 dated Aug. 24, 2007.

* cited by examiner

*Primary Examiner*—Brenda L Coleman
*Assistant Examiner*—Susanna Moore

(57) ABSTRACT

The present invention is directed to novel thiazolopyrimidine compounds of Formula (I) or a form or composition thereof

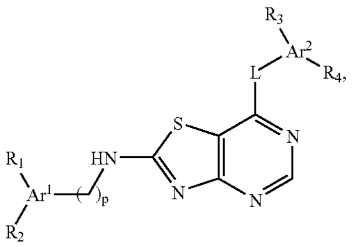

and the use thereof as inhibitors of ATP-protein kinase interactions.

5 Claims, No Drawings

SUBSTITUTED THIAZOLO [4,5-D]PYRIMIDINES AS PROTEIN KINASE INHIBITORS

CROSS REFERENCE TO RELATED APPLICATIONS

This present application claims benefit of U.S. Provisional Patent Application Ser. No. 60/706,840, filed Aug. 8, 2005, which is incorporated herein by reference in its entirety and for all purposes.

FIELD OF THE INVENTION

The present invention is in the area of novel thiazolopyrimidine compounds or forms thereof, their syntheses and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met1 or c-MET), PDGFR-α, PDGFR-β, Tie-1, Tie-2 (also Tek-1 or Tek), VEGFRI (also FLT-1), VEGFR2 (also KDR), FLT-3, FLT-4, c-KIT, JAKI, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 (A and B), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

Protein kinases play very important roles in the normal regulation of cell growth. However, as a result of either mutation or overexpression of the tyrosine kinases (receptor or non-receptor) or the ligands of the receptor tyrosine kinases, signaling can become deregulated, resulting in uncontrolled cell proliferation leading to cancer or a related disease.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Uncontrolled signaling for cell growth due to defective control of protein phosphorylation has also been implicated in a number of diseases, such as osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus CMV), heart disease (such as atherosclerosis, neointima formation or transplantation-induced vasculopathies (such as restenosis and the like)) lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like). Therefore, kinase inhibitors have potential use as therapeutic agents.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-α (TGF-α) and the HER-3 ligand heregulin are three of the ligands that bind to the EGFR receptors.

For example, EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs. Diseases associated with increased EGFR expression include proliferative glomerulonephritis, diabetes-induced renal disease and chronic pancreatitis. Overexpression of HER2 has been associated with breast and ovarian cancer. Diseases associated with the overproduction of TGF-α, rather than overexpression of EGFR, include psoriasis, a cell-proliferative skin disorder. Since EGFR expression levels in uterine tissues are elevated during implantation of a fertilized egg, an EGFR inhibitor may also have potential use as a contraceptive to reduce fertility.

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG 1478 has been shown to reduce the viral load in cells that were infected in the presence of the tyrphostin (Wang, et al., Nature, 24 Jul. 2003, Vol 424). Accordingly, potent EGFR selective inhibitors may be useful in anti-CMV therapy.

The Src family of tyrosine-kinases includes the sub-family proteins c-Src, Lyn, Fyn, Lck, Syk, Hck, Yes, Blk, Fgr and Frk. While various members of the c-Src family are important for normal cellular proliferation, their overexpression and overactivation can promote development of cancer (Yeatman T J, Nature, June 2004, Vol. 4). For example, the Lyn kinase has been shown to be upregulated in hormone resistant prostate cancer. Tumor xenografts of hormone resistant prostate cancer cells showed delayed growth upon treatment with peptides that specifically block Lyn kinase activity (Goldenberg-Furmanov, et al., Cancer Research, 1 Feb. 2004, 64, 1058-1064).

The Lyn and Hck Src sub-family tyrosine-kinases have both been implicated in chronic myeloid leukemia (CML). CML is caused by the BCR-Abl fusion protein that results from the t(9;22) chromosomal translocation that juxtaposes the c-Abl non-receptor tyrosine kinase gene on chromosome 9 with a breakpoint cluster region (bcr) gene on chromosome 22. The BCR-Abl fusion protein is a constitutively activated form of the Abl tyrosine kinase that drives uncontrolled growth leading to CML and many cases of adult acute lymphoblastic leukemia. Gleevec, which is an inhibitor of Abl has been successfully used to treat CML. However, Gleevec does not help patients in blast crisis because they carry mutant forms of BCR-Abl that no longer bind Gleevec. Such Gleevec resistant CML cells are sensitive to a dual src/BCR-Abl inhibitor that binds and inhibits the mutant BCR-Abl and members of the src family (Shah, et al., Science, 16 Jul. 2004, Vol 305, 399-401). There are also other ways that CML cells can become resistant to treatment with the tyrosine kinase Abl inhibitor Gleevec. For example, CML K562 cells that become resistant to Gleevec minimize reliance on the BCR-Abl translocation for growth and instead upregulate the Lyn and Hck kinases. This was demonstrated by expressing antisense Lyn in these cells, which reduced their rate of proliferation (Donato, et al., Blood, 15 Jan. 2003, 101(2)). c-Src and other Src family members are also involved in cellular adhesion, invasion and motility of tumor cells. Thus, small molecule inhibitors of the Src kinase family could offer new therapeutic opportunities for both leukemias and solid tumors.

SUMMARY OF THE INVENTION

A first aspect of the present invention is novel compounds of Formula (I) or a form thereof:

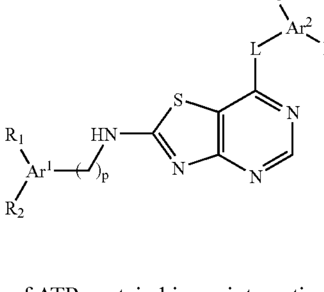

as inhibitors of ATP-protein kinase interactions.

A second aspect of this invention is a composition or medicament comprising one or more compounds of Formula (I) or a form thereof.

A third aspect of this invention is a method of synthesizing compounds of Formula (I) or a form thereof.

A fourth aspect of this invention is the use of one or more compounds of Formula (I) or a form thereof as protein kinase inhibitors. The aspect of the protein kinases includes serine/threonine kinases and tyrosine kinases. The aspect of the kinases further includes kinase selected from EGFR, HER-2, c-Src, Lyn, c-Abl and the like. Also in this aspect, the compounds of Formula (I) or a form thereof are useful for preventing, treating or ameliorating chronic or acute kinase mediated diseases. The aspect of a kinase mediated disease includes an EGFR protein kinase mediated cytomegalovirus (CMV) infection. In a related aspect, the compounds of Formula (I) or a form thereof are useful contraceptive agents.

A fifth aspect of this invention is a method for ameliorating, treating or preventing a chronic or acute kinase mediated disease in a patient in need thereof comprising administering to the patient an effective amount of one or more compounds of Formula (I) or a form thereof.

In this aspect, the chronic or acute disease is mediated by a kinase selected from EGFR, HER-2, c-Src, Lyn, c-Abl and the like. Also in this aspect, the method includes inhibiting unregulated kinase activity in the patient. The aspect of unregulated kinase activity includes unregulated kinase expression or signaling, unregulated expression or signaling of a kinase selected from EGFR, HER-2, c-Src, Lyn, c-Abl and the like and unregulated expression or signaling which results in unregulated cell proliferation. The aspect of unregulated cell proliferation includes cancer, metastatic cancer cell invasion or metastatic cancer cell migration. The aspect of cancer includes tumors mediated by the unregulated activity of kinases selected from EGFR, HER-2, c-Src, Lyn, c-Abl and the like. The aspect of cancer further includes non-small-cell lung cancers, colon cancers, breast cancers and the like. An aspect of the method includes an amount of one or more compounds of Formula (I) or a form thereof which is effective to induce remission of a chronic form of a cancer. The aspect of the effective amount includes an amount which is effective at a low dose to inhibit unregulated kinase activity.

A sixth aspect of this invention is a method for use of one or more compounds of Formula (I) or a form thereof in the preparation of a composition or medicament for preventing, treating or ameliorating chronic or acute kinase mediated diseases in a patient in need thereof. This aspect of the method includes administering to the patient an effective amount of a compound of Formula (I) or a form thereof in the form of a composition or medicament.

These and other aspects and advantages of the invention, which will become apparent in light of the detailed description below, are achieved through use of the compounds of this invention.

DETAILED DESCRIPTION OF THE INVENTION

The present invention provides thiazolopyrimidine compounds of Formula (I):

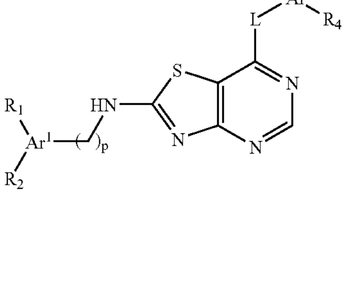

and a form thereof, wherein p is 0, 1, 2 or 3;

L is selected from the group consisting of O, S, $N(R_5)$ and a bond;

$R_5$ is selected from the group consisting of hydrogen, $C_{1-8}$alkyl and $C_{1-8}$alkyl($C_{1-8}$alkoxy);

$Ar^1$ is selected from the group consisting of aryl, heteroaryl and heterocyclyl;

$R_1$ and $R_2$ is each independently selected from the group consisting of (1) hydrogen,
(2) $C_{1-8}$alkyl,
(3) $C_{2-8}$alkenyl,
(4) $C_{2-8}$alkynyl,
(5) $C_{1-8}$alkoxy,
  wherein (2), (3), (4) and (5) is each optionally substituted with one, two or three substituents independently selected from the group consisting of
  (i) $C_{3-8}$cycloalkyl,
  (ii) aryl,
  (iii) heteroaryl,
  (iv) heterocyclyl,
    wherein (i), (ii), (iii) and (iv) are optionally substituted with one, two or three substituents independently selected from the group consisting of
    (a) $C_{1-8}$alkyl,
    (b) $C_{1-8}$alkoxy,
    (c) $C_{1-8}$alkyl($C_{1-8}$alkoxy),
    (d) $C_{1-8}$alkyl(halogen)$_{1-3}$,
    (e) $C_{1-8}$alkyl(hydroxy)$_{1-3}$,
    (f) $CO_2$($C_{1-8}$alkyl),
    (g) amino optionally mono or disubstituted with $C_{1-8}$alkyl,
    (h) cyano,
    (i) halogen,
    (j) hydroxy,
    (k) $C_{1-8}$alkyl(amino) optionally mono or disubstituted on amino with $C_{1-8}$alkyl,
    (l) $C_{3-8}$cycloalkyl, and
    (m) aryl optionally substituted with $C_{1-8}$alkyl, halogen, hydroxy, and
  (v) amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(hydroxy)$_{L-3}$,
    (d) $C_{3-8}$cycloalkyl,
    (e) heterocyclyl optionally substituted with one or two $C_{1-8}$alkyl substituents, and
    (f) $C_{1-8}$alkyl(heterocyclyl) optionally substituted on heterocyclyl with one or two $C_{1-8}$alkyl substituents,
(6) amino optionally mono or disubstituted with a substituent independently selected from the group consisting of
  (i) $C_{1-8}$alkyl,
  (ii) heterocyclyl optionally substituted with one or two $C_{1-8}$alkyl substituents, and
  (iii) $C_{1-8}$alkyl(heterocyclyl) optionally substituted on heterocyclyl with one or two $C_{1-8}$alkyl substituents,
(7) cyano,
(8) halogen,
(9) hydroxy,
(10) $C_{3-8}$cycloalkyl,
(11) aryl,
(12) heteroaryl,
(13) heterocyclyl,
(14) $SO_2$(heterocyclyl) optionally substituted on heterocyclyl with one or two $C_{1-8}$alkyl substituents,
(15) C(O) substituted with a substituent selected from the group consisting of
  (i) hydroxy,
  (ii) $C_{1-8}$alkyl,
  (iii) $C_{1-8}$alkoxy, and
  (iv) amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(amino) optionally mono or disubstituted on amino with $C_{1-8}$alkyl, and
    (d) $C_{1-8}$alkyl(hydroxy)$_1$-$_3$, and
(16) $SO_2$(amino) optionally mono or disubstituted on amino with a substituent independently selected from the group consisting of
  (i) $C_{1-8}$alkyl,
  (ii) $C_{1-8}$alkyl($C_{1-8}$alkoxy),
  (iii) $C_{1-8}$alkyl(amino) optionally mono or disubstituted on amino with $C_{1-8}$alkyl,
  (iv) $C_{1-8}$alkyl(hydroxy)$_{1-3}$, and
  (v) $C_{1-8}$alkyl(heterocyclyl) optionally substituted on heterocyclyl with one or two $C_{1-8}$alkyl substituents;

$Ar^2$ is selected from the group consisting of aryl and heteroaryl; and $R_3$ and $R_4$ is each independently selected from the group consisting of (1) hydrogen,
(2) $C_{1-8}$alkyl,
(3) $C_{2-8}$alkenyl,
(4) $C_{2-8}$alkynyl,
(5) $C_{1-8}$alkoxy,
  wherein (2), (3), (4) and (5) is each optionally substituted with one, two or three substituents independently selected from the group consisting of
  (i) halogen,
  (ii) hydroxy,
  (iii) $C_{3-8}$cycloalkyl, and
  (iv) aryl,
    wherein (iii) and (iv) are optionally substituted with one, two or three substituents independently selected from the group consisting of
    (a) $C_{1-8}$alkyl,
    (b) $C_{1-8}$alkoxy,
    (c) halogen, and
    (d) hydroxy,
(6) amino optionally mono or disubstituted with $C_{1-8}$alkyl,
(7) oxy substituted with a substituent selected from the group consisting of
  (i) $C_{3-8}$cycloalkyl,
  (ii) aryl, and
  (iii) heteroaryl,
(8) cyano,
(9) halogen,
(10) hydroxy,
(11) nitro, and
(12) heterocyclyl.

An example of the present invention is a compound of Formula (I) and a form thereof wherein p is 0, 2 or 3.

An example of the present invention is a compound of Formula (I) and a form thereof wherein L is $N(R_5)$.

An example of the present invention is a compound of Formula (I) and a form thereof wherein $R_5$ is hydrogen or $C_{1-8}$alkyl.

An example of the present invention is a compound of Formula (I) and a form thereof wherein $Ar^1$ is selected from the group consisting of aryl, heteroaryl and heterocyclyl.

An example of the present invention is a compound of Formula (I) and a form thereof wherein $R_1$ and $R_2$ is each independently selected from the group consisting of (1) hydrogen,
(2) $C_{1-8}$alkyl,
(3) $C_{1-8}$alkoxy,
  wherein (2) and (3) is each optionally substituted with one, two or three substituents independently selected from the group consisting of
  (i) heteroaryl,
  (ii) heterocyclyl,
    wherein (i) and (ii) are optionally substituted with one, two or three substituents independently selected from the group consisting of
    (a) $C_{1-8}$alkyl,
    (b) $C_{1-8}$alkoxy,
    (c) $C_{1-8}$alkyl($C_{1-8}$alkoxy),
    (d) $C_{1-8}$alkyl(hydroxy)$_{1-3}$,
    (e) $CO_2$($C_{1-8}$alkyl),
    (f) amino optionally mono or disubstituted with $C_{1-8}$alkyl,
    (g) $C_{1-8}$alkyl(amino) optionally mono or disubstituted on amino with $C_{1-8}$alkyl, and
    (h) aryl optionally substituted with $C_{1-8}$alkyl, halogen, hydroxy, and
  (iii) amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(hydroxy)$_{1-3}$,
    (d) $C_{3-8}$cycloalkyl,
    (e) heterocyclyl optionally substituted with one or two $C_{1-8}$alkyl substituents, and
    (f) $C_{1-8}$alkyl(heterocyclyl) optionally substituted on heterocyclyl with one or two $C_{1-8}$alkyl substituents,
(4) amino optionally mono or disubstituted with a substituent independently selected from the group consisting of
  (i) $C_{1-8}$alkyl,
  (ii) heterocyclyl optionally substituted with one or two $C_{1-8}$alkyl substituents, and
  (iii) $C_{1-8}$alkyl(heterocyclyl) optionally substituted on heterocyclyl with one or two $C_{1-8}$alkyl substituents,
(5) cyano,
(6) halogen,
(7) hydroxy,
(8) $C_{3-8}$cycloalkyl,
(9) aryl,
(10) heteroaryl,
(11) heterocyclyl,
(12) $SO_2$(heterocyclyl) optionally substituted on heterocyclyl with one or two $C_{1-8}$alkyl substituents,
(13) C(O)amino optionally mono or disubstituted on amino with $C_{1-8}$alkyl, and
(14) $SO_2$(amino) optionally mono or disubstituted on amino with a substituent independently selected from the group consisting of
  (i) $C_{1-8}$alkyl,
  (ii) $C_{1-8}$alkyl($C_{1-8}$alkoxy),
  (iii) $C_{1-8}$alkyl(amino) optionally mono or disubstituted on amino with $C_{1-8}$alkyl,
  (iv) $C_{1-8}$alkyl(hydroxy)$_{1-3}$, and
  (v) $C_{1-8}$alkyl(heterocyclyl).

An example of the present invention is a compound of Formula (I) and a form thereof wherein $R_1$ and $R_2$ is each independently selected from the group consisting of (1) hydrogen,
(2) $C_{1-8}$alkyl,
(3) $C_{1-8}$alkoxy,
  wherein (2) and (3) is each optionally substituted with a substituent selected from the group consisting of
  (i) heteroaryl,
  (ii) heterocyclyl,
    wherein (i) and (ii) are optionally substituted with one or two substituents independently selected from the group consisting of
    (a) $C_{1-8}$alkyl,
    (c) $C_{1-8}$alkyl($C_{1-8}$alkoxy),
    (d) $C_{1-8}$alkyl(hydroxy)$_{1-3}$,
    (e) $CO_2$($C_{1-8}$alkyl),
    (g) $C_{1-8}$alkyl(amino), and
    (h) aryl optionally substituted with halogen, and
  (iii) amino optionally mono or disubstituted with a substituent independently selected from the group consisting of
    (a) $C_{1-8}$alkyl,
    (b) $C_{1-8}$alkyl($C_{1-8}$alkoxy),
    (c) $C_{1-8}$alkyl(hydroxy)$_{1-3}$,
    (d) $C_{3-8}$cycloalkyl,
    (e) heterocyclyl optionally substituted with one or two $C_{1-8}$alkyl substituents, and
    (f) $C_{1-8}$alkyl(heterocyclyl) optionally substituted on heterocyclyl with one or two $C_{1-8}$alkyl substituents,
(4) amino optionally mono or disubstituted with $C_{1-8}$alkyl (heterocyclyl),
(5) cyano,
(6) hydroxy,
(7) heterocyclyl,
(8) $SO_2$(heterocyclyl),
(9) C(O)amino optionally mono or disubstituted on amino with $C_{1-8}$alkyl, and
(10) $SO_2$(amino) optionally mono or disubstituted on amino with a substituent independently selected from the group consisting of
  (i) $C_{1-8}$alkyl($C_{1-8}$alkoxy),
  (ii) $C_{1-8}$alkyl(amino) optionally mono or disubstituted on amino with $C_{1-8}$alkyl,
  (iii) $C_{1-8}$alkyl(hydroxy)$_{1-3}$, and
  (iv) $C_{1-8}$alkyl(heterocyclyl).

An example of the present invention is a compound of Formula (I) and a form thereof wherein $Ar^2$ is selected from the group consisting of aryl and heteroaryl.

An example of the present invention is a compound of Formula (I) and a form thereof wherein $R_3$ and $R_4$ is each independently selected from the group consisting of (1) hydrogen,
(2) $C_{1-8}$alkyl,
(3) $C_{2-8}$alkynyl,
(4) $C_{1-8}$alkoxy,
  wherein (2), (3) and (4) is each optionally substituted with one, two or three substituents independently selected from the group consisting of
  (i) $C_{3-8}$cycloalkyl, and
  (ii) aryl,
    wherein (i) and (ii) are optionally substituted with one, two or three substituents independently selected from the group consisting of
    (a) $C_{1-8}$alkyl,
    (b) $C_{1-8}$alkoxy, (c) halogen, and (d) hydroxy, (5) amino optionally mono or disubstituted with $C_{1-8}$alkyl, (6) oxy substituted with a substituent selected from the group consisting of (i) $C_{3-8}$cycloalkyl, (ii) aryl, and (iii) heteroaryl, (7) cyano, (8) halogen, (9) hydroxy,

(10) nitro, and

(11) heterocyclyl.

An example of the present invention is a compound of Formula (I) and a form thereof wherein $R_3$ and $R_4$ is each independently selected from the group consisting of (1) hydrogen, (2) $C_{1-8}$alkyl, (3) $C_{2-8}$alkynyl, (4) $C_{1-8}$alkoxy, (5) $C_{1-8}$alkoxy(aryl), wherein aryl is optionally substituted with one, two or three halogen substituents, (5) cyano, (6) halogen, (7) nitro, and (8) heterocyclyl.

An example of the present invention is a compound of Formula (I) and a form thereof, selected from a compound of Formula (Ia):

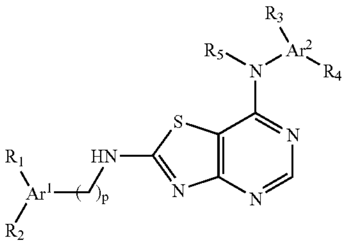

and a form thereof, wherein p is 0, 2 or 3,

L is $N(R_5)$, $R_5$ is hydrogen or $C_{1-8}$alkyl, $Ar^1$ is selected from the group consisting of aryl, heteroaryl and heterocyclyl, $R_1$ and $R_2$ is each independently selected from the group consisting of (1) hydrogen, (2) $C_{1-8}$alkyl, (3) $C_{1-8}$alkoxy, wherein (2) and (3) is each optionally substituted with a substituent selected from the group consisting of (i) heteroaryl, (ii) heterocyclyl, wherein (i) and (ii) are optionally substituted with one or two substituents independently selected from the group consisting of (a) $C_{1-8}$alkyl, (c) $C_{1-8}$alkyl($C_{1-8}$alkoxy), (d) $C_{1-8}$alkyl$(hydroxy)_{1-3}$, (e) $CO_2$($C_{1-8}$alkyl), (g) $C_{1-8}$alkyl(amino), and (h) aryl optionally substituted with halogen, and (iii) amino optionally mono or disubstituted with a substituent independently selected from the group consisting of (a) $C_{1-8}$alkyl, (b) $C_{1-8}$alkyl($C_{1-8}$alkoxy), (c) $C_{1-8}$alkyl$(hydroxy)_{1-3}$, (d) $C_{3-8}$cycloalkyl, (e) heterocyclyl optionally substituted with one or two $C_{1-8}$alkyl substituents, and (f) $C_{1-8}$alkyl(heterocyclyl) optionally substituted on heterocyclyl with one or two $C_{1-8}$alkyl substituents, (4) amino optionally mono or disubstituted with $C_{1-8}$alkyl (heterocyclyl), (5) cyano, (6) hydroxy, (7) heterocyclyl, (8) $SO_2$(heterocyclyl), (9) C(O)amino optionally mono or disubstituted on amino with $C_{1-8}$alkyl, and

(10) $SO_2$(amino) optionally mono or disubstituted on amino with a substituent independently selected from the group consisting of (i) $C_{1-8}$alkyl($C_{1-8}$alkoxy), (ii) $C_{1-8}$alkyl(amino) optionally mono or disubstituted on amino with $C_{1-8}$alkyl, (iii) $C_{1-8}$alkyl$(hydroxy)_{1-3}$, and (iv) $C_{1-8}$alkyl(heterocyclyl), $Ar^2$ is selected from the group consisting of aryl and heteroaryl, and $R_3$ and $R_4$ is each independently selected from the group consisting of (1) hydrogen, (2) $C_{1-8}$alkyl, (3) $C_{2-8}$alkynyl, (4) $C_{1-8}$alkoxy, (5) $C_{1-8}$alkoxy(aryl), wherein aryl is optionally substituted with one, two or three halogen substituents, (5) cyano, (6) halogen, (7) nitro, and (8) heterocyclyl.

An example of the present invention is a compound of Formula (Ia) and a form of wherein p, $(R_1,R_2)Ar^1$, $R_5$ and $(R_3,R_4)Ar^2$ are dependently selected from:

| Cpd | p | 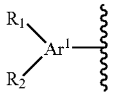 | $R_5$ | 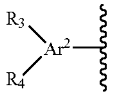 |
| --- | --- | --- | --- | --- |
| 1 | 0 | 4-morpholin-4-yl-phenyl | H | 3-Cl-4-F-phenyl |
| 2 | 0 | 4-$CH_2$-piperidin-1-yl-phenyl | H | 3-Cl-4-F-phenyl |
| 3 | 0 | 3-$CH_2$-morpholin-4-yl-phenyl | H | 3-Cl-4-F-phenyl |
| 4 | 0 | 4-$(CH_2)_2$-morpholin-4-yl-phenyl | H | 3-Cl-4-F-phenyl |

-continued

| Cpd | p | 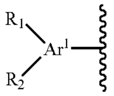 | $R_5$ | 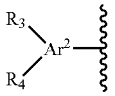 |
| --- | --- | --- | --- | --- |
| 5 | 0 | 4-$CH_2$-(4-$CH_3$-piperazin-1-yl)-phenyl | H | 3-Cl-4-F-phenyl |
| 6 | 0 | 3-$OCH_3$-4-$CH_2$-piperidin-1-yl-phenyl | H | 3-Cl-4-F-phenyl |
| 7 | 0 | 4-$CH_2$-(2-$CH_2CH_3$-imidazol-1-yl)-phenyl | H | 3-Cl-phenyl |
| 8 | 0 | 3-$CH_2$-piperidin-1-yl-phenyl | H | 3-Cl-phenyl |
| 9 | 0 | 4-$CH_2$-pyridin-4-yl-phenyl | H | 3-Cl-phenyl |
| 10 | 0 | 4-$CH_2N(CH_3)_2$-phenyl | H | 3-Cl-4-F-phenyl |
| 11 | 0 | 4-$(CH_2)_2N(CH_3)_2$-pbenyl | H | 3-Cl-4-F-phenyl |
| 12 | 0 | 4-$OCH_3$-phenyl | H | 3-Cl-4-F-phenyl |
| 13 | 0 | 4-OH-phenyl | H | 3-Cl-4-F-phenyl |
| 14 | 0 | 4-$O(CH_2)_2$-morpholin-4-yl-phenyl | H | 3-Cl-4-F-phenyl |
| 15 | 0 | 4-$O(CH_2)_2$-pyrrolidin-1-yl-phenyl | H | 3-Cl-4-F-phenyl |
| 16 | 0 | 4-$O(CH_2)_3$-[4-(4-Cl-phenyl)-piperazin-1-yl]-phenyl | H | 3-Cl-4-F-phenyl |
| 17 | 0 | 4-$CH_2$-pyrrolidin-1-yl-phenyl | H | 3-Cl-4-F-phenyl |
| 18 | 0 | 4-$CH_2$-morpholin-4-yl-phenyl | H | 3-Cl-4-F-phenyl |
| 19 | 0 | 4-$CH_2$-azepan-1-yl-phenyl | H | 3-Cl-4-F-phenyl |
| 20 | 0 | 4-$CH_2$-thiomorpholin-4-yl-phenyl | H | 3-Cl-4-F-phenyl |
| 21 | 0 | 4-$CH_2$-[$N(CH_3)$(cyclohexyl)]-phenyl | H | 3-Cl-4-F-phenyl |
| 22 | 0 | 4-$CH_2$-(4-$CH_2NH_2$-piperidin-1-yl)-phenyl | H | 3-Cl-4-F-phenyl |
| 23 | 0 | 4-$CH_2$-imidazol-1-yl-phenyl | H | 3-Cl-4-F-phenyl |
| 24 | 0 | 4-$CH_2$-[(3,5-$CH_3)_2$-piperidin-1-yl]-phenyl | H | 3-Cl-4-F-phenyl |
| 25 | 0 | 4-$CH_2$-[(2S)-2-$CH_2OH$-pyrrolidin-1-yl]-phenyl | H | 3-Cl-4-F-phenyl |
| 26 | 0 | 4-$CH_2$-[(2S)-2-$CH_2OCH_3$-pyrrolidin-1-yl]-phenyl | H | 3-Cl-4-F-phenyl |
| 27 | 0 | 4-$C(O)N(CH_3)_2$-phenyl | H | 3-Cl-4-F-phenyl |
| 28 | 0 | 4-$CH_2$-(4-$C(O)OCH_2CH_3$-piperazin-1-yl)-phenyl | H | 3-Cl-4-F-phenyl |
| 29 | 0 | 4-$CH_2$-(4-$C(O)OCH_2CH_3$-piperidin-1-yl)-phenyl | H | 3-Cl-4-F-phenyl |
| 30 | 0 | 4-$CH_2$-(2-$CH_2CH_3$-imidazol-1-yl)-phenyl | H | 3-Cl-4-F-phenyl |
| 31 | 0 | 4-$SO_2NH(CH_2)_3N(CH_3)_2$-phenyl | H | 3-Cl-4-F-phenyl |
| 32 | 0 | 4-$SO_2N[(CH_2)_2OCH_3]_2$-phenyl | H | 3-Cl-4-F-phenyl |
| 33 | 0 | 4-$SO_2N[(CH_2)_2OCH_3]_2$-phenyl | H | 3-C≡CH-phenyl |
| 34 | 0 | 4-$CH_2N[(CH_2)_2OCH_3]_2$-phenyl | H | 3-Cl-4-F-phenyl |
| 35 | 0 | 4-$CH_2$-morpholin-4-yl-phenyl | H | 3-C≡CH-phenyl |
| 36 | 0 | 4-$CH_2$-morpholin-4-yl-phenyl | H | 1-$CH_2$-phenyl-indazol-6-yl |
| 37 | 0 | 4-$SO_2NH(CH_2)_3N(CH_3)_2$-phenyl | H | 3-C≡CH-phenyl |
| 38 | 0 | 4-$CH_2N[(CH_2)_2OCH_3]_2$-phenyl | H | 3-C≡CH-phenyl |
| 39 | 0 | 4-$SO_2NH(CH_2)_2OH$-phenyl | H | 3-Cl-4-F-phenyl |
| 40 | 0 | 4-$SO_2NH(CH_2)_2$-morpholin-4-yl-phenyl | H | 3-Cl-4-F-phenyl |
| 41 | 0 | 4-$SO_2NH(CH_2)_3$-morpholin-4-yl-phenyl | H | 3-Cl-4-F-phenyl |
| 42 | 0 | 4-$CH_2$-pyrrolidin-1-yl-phenyl | H | 3-C≡CH-phenyl |
| 43 | 0 | 4-$CH_2$-piperidin-1-yl-phenyl | H | 3-C≡CH-phenyl |
| 44 | 0 | 4-$CH_2$-[(2S)-2-$CH_2OH$-pyrrolidin-1-yl]-phenyl | H | 3-C≡CH-phenyl |
| 45 | 0 | 4-$SO_2$-morpholin-4-yl-phenyl | H | 3-C≡CH-phenyl |
| 46 | 0 | 4-$SO_2$-morpholin-4-yl-phenyl | H | 3-Cl-4-F-phenyl |
| 47 | 0 | 4-$CH_2$-(4-$CH_3$-piperazin-1-yl)-phenyl | H | 3-C≡CH-pbenyl |
| 48 | 0 | 4-$CH_2$-(2-$CH_2CH_3$-imidazol-1-yl)-phenyl | H | 3-C≡CH-phenyl |
| 49 | 0 | 4-$CH_2N(CH_3)_2$-phenyl | H | 3-C≡CH-phenyl |
| 50 | 0 | 4-$(CH_2)_2$-morpholin-4-yl-phenyl | H | 3-C≡CH-phenyl |
| 51 | 2 | morpholin-4-yl | H | 3-Cl-4-F-phenyl |
| 52 | 3 | morpholin-4-yl | H | 3-Cl-4-F-phenyl |
| 53 | 0 | 4-$CH_2NH(CH_2)_2OCH(CH_3)_2$-phenyl | H | 3-Cl-4-F-phenyl |
| 54 | 0 | 4-$CH_2$-[(2R)-2-$CH_2OH$-pyrrolidin-1-yl]-phenyl | H | 3-C≡CH-phenyl |
| 55 | 0 | 4-$CH_2NH(CH_2)_2OCH(CH_3)_2$-phenyl | H | 3-C≡CH-phenyl |
| 56 | 0 | 4-$CH_2$-morpholin-4-yl-phenyl | H | 2-$OCH_3$-5-Cl-phenyl |
| 57 | 0 | 4-$CH_2$-morpholin-4-yl-phenyl | H | 3-Cl-phenyl |
| 58 | 0 | 4-$SO_2NH(CH_2)_2OH$-phenyl | H | 3-C≡CH-phenyl |
| 59 | 0 | 4-$CH_2N\{(CH_3)[(2R)-CH_2$-tetrahydro-furan-2-yl]}-phenyl | H | 3-Cl-4-F-phenyl |
| 60 | 0 | 4-$CH_2N\{(CH_3)$ [(2S)-$CH_2$-tetrahydro-furan-2-yl]}-phenyl | H | 3-Cl-4-F-phenyl |
| 61 | 0 | 4-$CH_2N[CH_2CH(OH)CH_3]_2$-phenyl | H | 3-C≡CH-phenyl |

-continued

| Cpd | p | 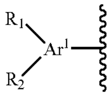 | $R_5$ | 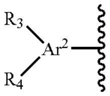 |
|---|---|---|---|---|
| 62 | 0 | 4-$CH_2NHCH_2$-[2,2-$(CH_3)_2$-[1,3]dioxolan-4-yl]-phenyl | H | 3-C≡CH-phenyl |
| 63 | 0 | 4-$CH_2N[(CH_3)$(tetrahydro-pyran-4-yl)]-phenyl | H | 3-C≡CH-phenyl |
| 64 | 0 | 4-$CH_2NH$[(2R)-$CH_2$-tetrahydro-furan-2-yl]-phenyl | H | 3-C≡CH-phenyl |
| 65 | 0 | 4-$CH_2$-morpholin-4-yl-phenyl | H | 3-$NO_2$-4-F-phenyl |
| 66 | 0 | 4-$CH_2NHCH_2CH(OH)CH_2OH$-phenyl | H | 3-C≡CH-phenyl |
| 67 | 0 | 4-$CH_2NH$[(2R)-$CH_2$-tetrahydro-furan-2-yl]-phenyl | H | 3-Cl-4-F-phenyl |
| 68 | 0 | 4-$CH_2$-(4-$CH_3$-piperazin-1-yl)-phenyl | H | 3-Cl-4-$OCH_2$-(3-F-phenyl)-phenyl |
| 69 | 0 | 6-$OCH_3$-pyridin-3-yl | H | 3-C≡CH-phenyl |
| 70 | 0 | 6-$OCH_3$-pyridin-3-yl | H | 3-Cl-4-F-phenyl |
| 71 | 0 | 6-$NH_2$-pyridin-3-yl | H | 3-Cl-4-F-phenyl |
| 72 | 0 | 6-$NH(CH_2)_3$-morpholin-4-yl-pyridin-3-yl | H | 3-C≡CH-phenyl |
| 73 | 0 | 4-$SO_2NH_2$-phenyl | H | 3-Cl-4-F-phenyl |
| 74 | 0 | 4-$SO_2NH_2$-phenyl | H | 3-Cl-phenyl |
| 75 | 0 | 4-$SO_2NH_2$-phenyl | H | 2,6-$F_2$-phenyl |
| 76 | 0 | 4-$SO_2NH_2$-phenyl | H | 2-F-4-Cl-phenyl |
| 77 | 0 | 4-$SO_2NH_2$-phenyl | H | 2-F-4-Br-phenyl |
| 78 | 0 | 4-$SO_2NH_2$-phenyl | H | 3-Br-phenyl |
| 79 | 0 | 4-$SO_2NH_2$-phenyl | H | 3-$CH_3$-phenyl |
| 80 | 0 | 4-$SO_2NH_2$-phenyl | H | phenyl |
| 81 | 0 | 4-$SO_2NH_2$-phenyl | H | 3,5-$Cl_2$-phenyl |
| 82 | 0 | 4-$SO_2NH_2$-phenyl | H | 3-Cl-4-Br-phenyl |
| 83 | 0 | 4-$SO_2NH_2$-phenyl | H | 3-Cl-4-morpholin-4-yl-phenyl |
| 84 | 0 | 4-$SO_2NH_2$-phenyl | $CH_3$ | 3-morpholin-4-yl-phenyl |
| 85 | 0 | 4-$SO_2NH_2$-phenyl | $CH_2CH_3$ | 4-morpholin-4-yl-phenyl |
| 86 | 0 | 4-$SO_2NH_2$-phenyl | H | 4-morpholin-4-yl-phenyl |
| 87 | 0 | 4-$SO_2NH_2$-phenyl | $CH_3$ | 3-morpholin-4-yl-4-$OCH_3$-phenyl |
| 88 | 0 | phenyl | H | 3-Cl-4-F-phenyl |
| 89 | 0 | phenyl | H | 3-Cl-phenyl |
| 90 | 0 | phenyl | H | 3-Br-phenyl |
| 91 | 0 | phenyl | H | 3,5-$Cl_2$-phenyl |
| 92 | 0 | 4-CN-phenyl | H | 3-Cl-4-F-phenyl |
| 93 | 0 | 4-CN-phenyl | H | 3-Cl-phenyl |
| 94 | 0 | 4-$CH_2$-(4-$CH_3$-piperazin-1-yl)-phenyl | H | 4-phenoxy-phenyl |

Compounds representative of a compound of Formula (I) or a form thereof include compounds and forms thereof selected from:

Cpd 1

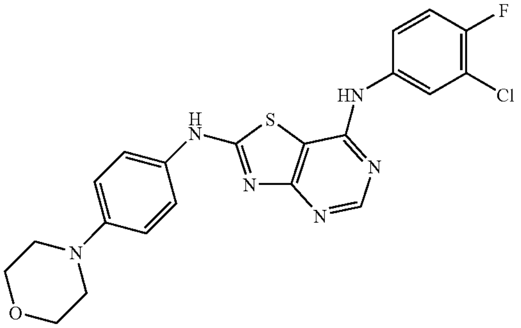

-continued

Cpd 2

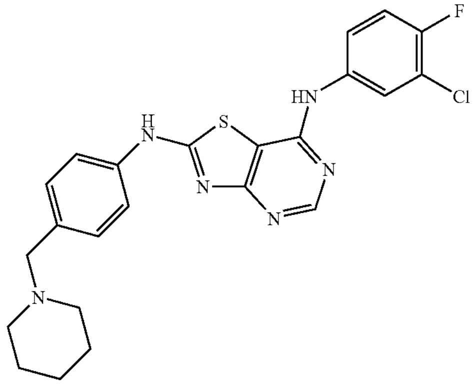

-continued
Cpd 3
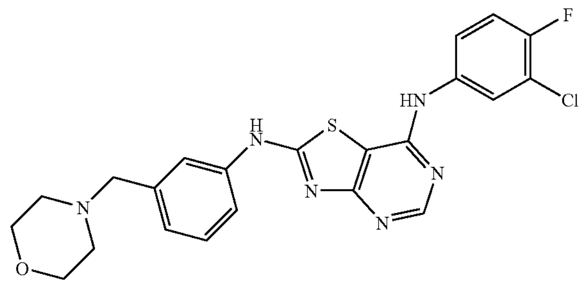
Cpd 4
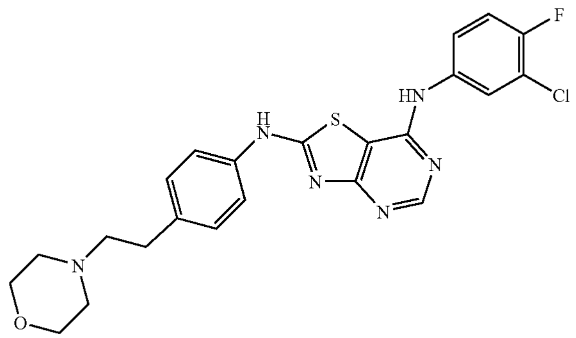
Cpd 5
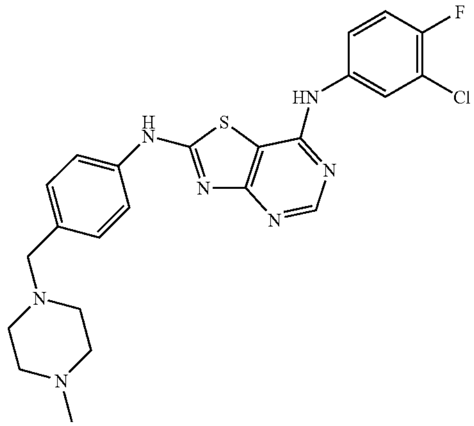
Cpd 6
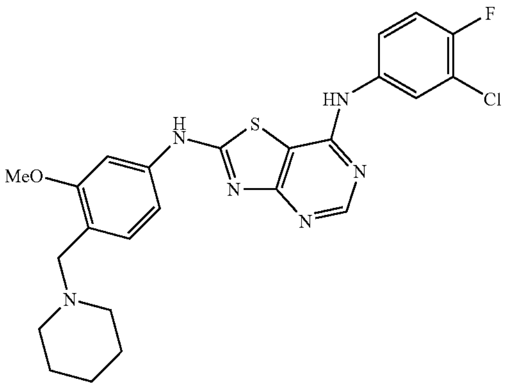
-continued
Cpd 7
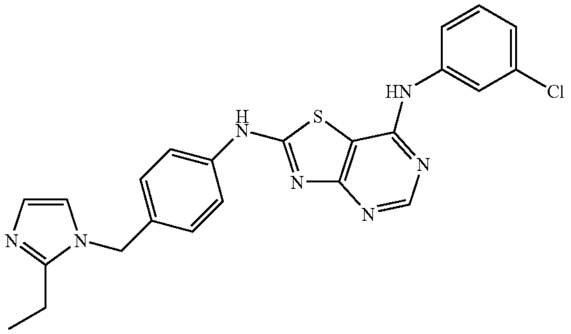
Cpd 8
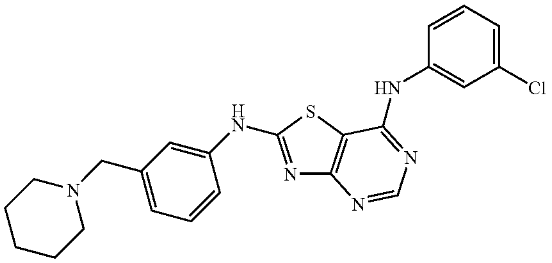
Cpd 9
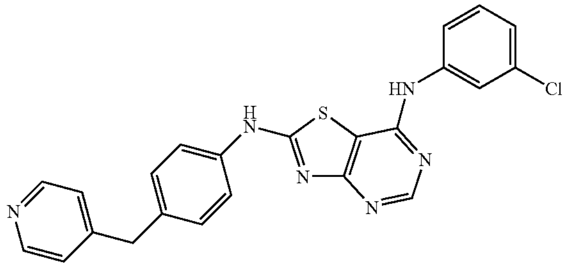
Cpd 10
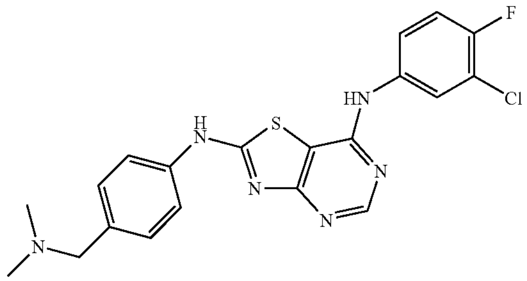
Cpd 11
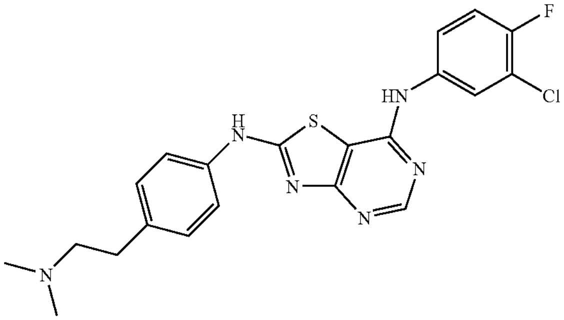

-continued
Cpd 12
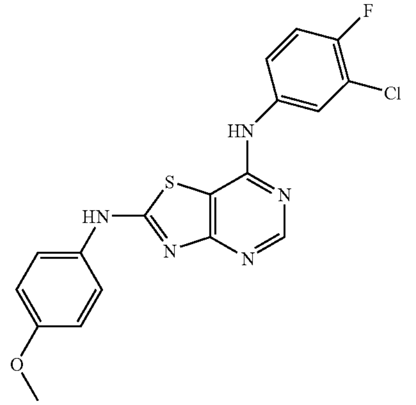
Cpd 13
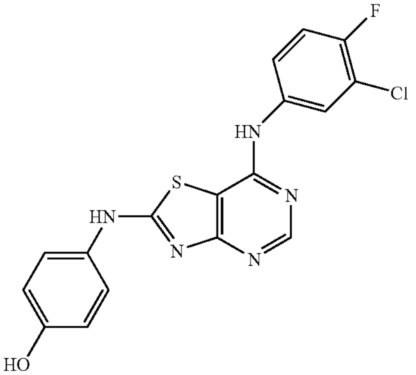
Cpd 14
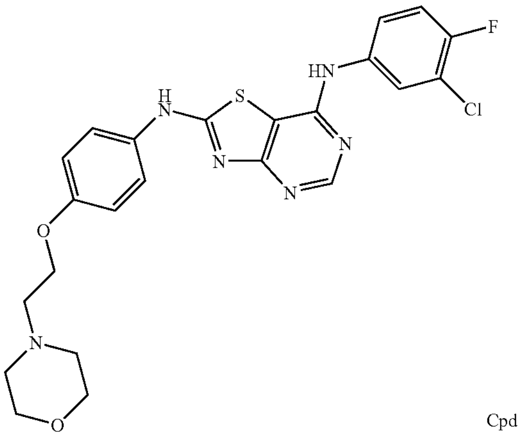
Cpd 15
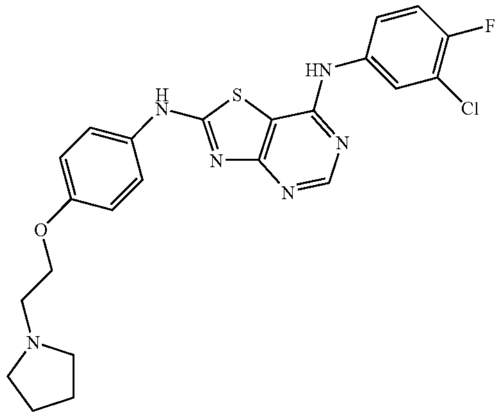
-continued
Cpd 16
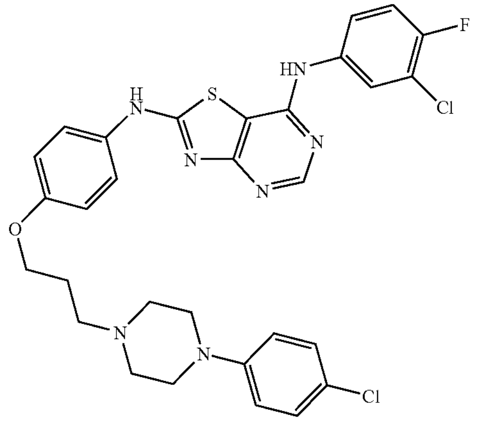
Cpd 17
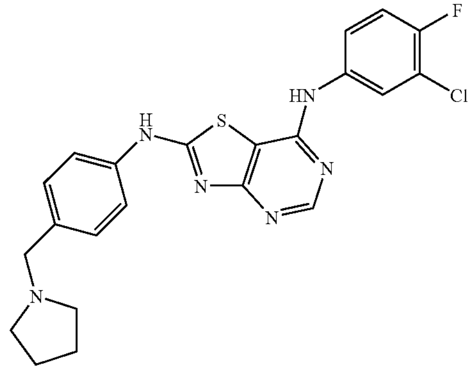
Cpd 18
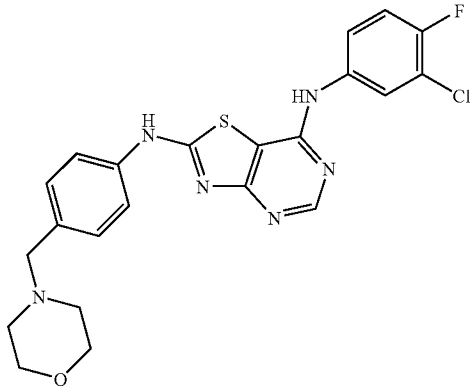
Cpd 19
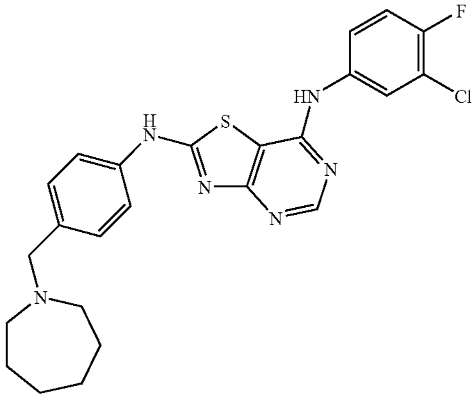

-continued
Cpd 20
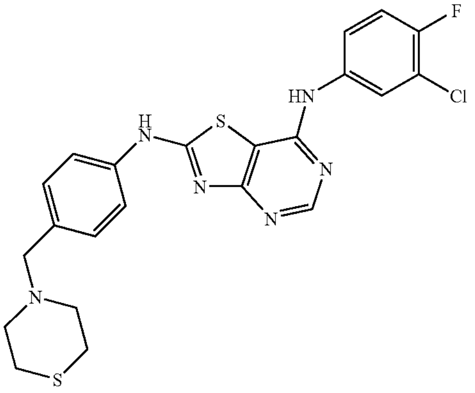
Cpd 21
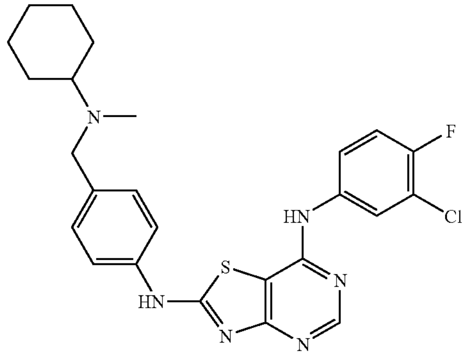
Cpd 22
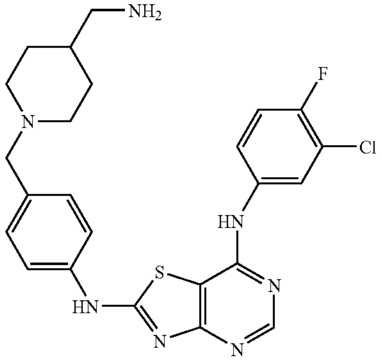
Cpd 23
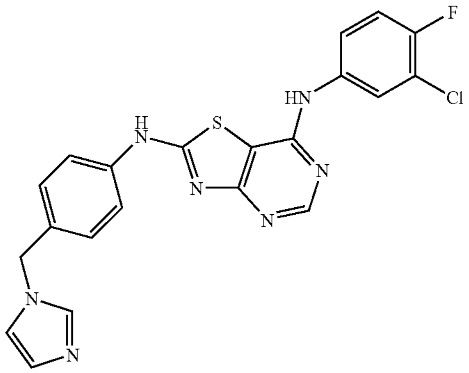
-continued
Cpd 24
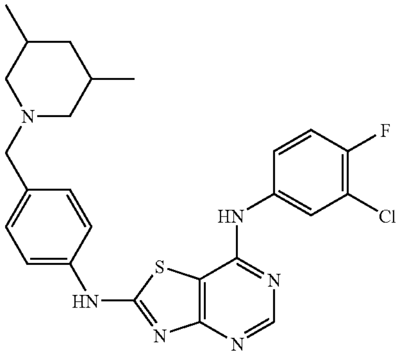
Cpd 25
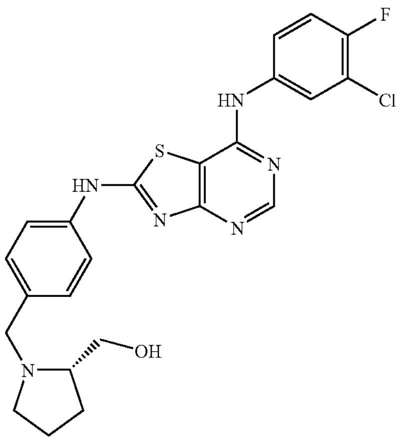
Cpd 26
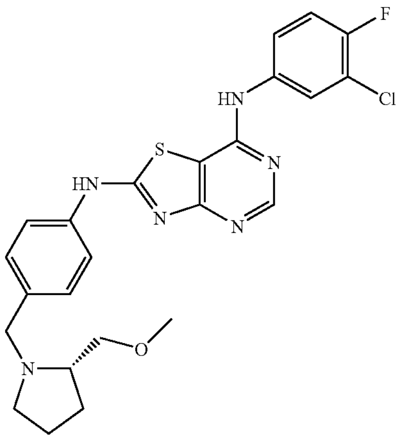
Cpd 27
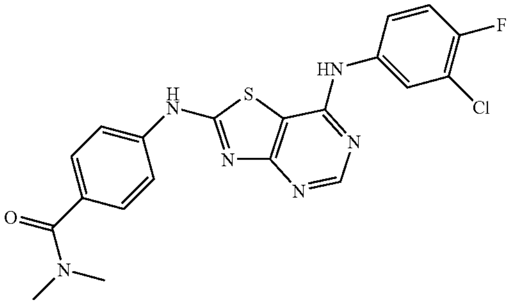

-continued
Cpd 28
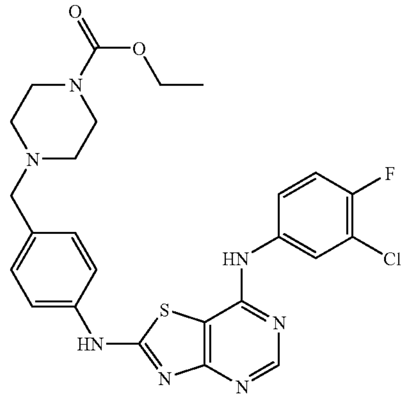
Cpd 29
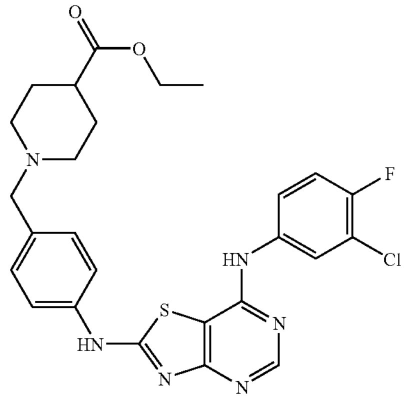
Cpd 30
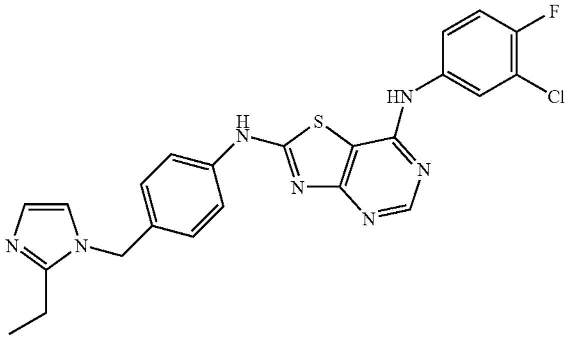
Cpd 31
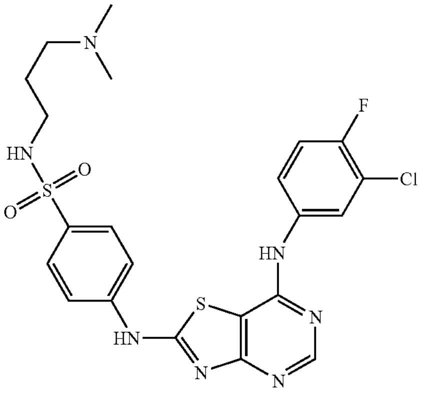
-continued
Cpd 32
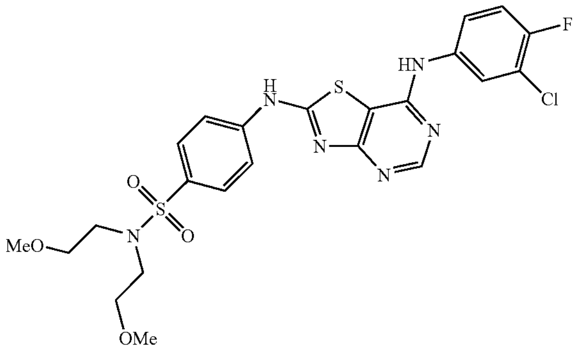
Cpd 33
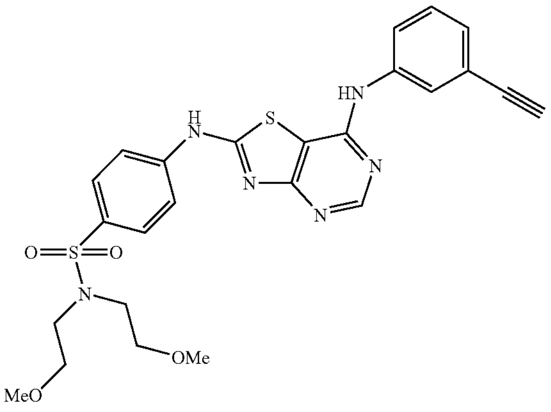
Cpd 34
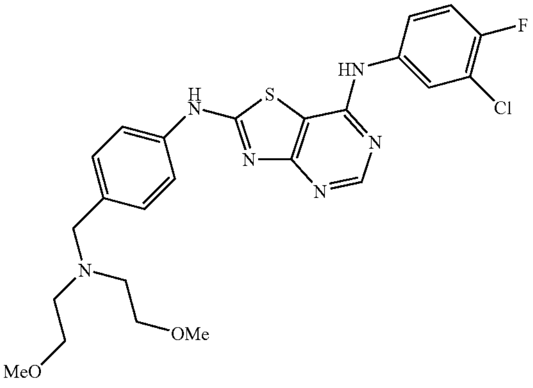
Cpd 35
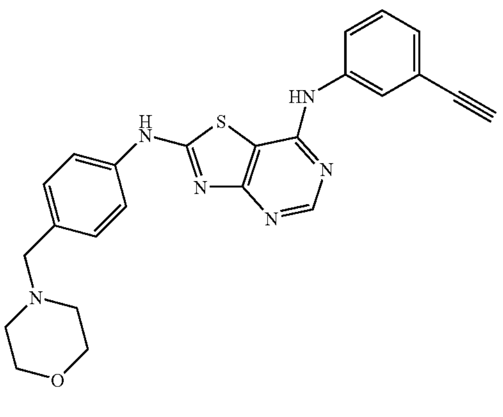

-continued
Cpd 36
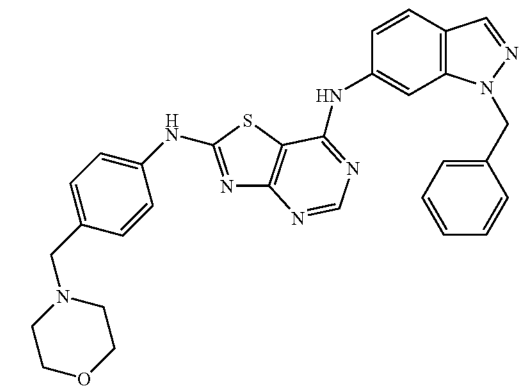
Cpd 37
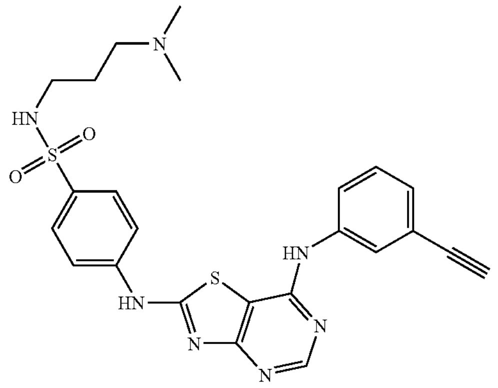
Cpd 38
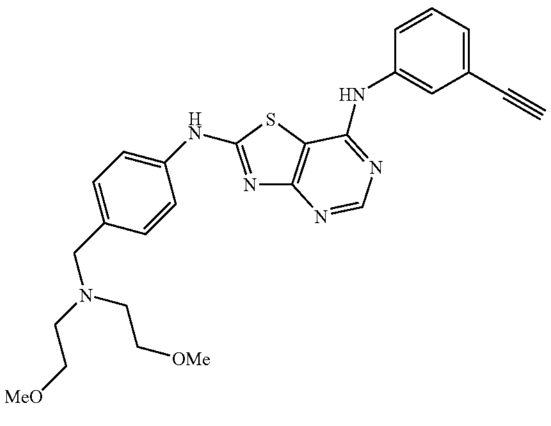
Cpd 39
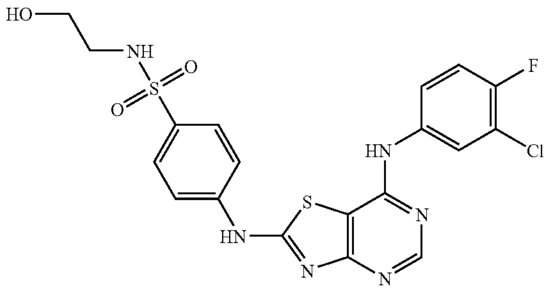
-continued
Cpd 40
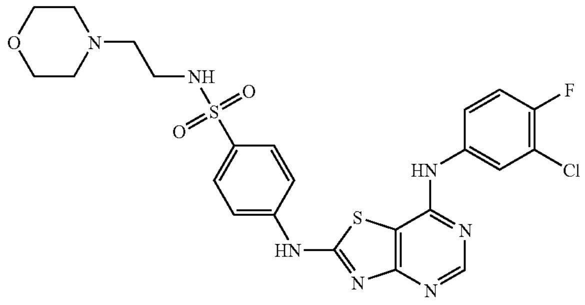
Cpd 41
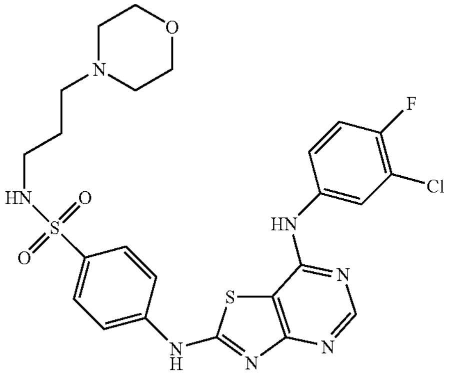
Cpd 42
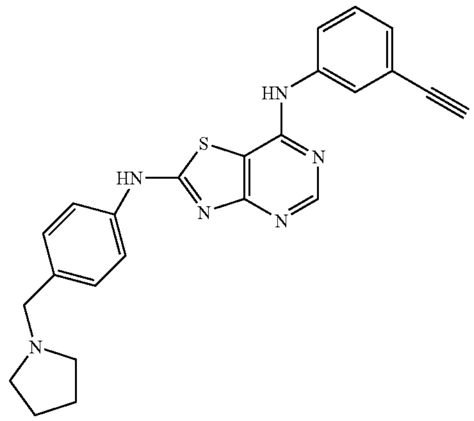
Cpd 43
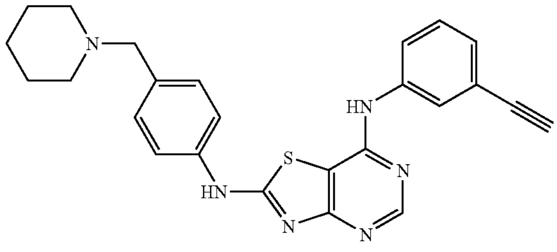

-continued
Cpd 44
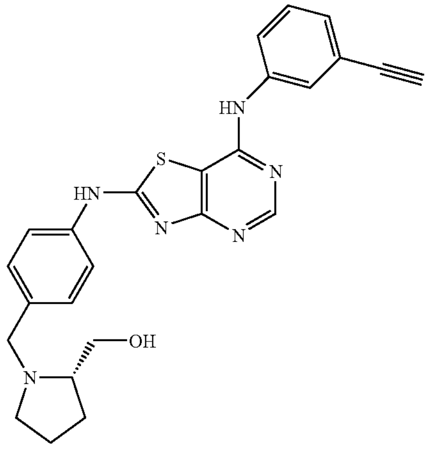
Cpd 45
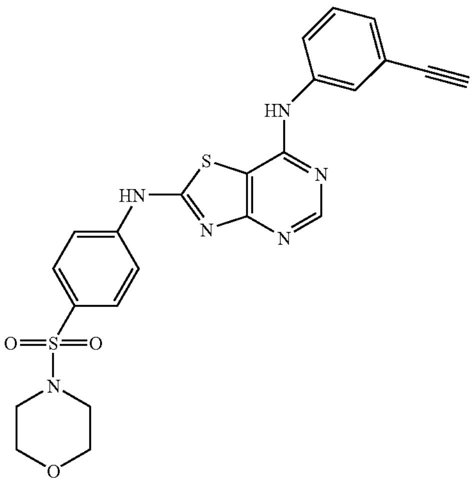
Cpd 46
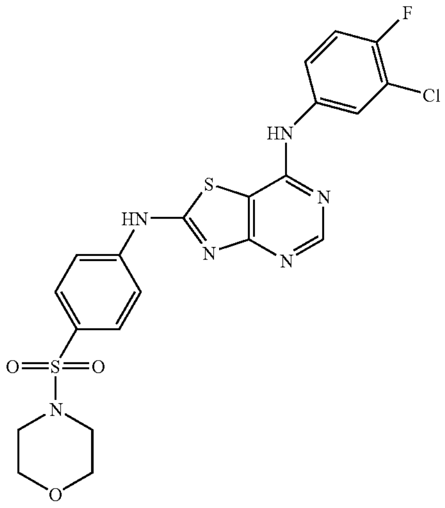
-continued
Cpd 47
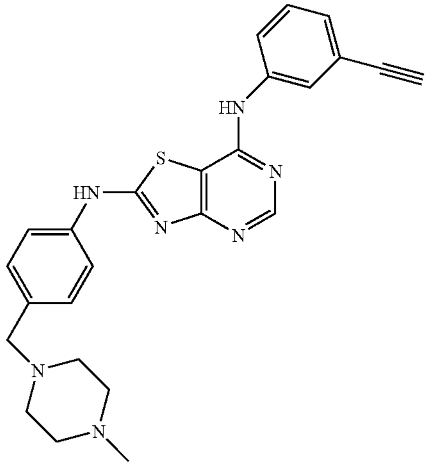
Cpd 48
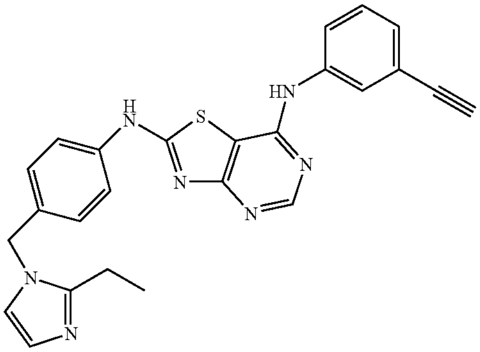
Cpd 49
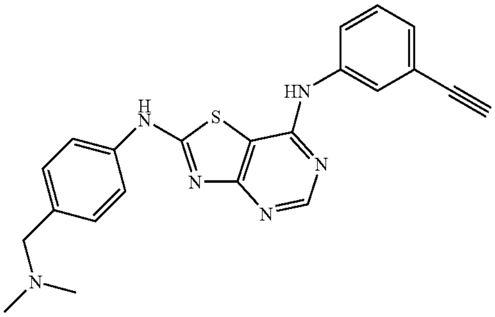
Cpd 50
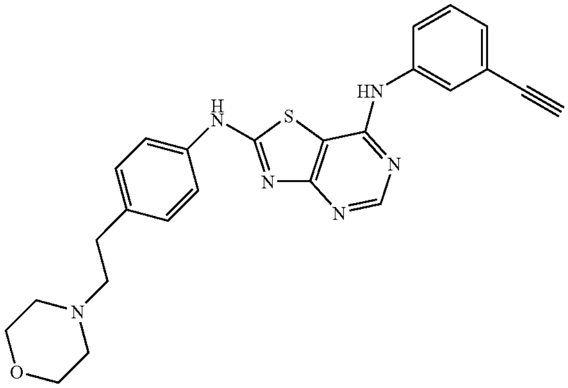

-continued
Cpd 51
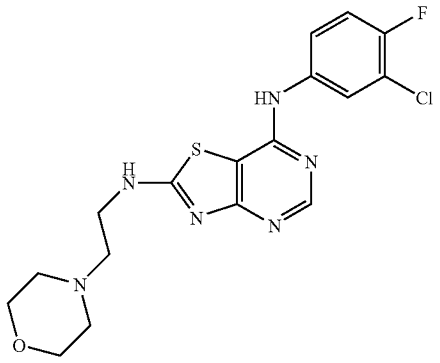
Cpd 52
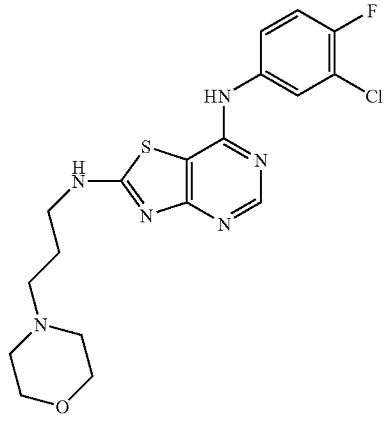
Cpd 53
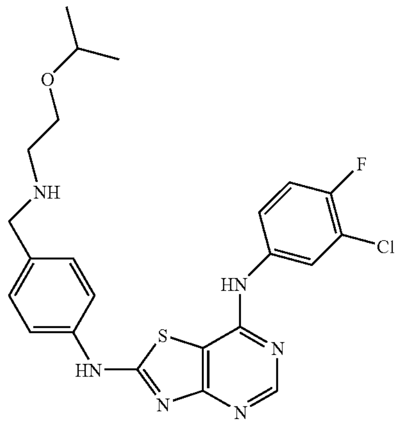
-continued
Cpd 54
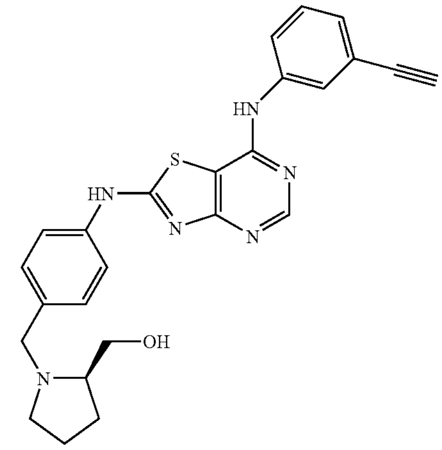
Cpd 55
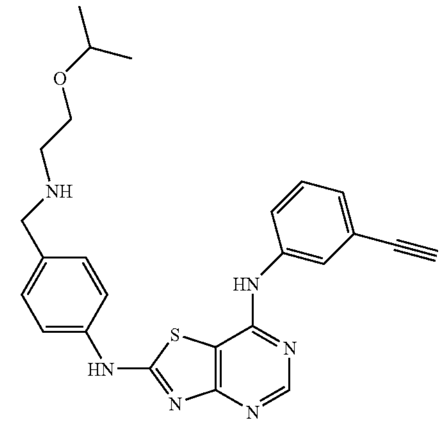
Cpd 56
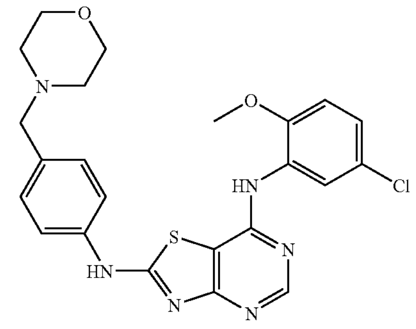
Cpd 57
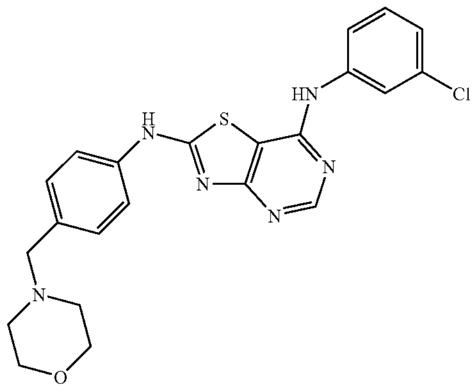

-continued
Cpd 58
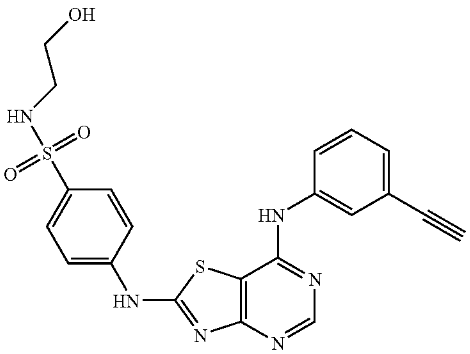
Cpd 59
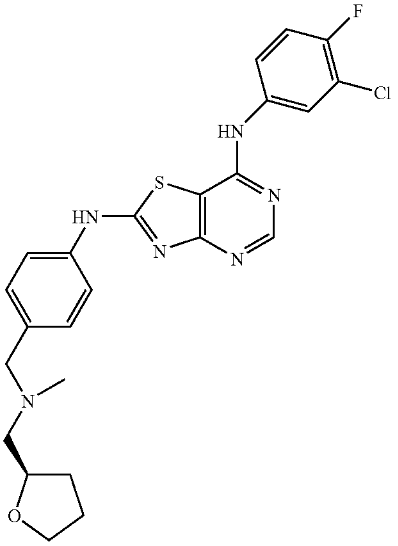
Cpd 60
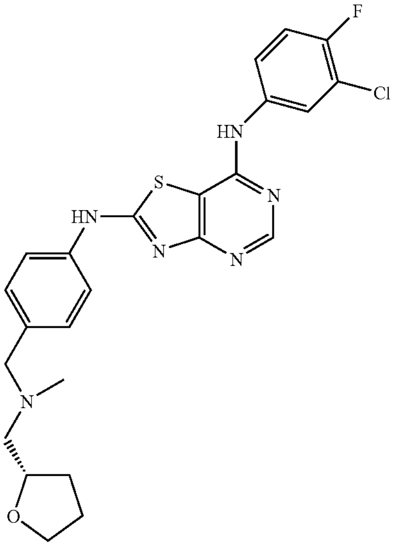
-continued
Cpd 61
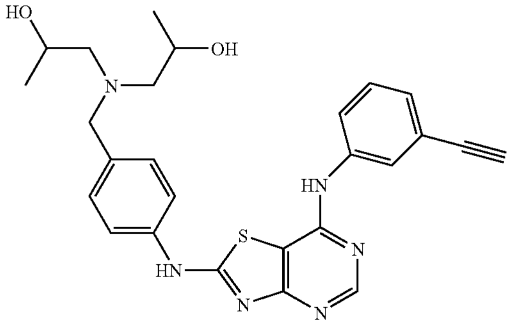
Cpd 62
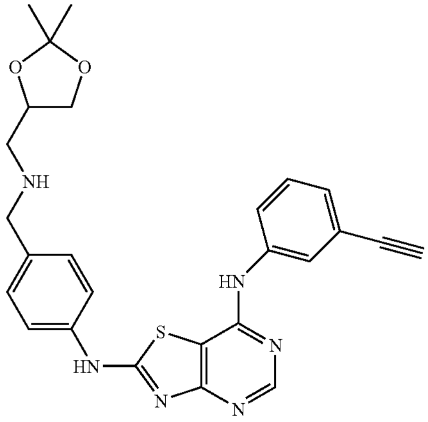
Cpd 63
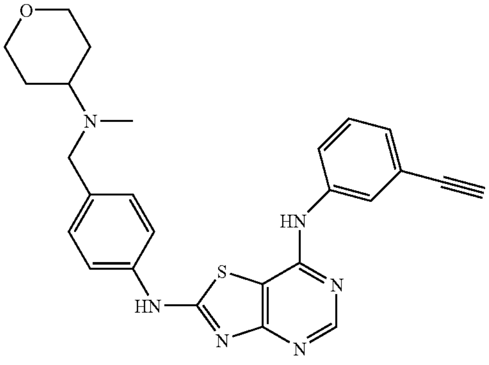

-continued
Cpd 64
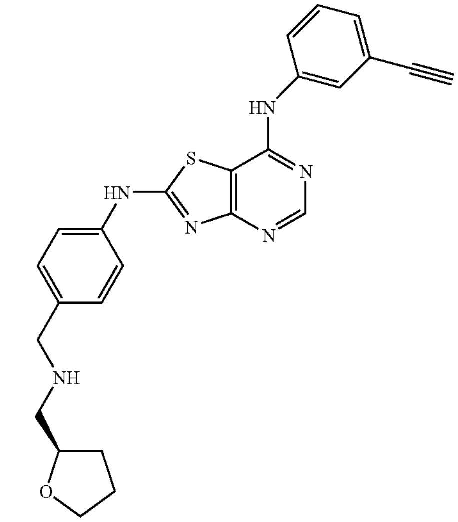
Cpd 65
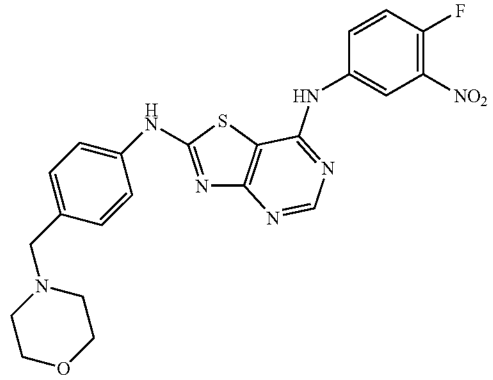
Cpd 66
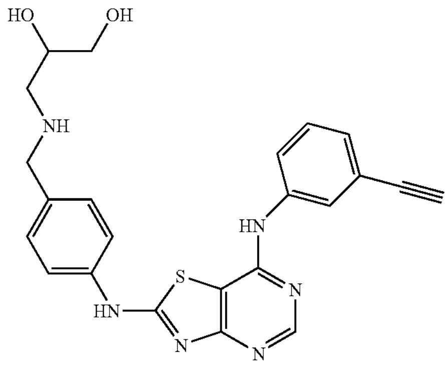
-continued
Cpd 67
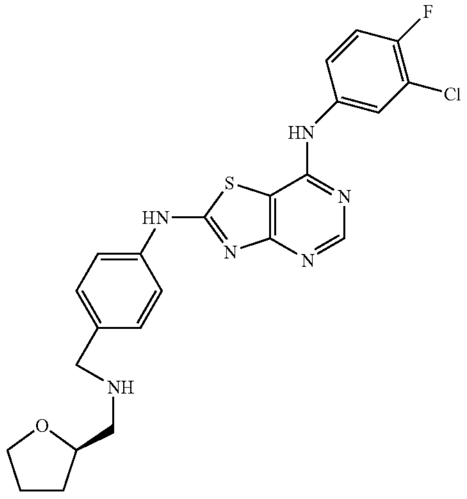
Cpd 68
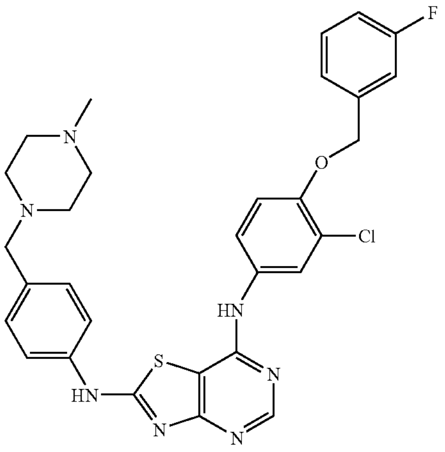
Cpd 69
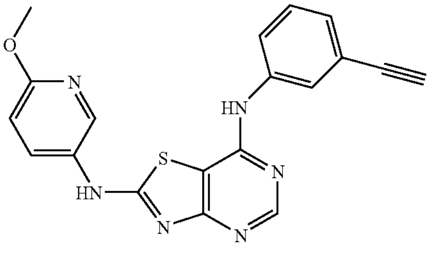
Cpd 70
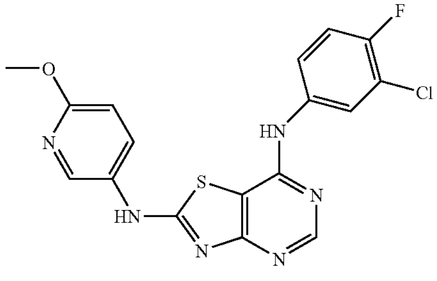

-continued
Cpd 71
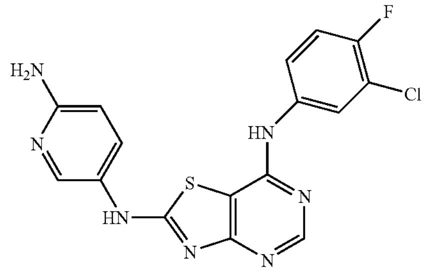
Cpd 72
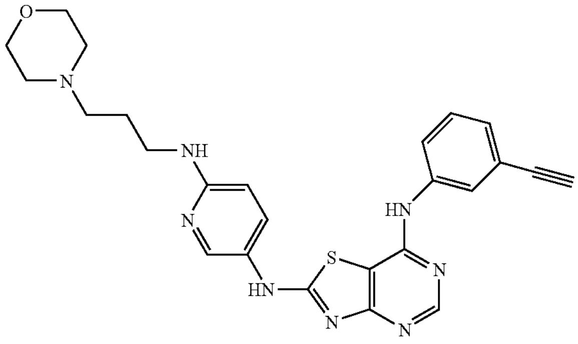
Cpd 73
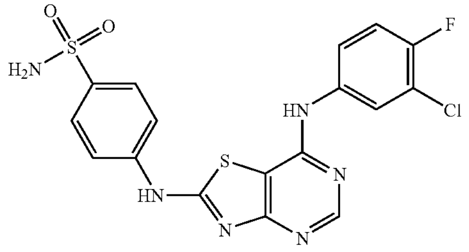
Cpd 74
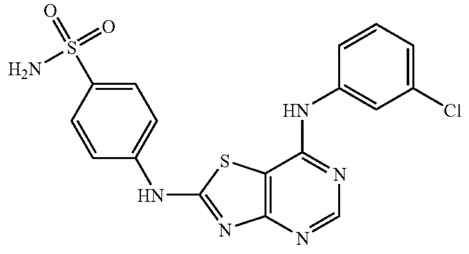
Cpd 75
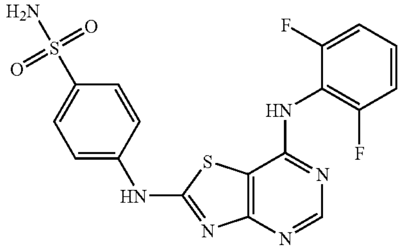
-continued
Cpd 76
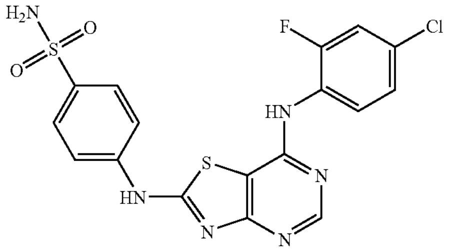
Cpd 77
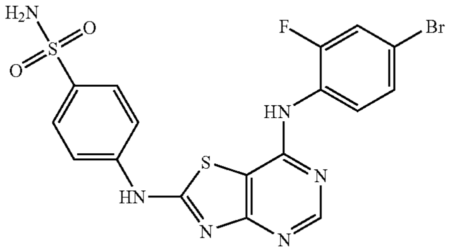
Cpd 78
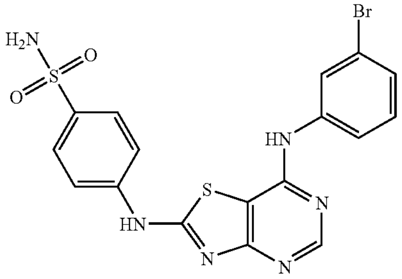
Cpd 79
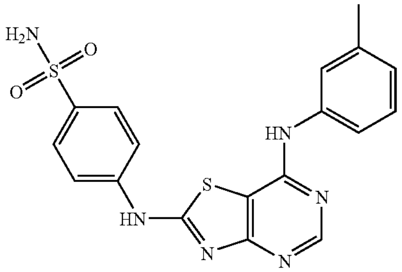
Cpd 80
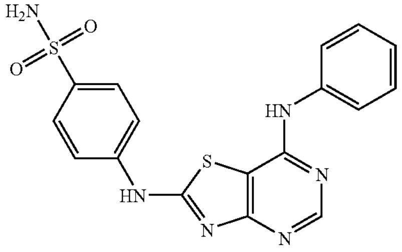
Cpd 81
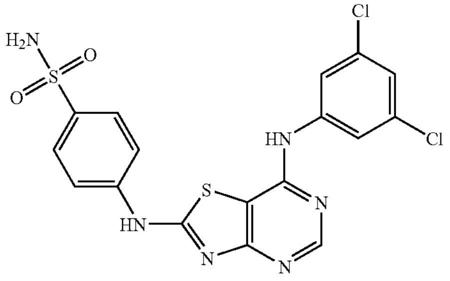

-continued
Cpd 82
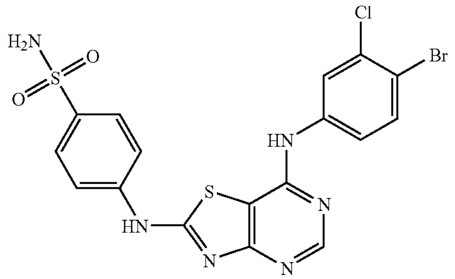
Cpd 83
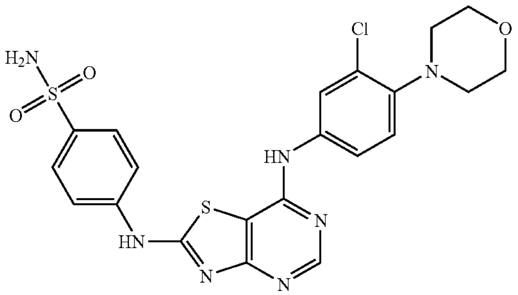
Cpd 84
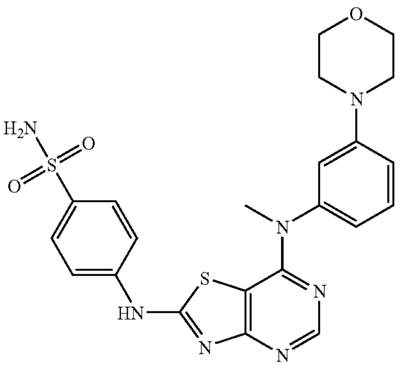
Cpd 85
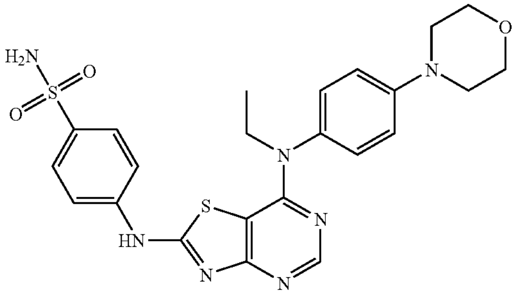
Cpd 86
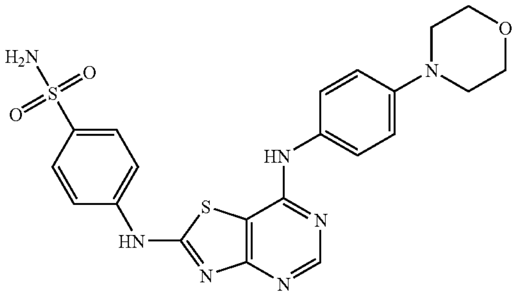
-continued
Cpd 87
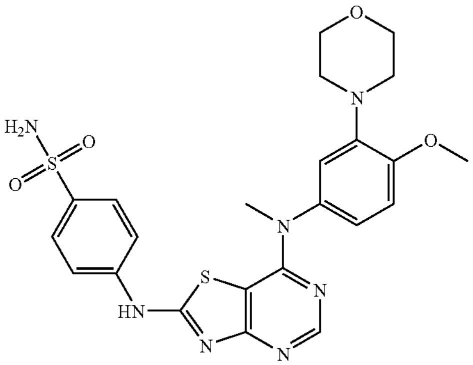
Cpd 88
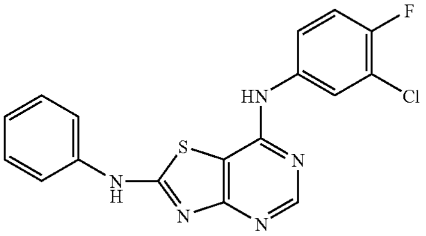
Cpd 89
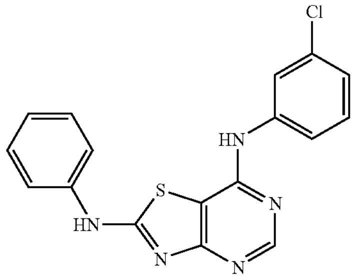
Cpd 90
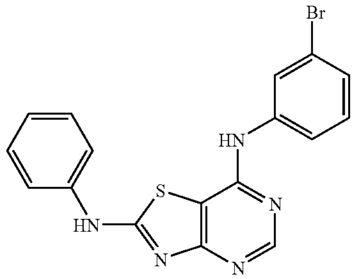
Cpd 91
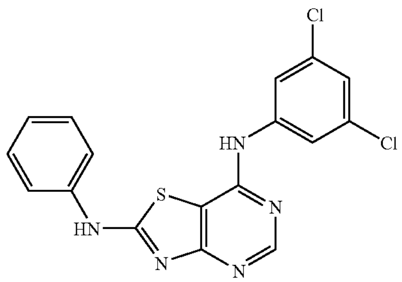

-continued

Cpd 92

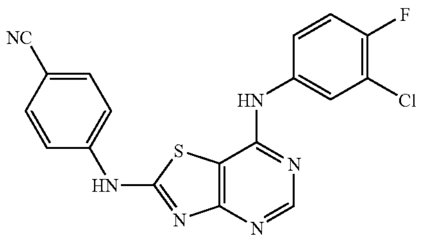

Cpd 93

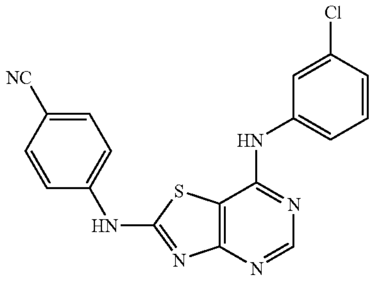

Cpd 94

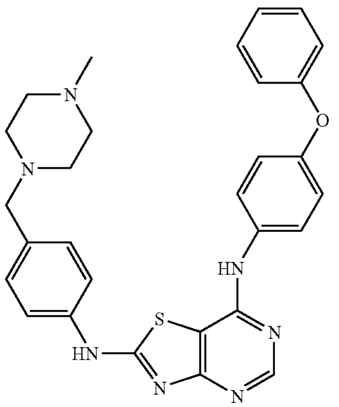

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

Examples of salt forms of compounds representative of the present invention include the monohydrochloride salt.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\%\ \text{levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\%\ \text{dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Chemical Definitions

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$ alkyl," whether used alone or as part of a substituent group, means a straight or branched chain monovalent hydrocarbon alkyl radical or alkyldiyl linking group comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain, such as, for example methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Examples include $C_{1-8}$alkyl, $C_{1-6}$alkyl and $C_{1-4}$alkyl groups.

The term "$C_{2-8}$ alkenyl," whether used alone or as part of a substituent group, means a straight or branched chain monovalent hydrocarbon alkyl or alkyldiyl radical radical having at least one carbon-carbon double bond, whereby the double bond is derived by the removal of one hydrogen atom from each of two adjacent carbon atoms of the alkyl radical. Atoms may be oriented about the double bond in either the cis (E) or trans (S) conformation. Typical alkenyl groups comprising from 2 to 8 carbon atoms, such as, for example, ethenyl, propenyl, allyl (2-propenyl), butenyl, pentenyl, hexenyl and the like. Examples include $C_{2-4}$alkenyl groups.

The term "$C_{2-8}$ alkynyl" whether used alone or as part of a substituent group, means a straight or branched chain monovalent hydrocarbon alkyl or alkyldiyl radical radical having at least one carbon-carbon triple bond, whereby the triple bond is derived by the removal of two hydrogen atoms from each of two adjacent carbon atoms of the alkyl radical. Typical alkynyl groups comprising from 2 to 8 carbon atoms, such as, for example, ethynyl, propynyl, butynyl, pentynyl, hexynyl and the like. Examples include $C_{2-4}$alkynyl groups.

The term "$C_{1-8}$ alkoxy," whether used alone or as part of a substituent group, refers to an alkyl or alkyldiyl radical attached through an oxygen linking atom. Typical alkoxy groups comprising from 1 to 8 carbon atoms, such as, for example, methoxy, ethoxy, propoxy, butoxy, pentoxy, hexoxy, heptoxy, octoxy and the like. An alkoxy radical may be attached to a core molecule and further substituted where indicated. Examples include $C_{1-8}$alkoxy or $C_{1-4}$alkoxy groups.

The term "$C_{3-12}$ cycloalkyl," whether used alone or as part of a substituent group, refers to a saturated or partially unsaturated, monocyclic or polycyclic hydrocarbon ring system radical derived by the removal of one hydrogen atom from a single ring carbon atom. Typical cycloalkyl radicals include cyclopropyl, cyclobutyl, cyclopentyl, cyclohexyl, cycloheptyl, cyclooctyl, 1H-indenyl, indanyl, tetrahydro-naphthalenyl and the like. Examples include $C_{3-8}$cycloalkyl, $C_{5-8}$cycloalkyl, $C_{3-10}$cycloalkyl and the like.

The term "heterocyclyl," whether used alone or as part of a substituent group, refers to a saturated or partially unsaturated monocyclic or polycyclic ring radical derived by the removal of one hydrogen atom from a single carbon or nitrogen ring atom. Typical heterocyclyl radicals include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like.

The term "hetero" used as a prefix for a ring system refers to the replacement of at least one ring carbon atom with one or more heteroatoms independently selected from N, S, or O. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein one heteroatom is nitrogen and the other is one heteroatom selected from N, S or O.

The term "aryl," whether used alone or as part of a substituent group, refers to an aromatic monocyclic or polycyclic hydrocarbon ring radical derived by the removal of one hydrogen atom from a single carbon atom of the ring system. Typical aryl radicals include phenyl, naphthalenyl, fluorenyl, azulenyl, anthracenyl and the like.

The term "aromatic" refers to a cycloalkylic hydrocarbon ring system having an unsaturated, conjugated $\pi$ electron system.

The term "heteroaryl," whether used alone or as part of a substituent group, refers to a heteroaromatic monocyclic or polycyclic hydrocarbon ring radical derived by the removal of one hydrogen atom from a single ring carbon atom of the ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, azaindolyl, isoindolyl, benzo[b]furyl, benzo[b]thienyl, indazolyl, azaindazolyl, benzimidazolyl, benzthiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "halogen" includes fluoro, chloro, bromo, and iodo.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

The term "independently selected" refers to one or more substituents selected from a group of substituents variable group, wherein the selected substituents may be the same or different.

The term "dependently selected" refers to one or more substituents specified in an indicated combination of structure variables.

Therapeutic Use

A first aspect of the present invention is compounds of Formula (I) or a form thereof useful as inhibitors of ATP-protein kinase interactions.

A second aspect of this invention is a composition or medicament comprising one or more compounds of Formula (I) or a form thereof.

A third aspect of this invention is the use of one or more compounds of Formula (I) or a form thereof as protein kinase inhibitors. The aspect of the protein kinases includes serine/threonine kinases and tyrosine kinases. The aspect of the kinases further includes kinase selected from EGFR, HER-2, c-Src, Lyn, c-Abl and the like. Also in this aspect, the compounds of Formula (I) or a form thereof are useful for preventing, treating or ameliorating chronic or acute kinase mediated diseases. The aspect of a kinase mediated disease includes an EGFR protein kinase mediated cytomegalovirus infection. In a related aspect, the compounds of Formula (I) or a form thereof are useful contraceptive agents.

The use of one or more compounds of Formula (I) or a form thereof as protein kinase inhibitors thus includes use of one or more compounds of Formula (I) or a form thereof for inhibiting unregulated protein kinase activity by contacting a protein kinase or protein kinase receptor with one or more compounds of Formula (I) or a form thereof. Accordingly, inhibiting such unregulated activity includes inhibiting unregulated expression or signaling and, thus, includes use of one or more compounds of Formula (I) or a form thereof for inhibiting unregulated cell proliferation.

A fourth aspect of this invention is a method for ameliorating, treating or preventing a chronic or acute kinase mediated disease in a patient in need thereof comprising administering to the patient an effective amount of one or more compounds of Formula (I) or a form thereof.

In this aspect, the chronic or acute disease is mediated by a kinase selected from EGFR, HER-2, c-Src, Lyn, c-Abl and the like. Also in this aspect, the method includes inhibiting unregulated kinase activity in the patient. The aspect of unregulated kinase activity includes unregulated kinase expression or signaling, unregulated expression or signaling of a kinase selected from EGFR, HER-2, c-Src, Lyn, c-Abl and the like and unregulated expression or signaling which results in unregulated cell proliferation. The aspect of unregulated cell proliferation includes cancer, metastatic cancer cell invasion or metastatic cancer cell migration. The aspect of cancer includes tumors mediated by the unregulated activity of kinases selected from EGFR, HER-2, c-Src, Lyn, c-Abl and the like. The aspect of cancer further includes non-small-cell lung cancers, colon cancers, breast cancers and the like. An aspect of the method includes an amount of one or more compounds of Formula (I) or a form thereof which is effective to induce remission of a chronic form of a cancer. The aspect of the effective amount includes an amount which is effective at a low dose to inhibit unregulated kinase activity.

A fifth aspect of this invention is a method for use of one or more compounds of Formula (I) or a form thereof in the preparation of a composition or medicament for preventing, treating or ameliorating chronic or acute kinase mediated diseases in a patient in need thereof. This aspect of the method includes administering to the patient an effective amount of a compound of Formula (I) or a form thereof in the form of a composition or medicament.

The term "chronic or acute kinase mediated disease" as used herein, includes, and is not limited to diseases, disorders, syndromes or conditions associated with unregulated kinase activity and diseases, disorders, syndromes or conditions that accompany such activity.

The term "unregulated kinase activity" refers to 1) increased or unregulated kinase expression or signaling, 2) increased kinase expression leading to unregulated cell proliferation, 3) increased kinase signaling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that the compounds of Formula (I) or a form thereof are useful for treating, preventing or ameliorating chronic or acute kinase mediated diseases such as, without limitation, osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus), heart disease (such as atherosclerosis, neointima formation or transplantation-induced vasculopathies (such as restenosis and the like)) lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like).

The term "administering" with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

Such methods include administering an effective amount of one or more compounds of Formula (I) or a form, composition or medicament thereof at different times during the course of a therapy or concurrently in a combination form. Such methods further include administering an effective amount of one or more compounds of Formula (I) or a form, composition or medicament thereof with one or more agents at different times during the course of a therapy or concurrently in a combination form.

The term "prodrug" refers to a metabolic precursor of a compound of Formula (I) or a form thereof. In general, a prodrug is a functional derivative of a compound which may be inactive when administered to a patient but is readily convertible in vivo into an active metabolite compound.

The term "active metabolite" refers to a metabolic product of a compound that is effective for preventing, treating or ameliorating a chronic or acute kinase mediated disease. Conventional procedures for the selection and preparation of suitable prodrug derivatives are described, for example, in "Design of Prodrugs", ed. H. Bundgaard, Elsevier, 1985.

The term "patient" as used herein, refers to an animal, preferably a mammal, most preferably a human, who has been the object of treatment, observation or experiment and is at risk of (or susceptible to) developing a disease or having a disease related to unregulated kinase activity.

The term "effective amount" refers to that amount of active compound or pharmaceutical agent that elicits the biological or medicinal response (such as inhibiting unregulated kinase activity) in a patient's tissue system, animal or human, that is being sought by a researcher, veterinarian, medical doctor, or other clinician, which includes preventing, treating or ameliorating the symptoms of the chronic or acute kinase mediated disease being treated.

The effective amount of a compound of Formula (I) exemplified in such a method is from about 0.001 mg/kg/day to about 300 mg/kg/day or has an $IC_{50}$ (50% inhibition concentration) of about 25 μM or less, or about 10 μM or less, preferably of about 1 μM or less, more preferably of about 0.5 μM or less, and most preferably of about 0.1 μM or less.

The term "composition" refers to a product containing one or more compounds of Formula (I) or a form thereof (such as a product comprising the specified ingredients in the specified amounts, as well as any product which results, directly or indirectly, from such combinations of the specified ingredients in the specified amounts).

The term "medicament" refers to one or more compounds of Formula (I) or a form thereof used in a product for use in preventing, treating or ameliorating a chronic or acute kinase mediated disease.

A formulation of a composition or medicament of the present invention is "pharmaceutically acceptable" when the molecular entities and components used therein are of sufficient purity and quality such that, when appropriately administered to an animal or a human, the formulation does not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination therapy" refers to the use of one or more compounds of Formula (I) or a form, composition or medicament thereof in combination with one or more therapeutic agents for preventing, treating or ameliorating a chronic or acute kinase mediated disease and advantageously may facilitate the use of a reduced effective dose of the compound of Formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The term "preventing, treating or ameliorating" refers, without limitation, to facilitating the eradication of, inhibiting the progression of or promoting stasis of a malignancy.

The term "radiation therapy" refers to a therapy that comprises exposing the patient in need thereof to radiation. The present invention includes a method for administering one or more compounds of Formula (I) or a form, composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

Pharmaceutical Compositions

An embodiment of the present invention includes a composition comprising an admixture of one or more compounds of Formula (I) and/or one or more forms thereof and one or more excipients.

The forms for a compound of Formula (I) include a salt, ester, prodrug or active metabolite of a compound of Formula (I). The form for a compound of Formula (I) further includes a radio-labeled compound of Formula (I), whereby at least one hydrogen atom of the compound of Formula (I) is replaced with a deuterium or tritium atom. Other labeling techniques known to those skilled in the arts may also be used.

The present invention further includes the use of a process for making the composition or medicament comprising mixing one or more of the instant compounds and an optional carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing one or more compounds of Formula (I) or a form, composition or medicament thereof as an active ingredient contains an effective amount of the active ingredient necessary to be therapeutically or prophylactically effective.

The composition or medicament may contain from about 0.001 mg to about 5000 mg (preferably, from about 0.001 to about 500 mg) of active ingredient and may be constituted into any form suitable for the mode of administration selected for a patient in need. A contemplated effective amount may range from about 0.001 mg to about 300 mg/kg of body weight per day. A contemplated effective amount may also range from about 0.003 to about 100 mg/kg of body weight per day. Another contemplated effective amount may range from about 0.1 to about 100 mg/kg of body weight per day. Another contemplated effective amount may also range from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A radio-labeled form of a compound of Formula (I), whereby at least one hydrogen atom of the compound of Formula (I) is replaced with a labeling atom such as a deuterium or tritium atom, may be used as a marker for the kinase receptor. Other labeling techniques known to those skilled in the arts may also be used.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations or formulas have the indicated meanings:

$H_2NCH_2CN$ amino-acetonitrile
Boc tert-butoxy carbonyl
CBz benzyl carbonyl
Cpd compound
$ClCH_2C(O)NH_2$ chloroacetamide
$ClCH_2C(O)OCH_3$, $ClCH_2CO_2Me$ or chloro-acetic acid methyl ester or methyl
$ClCH_2CO_2CH_3$ chloroacetate
$ClCH_2CN$ chloroacetonitrile
$NH_2CN$ cyanamide
DCM dichloromethane DIC 1,3-diisopropyl carbodiimide
DIBO di-t-butyl oxalate
DIPEA diisopropylethylamine
DMF N,N-dimethyl formamide
Et ethyl
EtOAc ethylacetate
CH(O)OH or $HCO_2H$ formic acid
$C(O)NH_2$ formamide
$HOCH_2CN$ hydroxy-acetonitrile
HOBt 1-hydroxybenzotriazole hydrate
LHMDS lithium hexamethyl disilazane
Me methyl
MCPBA 3-chloroperoxybenzoic acid
min/h/d/mp minute/hour/day(s)/melting point
Ph phenyl
$POCl_3$ phosphorus oxychloride
RT/rt/r.t. room temperature
MeONa sodium methoxide
$SOCl_2$ thionyl chloride
TEA or $Et_3N$ triethylamine
TFA trifluoroacetic acid
THF tetrahydrofuran Scheme A

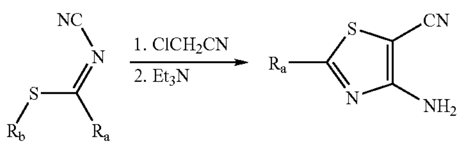

A1 A2

Chloroacetonitrile is reacted with a solution of a substituted cyanothioimidocarbonate Compound A1 (in a solvent such as acetone or ethanol and the like) in the presence of a base (such as TEA, pyridine, sodium ethoxide, DIPEA and the like) to provide a substituted 4-amino-thiazole-5-carbonitrile Compound A2.

$R_a$ is $C_{1-4}$alkyl, $C_{1-4}$alkoxy, thio-$C_{1-4}$alkyl or thio(potassium), wherein $C_{1-4}$alkyl is optionally substituted; and, $R_b$ is hydrogen, $C_{1-4}$alkyl or potassium, wherein $C_{1-4}$alkyl is optionally substituted. $R_a$ is other than thio(potassium) when $R_b$ is potassium; similarly, $R_b$ is other than potassium when $R_a$ is thio(potassium).

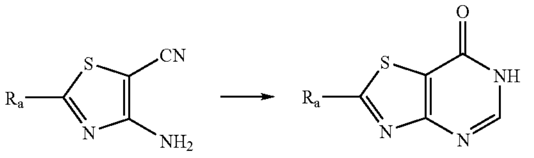

A2 A3

Compound A2 is refluxed in the presence of a reagent (such as formic acid, aqueous formic acid or formamide and the like) to provide a substituted 6H-thiazolo[4,5-d]pyrimidin-7-one Compound A3. (procedure adapted from Liebigs Ann. Chem., 1989, 409-412).

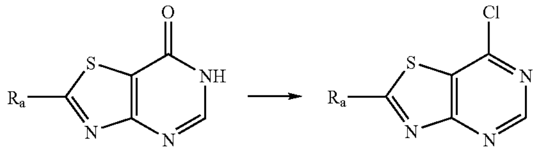

A3 A4

Compound A3 is taken up in a reagent (such as neat $POCl_3$ or $SOCl_2$) and refluxed to provide a substituted 7-chloro-6,7-dihydro-thiazolo[4,5-d]pyrimidine Compound A4.

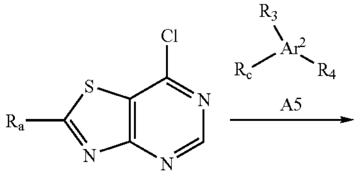

A4

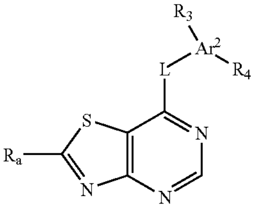

A6

A solution of Compound A4 (in a solvent such as 2-methoxyethyl ether, isopropanol, diglyme, butoxyethanol and the like) is reacted with a substituted ring system Compound A5 (wherein $R_c$ is a suitably substituted reactive group) to provide a substituted Compound A6.

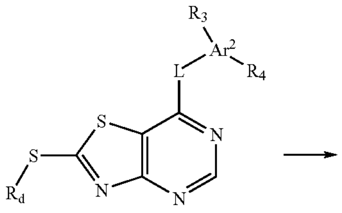

A6a

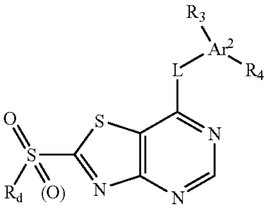

A7

Compound A6a (wherein $R_a$ for Compound A6 is S—$R_d$ and $R_d$ is $C_{1-4}$alkyl) is reacted with a suitable oxidizing agent (such as MCPBA, hydrogen peroxide and the like) in a solvent mixture (such as chloroform, methylene chloride and the like containing up to 25% ethanol and 10% saturated sodium bicarbonate and the like) to provide a sulfoxide or sulfone Compound A7.

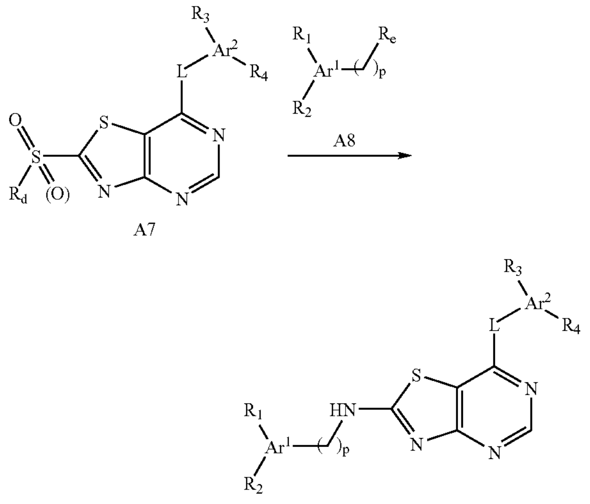

A7
(I)

Compound A7 is reacted with a substituted Compound A8 (wherein $R_e$ is a suitably substituted reactive group) in an acidic media (using an acid such as acetic acid and the like) to provide a compound of Formula (I).

Scheme B

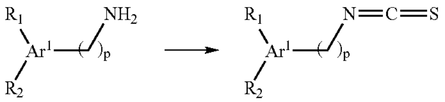
B1 B2

An aqueous solution of a Compound B1, in the presence of an acid (such as concentrated hydrochloric acid and the like), is reacted with thiophosgene to provide a Compound B2.

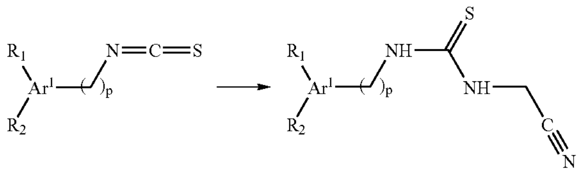
B2 B3

A suspension or solution of Compound B2 and $NH_2CN$ (in a suitable solvent such as methanol and the like) is reacted in the presence of a base (such as MeONa and the like in a solvent such as methanol and the like) to provide a Compound B3.

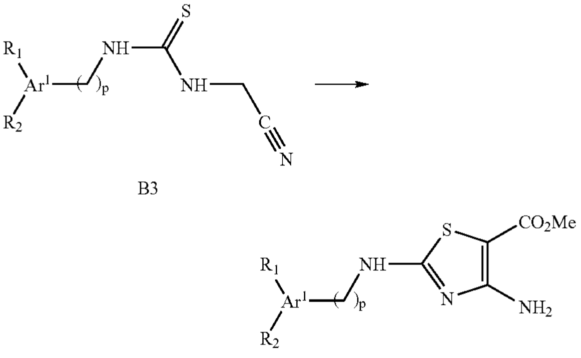
B3
B4

Methyl chloroacetate at about r.t. is added to the Compound B3 mixture and reacted to provide a Compound B4.

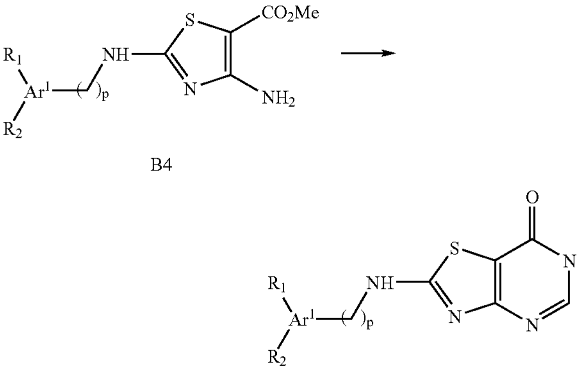
B4
B5

Acetic anhydride is added to a suspension of Compound B4 in formamide and reacted to provide a Compound B5.

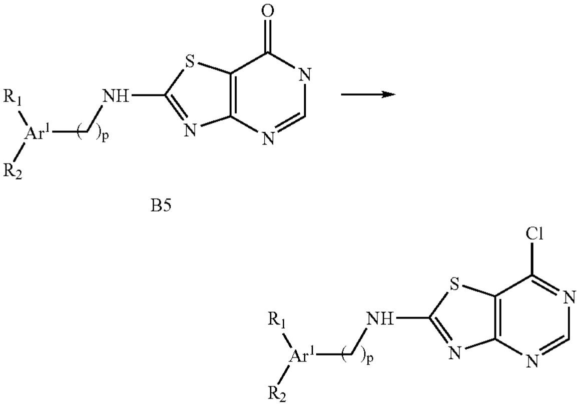
B5
B6

A chlorination reagent (such as $POCl_3$ and the like) is added dropwise to a solution of Compound B5 (in a solvent such as HMPA and the like) and reacted to provide a Compound B6.

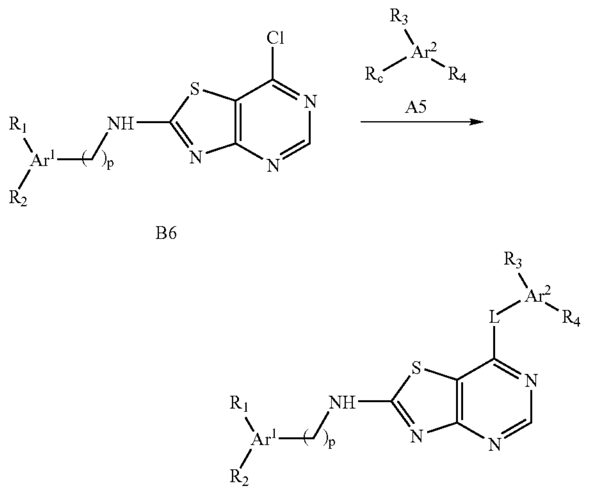

B6

(I)

A suspension or solution of Compound B6 is reacted with a solution of a Compound A5 (in a solvent such as isopropanol, diglyme, butoxyethanol and the like) to provide a compound of Formula (I).

EXAMPLE 1

$N^7$-(3-ethynyl-phenyl)-$N^2$-(4-piperidin-1-ylmethyl-phenyl)-thiazolo[4,5-d]pyrimidine-2,7-diamine (Cpd 43)

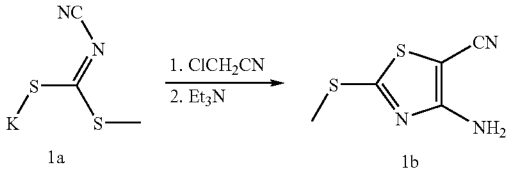

1a 1b

Chloroacetonitrile (21.1 ml, 333 mmol) was added to a solution of potassium methyl N-cyanodithioimidocarbonate Compound 1a (51.6 g, 303 mmol) at 0° C. in acetone (500 mL). After stirring for 1 hr at ambient temperature, triethylamine (12.7 ml, 90.9 mmol) was added to the reaction mixture. The reaction was stirred for 72 hrs. 4-amino-2-methylsulfanyl-thiazole-5-carbonitrile Compound 1b (52 g) was collected by filtration then sequentially rinsed with water and methylene chloride. $^1H$ NMR ($DMSOd_6$) δ 7.21 (br s, 2H), 2.67 (s, 3H). MS 172 ($MH^+$).

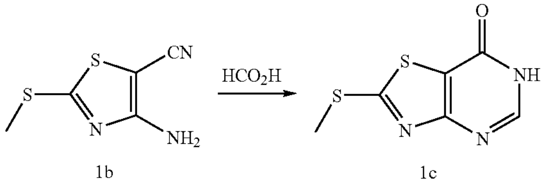

1b 1c

Compound 1b (78.5 g, 460 mmol), formic acid (290 ml) and water (15 ml) were combined and heated to reflux for 4 hrs. The mixture was allowed to stand at r.t. A precipitate formed and was collected by filtration, then sequentially rinsed with water and acetone to provide 2-methylsulfanyl-6H-thiazolo[4,5-d]pyrimidin-7-one Compound 1c (65.1 g) as an orange solid (procedure adapted from Liebigs Ann. Chem., 1989, 409-412).

$^1H$ NMR ($DMSOd_6$) δ 8.27 (s, 1H), 8.15 (s, 1H), 2.81 (s, 3H). MS 200 ($MH^+$).

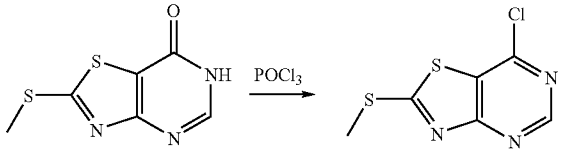

1c 1d

Compound 1c (72.3 g, 363 mmol) was refluxed in $POCl_3$ (200 ml) for a period of 1 hr. The mixture was cooled to ambient temperature, then slowly added to ice. The precipitate was collected by filtration to provide 7-chloro-2-methylsulfanyl-thiazolo[4,5-d]pyrimidine Compound 1d as a HCl salt (85 g). $^1H$ NMR ($CDCl_3$) δ 8.97 (s, 1H), 2.91 (s, 3H). MS 218 ($MH^+$).

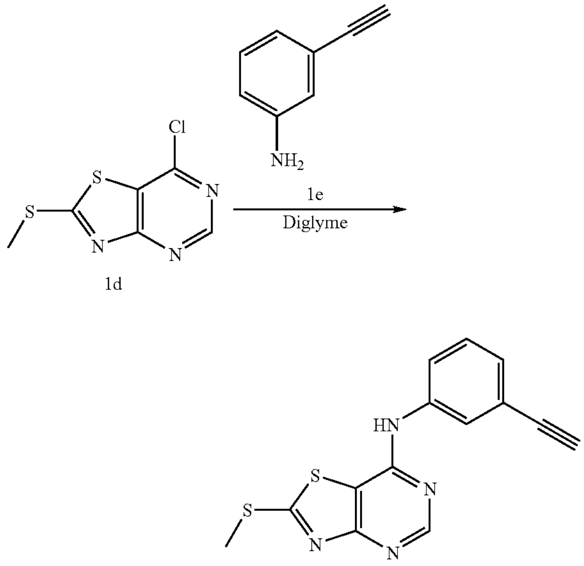

1d

1f

Compound 1d (48.8 g, 193 mmol) and 3-ethynyl-phenylamine Compound 1e (22.6 g, 193 mmol) were heated to 140° C. in diglyme (500 ml) for 3 hrs then cooled to 0° C. The precipitate was collected by filtration and rinsed with water to provide (3-ethynyl-phenyl)-(2-methylsulfanyl-thiazolo[4,5-d]pyrimidin-7-yl)-amine Compound 1f as a HCl salt (60 g). $^1H$ NMR ($DMSOd_6$) δ 10.06 (s, 1H), 8.67 (s, 1H), 7.97 (t, J=2.0 Hz, 1H), 7.77 (ddd, J=8.0, 2.0, 1.3 Hz, 1H), 7.42 (t, J=8.0 Hz, 1H), 7.25 (dt, J=8.0, 1.3 Hz, 1H), 4.20 (s, 1H), 2.85 (s, 3H). MS 299 ($MH^+$).

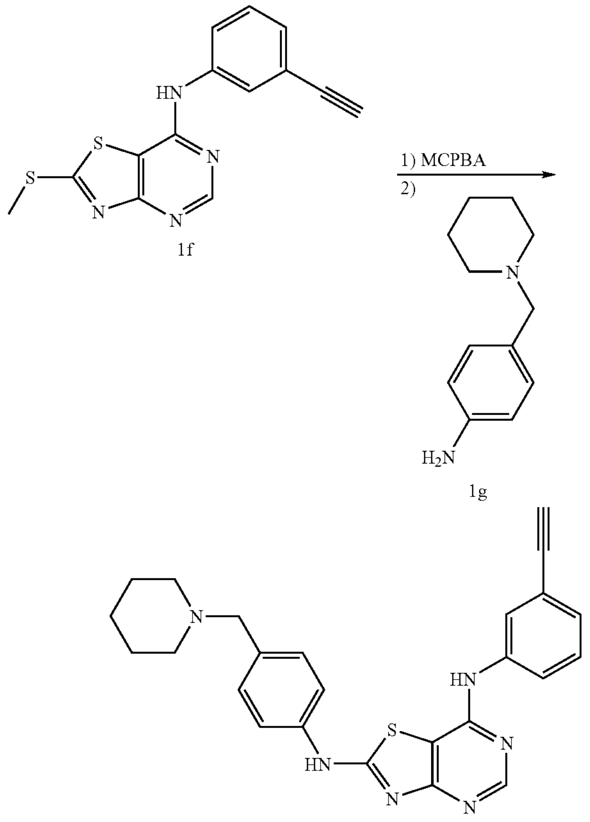

1f

1g

Cpd 43

Compound 1f (2.0 g, 6.0 mmol) was dissolved in a mixture of DCM (45 ml), MeOH (3 ml) and saturated $NaHCO_3$ (5 ml). MCPBA (77%, 3.09 g, 13.8 mmol) was added to the mixture chilled in an ice bath (~5 C) and stirred for 2 hrs. The reaction mixture was diluted with saturated $NaHCO_3$ and extracted with DCM. The organic layers were combined, dried over $MgSO_4$ and evaporated in vacuo. The resultant residue was dissolved in AcOH (45 ml) and 4-piperidin-1-ylmethyl-phenylamine Compound 1g (850 mg, 4.47 mmol) in AcOH (5 ml) was added. The mixture was heated to 40° C. for 4 hrs, then diluted with water and extracted with EtOAc. The combined organic layers were dried over $MgSO_4$ and evaporated in vacuo. The residue was dissolved in MeOH and treated with 2M HCl-ether (excess). The precipitate was collected by filtration and rinsed with water to provide Compound 43 as a HCl salt (356 mg). $^1$H-NMR (DMSOd$_6$) δ 11.33 (br s, 1H); 9.74 (s, 1H); 9.45 (br s, 1H); 8.56 (s, 1H); 7.89-7.86 (m, 3H); 7.71 (d, J=7.6 Hz, 1H); 7.54 (d, J=8.8 Hz, 2H); 7.39 (t, J=7.6 Hz, 1H); 7.22 (d, J=7.6, 1H); 4.27 (s, 2H); 4.21 (s, 1H); 3.36-3.33 (m, 2H); 2.97-2.82 (m, 2H); 1.85-1.81 (m, 2H); 1.61-1.57 (m, 2H); 1.42-1.34 (m, 2H). MS 441 (MH$^+$).

Using the procedure of Example 1 and varying the starting materials, reagent(s) and conditions used, those skilled in the art may prepare other representative compounds of the present invention including, but not limited to:

N$^7$-(3-chloro-4-fluoro-phenyl)-N$^2$-(4-morpholin-4-yl-phenyl)-thiazolo[4,5-d]pyrimidine-2,7-diamine (Cpd 1)

4-morpholin-4-yl-phenylamine was used in place of Compound 1g and Compound 2g was used in place of Compound 1e. Isolated as a trifluoroacetate salt. $^1$H NMR (DMSO-d$_6$) δ 11.11 (br s, 1H); 9.97 (br s, 1H); 8.60 (s, 1H); 8.01 (dd, J=6.8, 2.6 Hz, 1H); 7.68-7.54 (m, 3H); 7.46 (t, J=9.0 Hz, 1H); 7.05 (d, J=8.8 Hz, 2H); 3.83-3.74 (m, 4H); 3.19-3.10 (m, 4H). MS 457, 459 (MH$^+$).

N$^7$-(3-chloro-4-fluoro-phenyl)-N$^2$-(4-piperidin-1-ylmethyl-phenyl)-thiazolo[4,5-d]pyrimidine-2,7-diamine (Cpd 2)

Compound 2g was used in place of Compound 1e. Isolated as a trifluoroacetate salt. $^1$H NMR (DMSO-d$_6$) δ 11.27 (s, 1H); 9.69 (s, 1H); 9.32 (br s, 1H); 8.56 (s, 1H); 8.07 (dd, J=6.8 Hz, 2.6 Hz, 1H); 7.91 (d, J=8.5 Hz, 2H); 7.69 (ddd, J=9.0 Hz, 4.3 Hz, 2.6 Hz, 1H); 7.57 (d, 8.5 Hz, 2H); 7.46 (t, 9.0 Hz, 1H); 4.30 (s, 2H); 3.37 (d, J=12.4 Hz, 2H); 2.96-2.86 (m, 2H); 1.86 (d, 12.4 Hz, 2H); 1.71-1.59 (m, 3H); 1.41-1.36 (m, 1H). MS 469, 471(MH$^+$).

N$^7$-(3-chloro-4-fluoro-phenyl)-N$^2$-(3-morpholin-4-ylmethyl-phenyl)-thiazolo[4,5-d]pyrimidine-2,7-diamine (Cpd 3)

3-morpholin-4-ylmethyl-phenylamine was used in place of Compound 1g and Compound 2g was used in place of Compound 1e. Isolated as a trifluoroacetate salt. MS 471, 473 (MH$^+$).

N$^7$-(3-chloro-4-fluoro-phenyl)-N$^2$-[4-(2-morpholin-4-yl-ethyl)-phenyl]-thiazolo[4,5-d]pyrimidine-2,7-diamine (Cpd 4)

4-(2-morpholin-4-yl-ethyl)-phenylamine was used in place of Compound 1g and Compound 2g was used in place of Compound 1e. Isolated as a trifluoroacetate salt. $^1$H NMR (DMSO-d$_6$) δ 11.10 (s, 1H); 9.84 (br s, 1H); 9.66 (s, 1H); 8.53 (s, 1H); 8.04 (dd, J=6.7, 2.4 Hz, 1H); 7.77 (d, J=8.4 Hz, 2H); 7.69-7.63 (m, 1H); 7.43 (t, J=9.1 Hz, 1H); 7.35 (d, J=8.4 Hz, 2H); 4.04 (d, J=11.8 Hz, 2H); 3.73-3.61 (m, 2H); 3.47-3.33 (m, 4H); 3.21-3.08 (m, 2H); 3.04-2.96 (m, 2H). MS 485, 487 (MH$^+$).

N$^7$-(3-chloro-4-fluoro-phenyl)-N$^2$-[4-(4-methyl-piperazin-1-ylmethyl)-phenyl]-thiazolo[4,5-d]pyrimidine-2,7-diamine (Cpd 5)

4-(4-methyl-piperazin-1-ylmethyl)-phenylamine was used in place of Compound 1g and Compound 2g was used in place of Compound 1e. Isolated as a trifluoroacetate salt. $^1$H NMR (DMSO-d$_6$) δ 11.14 (s, 1H); 9.67 (s, 1H); 8.55 (s, 1H); 8.06 (dd, J=6.8 Hz, 2.8 Hz, 1H); 7.81 (d, J=7.7 Hz, 2H); 7.68 (ddd, J=9.1 Hz, 4.2 Hz, 2.8 Hz, 1H); 7.49-7.42 (m, 3H); 4.35 (s, 2H); 3.75-3.71 (m, 2H); 3.44-3.41 (m, 2H); 3.07-3.04 (m, 2H); 2.81 (s, 3H); 2.42-2.41 (m, 2H). MS 484, 486 (MH$^+$).

N$^7$-(3-chloro-4-fluoro-phenyl)-N$^2$-(3-methoxy4-piperidin-1-ylmethyl-phenyl)-thiazolo[4,5-d]pyrimidine-2,7-diamine (Cpd 6)

3-methoxy-4-piperidin-1-ylmethyl-phenylamine was used in place of Compound 1g and Compound 2g was used in place of Compound 1e. Isolated as a trifluoroacetate salt. $^1$H NMR (DMSO-d$_6$) δ 11.28 (s, 1H); 9.67 (s, 1H); 9.03 (br s, 1H); 8.54 (s, 1H); 8.06 (dd, J=6.6, 2.6 Hz, 1H); 7.69-7.64 (m, 1H); 7.58 (s, 1H); 7.49 (s, 2H); 7.44 (t, J=9.2 Hz, 1H); 4.22 (s, 2H); 3.90 (s, 3H); 3.37-3.23 (m, 2H); 2.98-2.86 (m, 2H); 1.87-1.76 (m, 2H); 1.73-1.58 (m, 3H); 1.46-1.32 (m, 1H). MS 499, 501 (MH$^+$).

N$^7$-(3-chloro-phenyl)-N$^2$-[4-(2-ethyl-imidazol-1-ylmethyl)-phenyl]-thiazolo[4,5-d]pyrimidine-2,7-diamine (Cpd 7)

4-(2-ethyl-imidazol-1-ylmethyl)-phenylamine was used in place of Compound lg and 3-chloro-phenylamine was used in place of Compound 1e. Isolated as a trifluoroacetate salt. $^1$H NMR (DMSO-$d_6$) δ 9.88 (br s, 1H); 9.68 (s, 1H); 8.54 (s, 1H); 7.93 (s, 1H); 7.82 (d, J=8.6 Hz, 2H); 7.76-7.61 (m, 3H); 7.48-7.37 (m, 3H); 7.14 (d, J=7.8 Hz, 1H); 5.42 (s, 2H); 3.00 (q, J=7.7 Hz, 2H); 1.22 (t, J=7.7 Hz, 3H). MS 462, 464 (MH$^+$).

N$^7$-(3-chloro-phenyl)-N$^2$-(3-piperidin-1-ylmethyl-phenyl)-thiazolo[4,5-d]pyrimidine-2,7-diamine (Cpd 8)

3-piperidin-1-ylmethyl-phenylamine was used in place of Compound 1g and 3-chloro-phenylamine was used in place of Compound 1e. Isolated as a trifluoroacetate salt. $^1$H NMR (DMSO-$d_6$) δ 11.21 (s, 1H); 9.65 (s, 1H); 9.37 (br s, 1H); 8.55 (s, 1H); 7.98-7.92 (m, 2H); 7.80 (d, J=8.0 Hz, 1H); 7.65 (dd, J=8.0, 1.9 Hz, 1H); 7.53 (t, J=8.0 Hz, 1H); 7.38 (t, J=8.0 Hz, 1H); 7.25 (d, J=8.0 Hz, 1H); 7.13 (dd, J=8.0, 1.9 Hz, 1H); 4.34 (s, 2H); 3.03-2.88 (m, 2H); 1.89-1.78 (m, 2H), 1.74-1.57(m, 3H); 1.44-1.30 (m, 1H). MS 451, 453 (MH$^+$).

N$^7$-(3-chloro-phenyl)-N$^2$-(4-pyridin-4-ylmethyl-phenyl)-thiazolo[4,5-d]pyrimidine-2,7-diamine (Cpd 9)

4-pyridin4-ylmethyl-phenylamine was used in place of Compound 1g and 3-chloro-phenylamine was used in place of Compound 1e. Isolated as a trifluoroacetate salt. $^1$H NMR (DMSO-$d_6$) δ 11.13 (br s, 1H); 9.80 (s, 1H); 8.70 (br s, 2H); 8.53 (s, 1H); 7.91 (s, 1H); 7.78-7.59 (m, 5H); 7.41-7.28 (m, 3H); 7.12 (d, J=7.8 Hz, 1H); 4.19 (s, 2H). MS 445, 447 (MH$^+$).

N$^7$-(3-chloro-4-fluoro-phenyl)-N$^2$-(4-dimethylaminomethyl-phenyl)-thiazolo[4,5-d]pyrimidine-2,7-diamine (Cpd 10)

4-dimethylaminomethyl-phenylamine was used in place of Compound 1g and Compound 2g was used in place of Compound 1e. Isolated as a trifluoroacetate salt. $^1$H NMR ($CDCl_3$) δ 8.60 (s, 1H); 7.56 (dd, J=6.7, 2.6 Hz, 1H); 7.47 (d, J=8.4 Hz, 2H); 7.36 (d, J=8.4 Hz, 2H); 7.32-7.24 (m, 1H), 7.15 (t, J=9.0 Hz, 1H); 6.58 (br s, 1H); 3.42 (s, 2H); 2.28 (s, 6H). MS 429, 431 (MH$^+$).

N$^7$-(3-chloro4-fluoro-phenyl)-N$^2$-[4-(2-dimethylamino-ethyl)-phenyl]-thiazolo[4,5-d]pyrimidine-2,7-diamine (Cpd 11)

4-(2-dimethylamino-ethyl)-phenylamine was used in place of Compound 1g and Compound 2g was used in place of Compound 1e. Isolated as a trifluoroacetate salt. MS 443, 445 (MH$^+$).

N$^7$-(3-chloro4-fluoro-phenyl)-N$^2$-(4-methoxy-phenyl)-thiazolo[4,5-d]pyrimidine-2,7-diamine (Cpd 12)

4-methoxy-phenylamine was used in place of Compound 1g and Compound 2g was used in place of Compound 1e. Isolated as a trifluoroacetate salt. $^1$H NMR (DMSO-$d_6$) δ 9.35 (br s, 1H); 8.52 (s, 1H); 7.82 (dd, J=6.6 Hz, 2.6 Hz, 1H); 7.62 (d, J=9.1 Hz, 2H); 7.46 (ddd, J=8.9 Hz, 4.2 Hz, 2.6 Hz, 1H); 7.14 (t, J=8.9 Hz, 1H); 6.91 (d, J=9.1 Hz, 2H); 3.82 (s, 3H). MS 402, 404 (MH$^+$).

4-[7-(3-chloro4-fluoro-phenylamino)-thiazolo[4,5-d]pyrimidin-2-ylamino]-phenol (Cpd 13)

4-amino-phenol was used in place of Compound 1g and Compound 2g was used in place of Compound 1e. Isolated as a trifluoroacetate salt. $^1$H NMR (DMSO-$d_6$) δ 10.98 (br s, 1H); 9.90 (s, 1H); 8.52 (s, 1H); 7.93 (dd, J=6.7 Hz, 2.7 Hz, 1H); 7.55 (ddd, 8.8 Hz, 4.4 Hz, 2.7 Hz, 1H); 7.44-7.35 (m, 3H); 6.78 (d, J=8.7 Hz, 2H). MS 388, 390 (MH$^+$).

N$^7$-(3-chloro-4-fluoro-phenyl)-N$^2$-[4-(2-morpholin-4-yl-ethoxy)-phenyl]-thiazolo[4,5-d]pyrimidine-2,7-diamine (Cpd 14)

4-(2-morpholin-4-yl-ethoxy)-phenylamine was used in place of Compound 1g and Compound 2g was used in place of Compound 1e. Isolated as a trifluoroacetate salt. $^1$H NMR (DMSO-$d_6$) δ 10.98 (s, 1H); 9.97 (br s, 1H); 9.61 (br s, 1H); 8.51 (s, 1H); 8.04 (dd, J=6.8 Hz, 2.8 Hz, 1H); 7.73 (d, J=9.0 Hz, 2H); 7.65 (ddd, J=9.1 Hz, 4.3 Hz, 2.8 Hz, 1H); 7.42 (t, J=9.1 Hz, 1H); 7.10 (d, J=9.0 Hz, 2H); 4.37 (t, J=4.8 Hz, 2H); 4.02-3.99 (m, 2H); 3.82-3.47 (m, 6H); 3.23-3.15 (m, 2H). MS 501, 503 (MH$^+$).

N$^7$-(3-chloro-4-fluoro-phenyl)-N$^2$-[4-(2-pyrrolidin-1-yl-ethoxy)-phenyl]-thiazolo[4,5-d]pyrimidine-2,7-diamine (Cpd 15)

4-(2-pyrrolidin-1-yl-ethoxy)-phenylamine was used in place of Compound 1g and Compound 2g was used in place of Compound 1e. Isolated as a trifluoroacetate salt. $^1$H NMR (DMSOA$_6$) δ 10.96 (s, 1H); 9.74 (s, 1H); 8.49 (s, 1H); 7.94 (dd, J=6.8 Hz, 2.7 Hz, 1H); 7.63-7.48 (m, 3H); 7.36 (t, J=9.1 Hz, 1H); 6.94 (d, J=9.1 Hz, 2H); 4.30-3.84 (m, 8H); 1.27 (t, J=6.9 Hz, 4H). MS 485, 487 (MH$^+$).

N$^7$-(3-chloro-4-fluoro-phenyl)-N$^2$-(4-{3-[4-(4-chloro-phenyl)-piperazin-1-yl]-propoxy}-phenyl)-thiazolo[4,5-d]pyrimidine-2,7-diamine (Cpd 16)

4-{3-[4-(4-chloro-phenyl)-piperazin-1-yl]-propoxy}-phenylamine was used in place of Compound 1g and Compound 2g was used in place of Compound 1e. Isolated as a trifluoroacetate salt. $^1$H NMR (DMSO-$d_6$) δ 10.91 (br s, 1H); 9.63 (br s, 1H); 9.58 (s, 1H); 8.44 (s, 1H); 7.95 (dd, J=6.9 Hz, 2.7 Hz, 1H), 7.66-7.54 (m, 3H); 7.35 (t, J=9.2 Hz, 1H); 7.21 (t, J=8.2 Hz, 1H); 7.05-6.89 (m, 4H); 6.82 (d, J=8.2 Hz, 1H); 4.02 (t, 5.7 Hz, 2H); 3.87 (d, J=12.0 Hz, 2H); 3.58 (d, J=10.9 Hz, 2H); 3.39-3.22 (m, 2H); 3.20-2.91 (m, 4H); 2.20-2.05 (m, 2H). MS 624, 626 (MH$^+$).

N$^7$-(3-chloro-4-fluoro-phenyl)-N$^2$-(4-pyrrolidin-1-ylmethyl-phenyl)-thiazolo[4,5-d]pyrimidine-2,7-diamine (Cpd 17)

4-pyrrolidin-1-ylmethyl-phenylamine was used in place of Compound 1g and Compound 2g was used in place of Compound 1e. Isolated as a trifluoroacetate salt. $^1$H NMR (DMSO-$d_6$) δ 11.26 (s, 1H); 9.83 (br s, 1H); 9.69 (s, 1H); 8.55 (s, 1H); 8.05 (dd, J=6.8 Hz, 2.6 Hz, 1H); 7.88 (d, J=8.6 Hz, 2H); 7.67 (ddd, J=9.2 Hz, 4.1 Hz, 2.6 Hz, 1H); 7.57 (d, J=8.6 Hz, 2H); 7.44 (t, J=9.2 Hz, 1H); 4.36 (s, 2H); 3.40-3.37 (m, 2H); 3.15-3.09 (m, 2H); 2.06 (m, 2H); 1.91-1.87 (m, 2H). MS 455, 457(MH$^+$).

N$^7$-(3-chloro-4-fluoro-phenyl)-N$^2$-(4-morpholin-4-ylmethyl-phenyl)-thiazolo[4,5-d]pyrimidine-2,7-diamine (Cpd 18)

4-morpholin-4-ylmethyl-phenylamine was used in place of Compound 1g and Compound 2g was used in place of Compound 1e. Isolated as a trifluoroacetate salt. $^1$H NMR (DMSO-$d_6$) δ 11.29 (s, 1H); 9.94 (br s, 1H); 9.70 (s, 1H); 8.57 (s, 1H); 8.07 (dd, J=6.9 Hz, 2.8 Hz, 1H); 7.93(d, J=8.7 Hz, 2H); 7.70 (ddd, J=9.1 Hz, 4.2 Hz, 2.8 Hz, 1H); 7.59 (d, J=8.7 Hz, 2H); 7.47 (t, J=9.1 Hz, 1H); 4.38 (s, 2H); 4.02 (d, J=12.3 Hz, 2H); 3.68 (t, J=12.3 Hz, 2H); 3.32 (d, J=13.1 Hz, 2H); 3.17 (m, 2H). MS 471, 473(MH$^+$).

N$^2$-(4-azepan-1-ylmethyl-phenyl)-N$^7$-(3-chloro-4-fluoro-phenyl)-thiazolo[4,5-d]pyrimidine-2,7-diamine (Cpd 19)

4-azepan-1-ylmethyl-phenylamine was used in place of Compound 1g and Compound 2g was used in place of Compound 1e. Isolated as a trifluoroacetate salt. $^1$H NMR (DMSO-$d_6$) δ 11.25 (s, 1H); 9.68 (s, 1H); 9.43 (br s, 1H); 8.54 (s, 1H); 8.05 (dd J=6.8 Hz, 2.5 Hz, 1H); 7.89 (d, J=8.5 Hz, 2H); 7.69-7.64 (m, 1H); 7.58 (d, J=8.5 Hz, 2H); 7.44 (t, J=9.1 Hz, 1H); 4.34 (s, 2H); 3.37-3.31 (m, 2H); 3.15-3.08 (m, 2H); 1.90-1.64 (m, 8H). MS 483, 485(MH$^+$).

$N_7$-(3-chloro-4-fluoro-phenyl)-N$^2$-(4-thiomorpholin4-ylmethyl-phenyl)-thiazolo[4,5-d]pyrimidine-2,7-diamine (Cpd 20)

4-thiomorpholin-4-ylmethyl-phenylamine was used in place of Compound 1g and Compound 2g was used in place of Compound 1e. Isolated as a trifluoroacetate salt. $^1$H NMR (DMSOd$_6$) δ 11.24 (s, 1H); 9.66 (br s, 2H); 8.53 (s, 1H); 8.04 (dd, J=6.9 Hz, 2.6 Hz, 1H); 7.89 (d, J=8.4 Hz, 2H); 7.66 (ddd, J=9.1 Hz, 4.2 Hz, 2.6 Hz, 1H); 7.55 (d, J=8.4 Hz, 2H); 7.43 (t, J=9.1 Hz, 1H); 4.36 (br s, 2H); 3.67-3.62 (m, 2H); 3.16-3.12 (m, 2H); 2.97-2.85(m, 4H). MS 487, 489(MH$^+$).

N$^7$-(3-chloro-4-fluoro-phenyl)-N$^2$-{4-[(cyclohexyl-methyl-amino)-methyl]-phenyl}-thiazolo[4,5-d]pyrimidine-2,7-diamine (Cpd 21)

4-[(cyclohexyl-methyl-amino)-methyl]-phenylamine was used in place of Compound 1g and Compound 2g was used in place of Compound 1e. Isolated as a trifluoroacetate salt. $^1$H NMR (DMSO-$d_6$) δ 9.39 (br s, 1H); 8.72 (br s, 1H); 8.44 (br s,1H); 7.70 (dd, J=6.6 Hz, 1.8 Hz, 1H); 7.69 (d, J=7.4 Hz, 2H); 7.41-7.34 (m, 3H); 7.20 (t, J=9.2 Hz, 1H); 4.25-4.16 (m, 1H); 4.06-3.94 (m, 1H); 3.20-3.12 (m, 1H); 2.47 (s, 3H); 2.07-1.77 (m, 4H); 1.63-1.57 (m, 1H); 1.47-1.38 (m, 2H); 1.32-1.09 (m, 3H). MS 497, 499(MH$^+$).

N$^2$-[4-(4-aminomethyl-piperidin-1-ylmethyl)-phenyl]-N$^7$-(3-chloro-4-fluoro-phenyl)-thiazolo[4,5-d]pyrimidine-2,7-diamine (Cpd 22)

[1-(4-amino-benzyl)-piperidin-4-ylmethyl]-carbamic acid tert-butyl ester was used in place of Compound 1g and Compound 2g was used in place of Compound 1e. Deprotection in 25% TFA/$CH_2Cl_2$. Isolated as a trifluoroacetate salt. $^1$H NMR (DMSO-$d_6$) δ 11.23 (s, 1H); 9.65 (s, 1H); 9.36 (br s, 1H); 8.54 (s, 1H); 8.05 (dd, J=6.8 Hz, 2.7 Hz, 1H); 7.90 (d, J=8.7 Hz, 2H); 7.78 (br s, 2H); 7.67 (ddd, J=9.0 Hz, 4.4 Hz, 2.7 Hz, 1H); 7.54 (d, J=8.7 Hz, 2H); 7.44 (t, J=9.0 Hz, 1H); 4.29 (br s, 2H); 3.45-3.42 (m, 2H); 2.98-2.93 (m, 2H); 2.77-2.74 (m, 2H); 2.29-2.28 (m, 1H); 1.97-1.92 (m, 2H); 1.83-1.81 (m, 2H); 1.39-1,35 (m, 2H). MS 498, 500 (MH$^+$).

N$^7$-(3-chloro-4-fluoro-phenyl)-N$^2$-(4-imidazol-1-ylmethyl-phenyl)-thiazolo[4,5-d]pyrimidine-2,7-diamine (Cpd 23)

4-imidazol-1-ylmethyl-phenylamine was used in place of Compound 1g and Compound 2g was used in place of Compound 1e. Isolated as a trifluoroacetate salt. $^1$H NMR (DMSO-$d_6$) δ 11.17 (s, 1H); 9.65 (s, 1H); 9.25 (s, 1H); 8.53 (s, 1H); 8.03 (dd, J=6.8 Hz, 2.8 Hz, 1H); 7.84-7.80 (m, 3H); 7.71 (s, 1H); 7.65 (ddd, J=9.1 Hz, 4.4 Hz, 2.8 Hz, 1H); 7.49 (d, J=8.5 Hz, 2H); 7.42 (t, J=9.1 Hz, 1H); 5.42 (s, 2H). MS 452, 454 (MH$^+$).

N$^7$-(3-chloro-4-fluoro-phenyl)-N$^2$-[4-(3,5-dimethyl-piperidin-1-ylmethyl)-phenyl]-thiazolo[4,5-d]pyrimidine-2,7-diamine (Cpd 24)

4-(3,5-dimethyl-piperidin-1-ylmethyl)-phenylamine was used in place of Compound 1g and Compound 2g was used in place of Compound 1e. Isolated as a trifluoroacetate salt. $^1$H NMR (DMSO-$d_6$) δ 11.25 (s, 1H); 9.68 (s, 1H); 9.48 (br s, 1H); 9.01 (br s, 1H); 8.54 (s, 1H); 8.04 (dd, J=6.8 Hz, 2.8 Hz, 1H); 7.89 (d, J=8.4 Hz, 2H); 7.66 (ddd, J=9.0 Hz, 4.3 Hz, 2.8 Hz, 1H); 7.55 (dd, J=8.4 Hz, 2.5 Hz, 2H); 7.43 (t, J=9.0 Hz, 1H); 4.27 (s, 2H); 1.07 (d, J=7.4 Hz, 3H); 0.89 (d, J=6.7 Hz, 3H), mixture of regioisomers, only select aliphatic signals given. MS 497, 499 (MH$^+$).

(2S)-(1-{4-[7-(3-chloro-4-fluoro-phenylamino)-thiazolo[4,5-d]pyrimidinylamino]-benzyl}-pyrrolidin-2-yl)-methanol (Cpd 25)

(2S)-[1-(4-amino-benzyl)-pyrrolidin-2-yl]-methanol was used in place of Compound 1g and Compound 2g was used in place of Compound 1e. Isolated as a trifluoroacetate salt. $^1$H NMR (DMSO-$d_6$) δ 12.11 (br s, 1H); 10.47 (br s, 1H); 10.23 (br s, 1H); 8.63 (s, 1H); 8.01 (dd, J=6.8 Hz, 2.6 Hz, 1H); 7.87 (d, J=8.5 Hz, 2H); 7.70-7.64 (m, 3H); 7.37 (t, J=9.2 Hz, 1H); 4.52 (dd, J=12.9 Hz, 4.3 Hz, 1H); 4.25 (dd, J=12.9 Hz, 6.2 Hz, 1H); 3.64-3.53 (m, 3H); 3.26-3.23 (m, 1H); 3.15-3.09 (m, 1H); 2.10-2.07 (m, 1H); 1.96-1.76 (m, 3H). MS 485, 487 (MH$^+$).

N$^7$-(3-chloro-4-fluoro-phenyl)-N$^2$-[4-(2S)-(2-methoxymethyl-pyrrolidin-1-ylmethyl)-phenyl]-thiazolo[4,5-d]pyrimidine-2,7-diarmine (Cpd 26)

4-(2S)-(2-methoxymethyl-pyrrolidin-1-ylmethyl)-phenylamine was used in place of Compound 1g and Compound 2g was used in place of Compound 1e. Isolated as a trifluoroacetate salt. $^1$H NMR (DMSO-$d_6$) δ 11.20 (s, 1H); 9.63 (s, 1H); 9.48 (br s, 1H); 8.52 (s, 1H); 8.02 (dd, J=6.9 Hz, 2.7 Hz, 1H); 7.86 (d, J=8.7 Hz, 2H); 7.64 (ddd, J=9.0 Hz, 4.4 Hz, 2.7 Hz, 1H); 7.55 (d, J=8.7 Hz, 2H); 7.41 (t, J=9.0 Hz, 1H); 4.49-4.42 (m, 1H); 4.29-4.23 (m, 1H); 3.74-3.70 (m, 1H); 3.58-3.45 (m, 3H); 3.30 (s, 3H); 3.26-3.20 (m, 1H); 2.42-1.69 (m, 4H). MS 499, 501 (MH$^+$).

4-[7-(3-chloro-4-fluoro-phenylamino)-thiazolo[4,5-d]pyrimidin-2-ylamino]-N,N-dimethyl-benzamide (Cpd 27)

4-amino-N,N-dimethyl-benzamide was used in place of Compound 1g and Compound 2g was used in place of Compound 1e. Isolated as a trifluoroacetate salt. $^1$H NMR ($DMSO-d_6$) δ 11.31 (br s, 1H); 9.82 (br s, 1H); 8.58 (s, 1H); 8.03 (dd, J=6.8 Hz, 2.7 Hz, 1H); 7.84 (d, J=8.5 Hz, 2H); 7.66 (ddd, J=9.1 Hz, 4.4 Hz, 2.7 Hz, 1H); 7.50 (d, J=8.5 Hz, 2H); 7.45 (t, J=9.1 Hz, 1H); 2.99 (s, 6H). MS 443, 445 ($MH^+$).

4-{4-[7-(3-chloro-4-fluoro-phenylamino)-thiazolo[4,5-d]pyrimidin-2-ylamino]-benzyl}-piperazine-1-carboxylic acid ethyl ester (Cpd 28)

4-(4-amino-benzyl)-piperazine-1-carboxylic acid ethyl ester was used in place of Compound 1g and Compound 2g was used in place of Compound 1e. Isolated as a trifluoroacetate salt. $^1$H NMR ($DMSO-d_6$) δ 11.29 (s, 1H); 9.91 (br s, 1H); 9.72 (s, 1H); 8.57 (s, 1H); 8.07 (dd, J=6.9 Hz, 2.6 Hz, 1H); 7.92 (d, J=8.6 Hz, 2H); 7.69 (ddd, J=9.1 Hz, 4.2 Hz, 2.6 Hz, 1H); 7.56 (d, J=8.6 Hz, 2H); 7.46 (t, J=9.1 Hz, 1H); 4.36 (s, 2H); 4.15-4.08 (m, 4H); 3.37-3.31 (m, 2H); 3.21-3.01 (m, 4H); 1.23 (t, J=7.1 Hz, 3H). MS 542, 544 ($MH^+$).

1-{4-[7-(3-chloro-4-fluoro-phenylamino)-thiazolo[4,5-d]pyrimidin-2-ylamino]-benzyl}-piperidine-4-carboxylic acid ethyl ester (Cpd 29)

1-(4-amino-benzyl)-piperidine-4-carboxylic acid ethyl ester was used in place of Compound 1g and Compound 2g was used in place of Compound 1e. Isolated as a trifluoroacetate salt. $^1$H NMR ($DMSO-d_6$) δ 11.23 (s, 1H); 9.66 (s, 1H); 9.34 (br s, 1H); 8.54 (s, 1H); 8.04 (dd, J=7.1 Hz, 2.7 Hz, 1H); 7.88 (d, J=8.6 Hz, 2H); 7.67 (ddd, J=9.1 Hz, 4.2 Hz, 2.7 Hz, 1H); 7.53 (d, J=8.6 Hz, 2H); 7.43 (t, J=9.1 Hz, 1H); 4.29 (br s, 2H); 4.09 (q, J=7.1 Hz, 2H); 3.45-3.39 (m, 2H); 3.00-2.96 (m, 2H); 2.64-2.57 (m, 1H); 2.12-2.07(m, 2H); 1.80-1.70 (m, 2H); 1.19 (t, J=7.1 Hz, 3H). MS 541, 543 ($MH^+$).

$N^7$-(3-chloro-4-fluoro-phenyl)-$N^2$-[4-(2-ethyl-imidazol-1-ylmethyl)-phenyl]-thiazolo[4,5-d]pyrimidine-2,7-diamine (Cpd 30)

4-(2-ethyl-imidazol-1-ylmethyl)-phenylamine was used in place of Compound 1g and Compound 2g was used in place of Compound 1e. Isolated as a trifluoroacetate salt. $^1$H NMR ($DMSO-d_6$) δ 14.57 (br s, 1H); 12.30 (s, 1H); 10.72 (s, 1H); 8.68 (s, 1H); 8.02 (dd, J=6.8, 2.4 Hz, 1H); 7.87 (d, J=8.4 Hz, 2H); 7.75-7.64 (m, 4H); 7.47 (t, J=9.1 Hz, 1H); 7.42 (d, J=8.5 Hz, 1H); 5.42 (s, 2H); 3.02 (q, J=7.5 Hz, 2H); 1.21 (t, J=7.5 Hz, 3H). MS 480, 482 ($MH^+$).

4-[7-(3-chloro-4-fluoro-phenylamino)-thiazolo[4,5-d]pyrimidin-2-ylamino]-N-(3-dimethylamino-propyl)-benzenesulfonamide (Cpd 31)

4-amino-N-(3-dimethylamino-propyl)-benzenesulfonamide was used in place of Compound 1g and Compound 2g was used in place of Compound 1e. Isolated as a trifluoroacetate salt. $^1$H NMR ($DMSO-d_6$) δ 11.83 (s, 1H); 9.98 (s, 1H); 9.76 (br s, 1H); 8.61 (s, 1H); 8.06-8.03 (m, 3H); 7.86 (d, J=8.5 Hz, 2H); 7.74-7.70 (m, 1H); 7.46 (t, J=8.9 Hz, 1H); 3.12-3.02 (m, 2H); 2.89-2.70 (m, 8H); 1.87-1.73 (m, 2H). MS 536, 538 ($MH^+$).

4-[7-(3-chloro-4-fluoro-phenylamino)-thiazolo[4,5-d]pyrimidin-2-ylamino]-N,N-bis-(2-methoxy-ethyl)-benzenesulfonamide (Cpd 32)

4-amino-N,N-bis-(2-methoxy-ethyl)-benzenesulfonamide was used in place of Compound 1g and Compound 2g was used in place of Compound 1e. Isolated as a trifluoroacetate salt. $^1$H NMR ($DMSO-d_6$) δ 11.44 (s, 1H); 9.71 (s, 1H); 8.55 (s, 1H); 8.04 (dd, J=6.7 Hz, 2.5 Hz, 1H); 7.99 (d, J=8.8 Hz, 2H); 7.86 (d, J=8.8 Hz, 2H); 7.68 (ddd, J=9.1 Hz, 4.1 Hz, 2.5 Hz, 1H); 7.43 (t, J=9.1 Hz, 1H); 3.52-3.40 (m, 4H); 3.29 (t, J=5.7 Hz, 4H); 3.21 (s, 6H). MS 567, 569 ($MH^+$).

4-[7-(3-ethynyl-phenylamino)-thiazolo[4,5-d]pyrimidin-2-ylamino]-N,N-bis-(2-methoxy-ethyl)-benzenesulfonamide (Cpd 33)

4-amino-N,N-bis-(2-methoxy-ethyl)-benzenesulfonamide was used in place of Compound 1g. Isolated as a trifluoroacetate salt. $^1$H NMR ($DMSO-d_6$) δ 11.52 (s, 1H); 9.80 (s, 1H); 8.60 (s, 1H); 8.00 (d, J=8.8 Hz, 2H); 7.90-7.89 (m, 3H); 7.73 (d, J=7.9 Hz, 1H); 7.41 (t, J=7.9 Hz, 1H); 7.24 (d, 7.9 Hz, 1H); 4.23 (s, 1H); 3.45 (t, J=5.8 Hz, 4H); 3.31 (t, J=5.8 Hz, 4H); 3.23 (s, 6H). MS 539 ($MH^+$).

$N^2$-(4-{[bis-(2-methoxy-ethyl)-amino]-methyl}-phenyl)-$N^7$-(3-chloro-4-fluoro-phenyl)-thiazolo[4,5-d]pyrimidine-2,7-diamine (Cpd 34)

4-{[bis-(2-methoxy-ethyl)-amino]-methyl}-phenylamine was used in place of Compound 1g and Compound 2g was used in place of Compound 1e. Isolated as a trifluoroacetate salt. $^1$H NMR ($DMSO-d_6$) δ 11.39 (br s, 1H); 9.81 (s, 1H); 9.68 (br s, 1H); 8.59 (s, 1H); 8.07 (dd, J=6.8 Hz, 2.6 Hz, 1H); 7.92 (d, J=8.5 Hz, 2H); 7.69 (ddd, J=9.0 Hz, 4.2 Hz, 2.6 Hz, 1H); 7.63 (d, J=8.5 Hz, 2H); 7.47 (t, J=9.0 Hz, 1H); 4.59 (s, 2H); 3.81-3.69 (m, 4H); 3.48-3.30 (m, 10H). MS 517, 519 ($MH^+$).

$N^7$-(3-ethynyl-phenyl)-$N^2$-(4-morpholin-4-ylmethyl-phenyl)-thiazolo[4,5-d]pyrimidine-2,7-diamine (Cpd 35)

4-morpholin-4-ylmethyl-phenylamine was used in place of Compound 1g. Isolated as a trifluoroacetate salt. $^1$H NMR ($DMSO-d_6$) δ 11.24 (s, 1H); 9.83 (br s, 1H); 9.63 (s, 1H); 8.55 (s, 1H); 7.92-7.90 (m, 3H); 7.73 (d, J=7.6 Hz, 1H); 7.56 (d, J=8.4 Hz, 2H); 7.40 (t, J=7.6 Hz, 1H); 7.23 (d, J=7.6 Hz, 1H); 4.36 (s, 2H); 4.22 (s, 1H); 4.03-3.61 (m, 4H); 3.33-3.29 (m, 2H); 3.20-3.06 (m, 2H). MS 443 ($MH^+$).

$N^7$-(1-benzyl-1H-indazol-6-yl)-$N^2$-(4-morpholin-4-ylmethyl-phenyl)-thiazolo[4,5-d]pyrimidine-2,7-diamine (Cpd 36)

4-morpholin-4-ylmethyl-phenylamine was used in place of Compound 1g and 1-benzyl-1H-indazol-6-ylamine was used in place of Compound 1e. Isolated as a trifluoroacetate salt. $^1$H NMR ($DMSO-d_4$) δ 11.17 (br s, 1H); 9.86 (br s, 1H); 8.53 (s, 1H); 8.11 (s, 1H); 7.97(s, 1H); 7.87 (d, J=8.4 Hz, 2H); 7.78 (d, J=8.6 Hz, 1H); 7.54 (d, J=8.4 Hz, 2H); 7.38-7.20 (m, 7H); 5.64 (s, 4H); 4.42-4.11 (m, 4H) 3.48-3.10 (m, 4H) MS 549, 551 ($MH^+$).

N-(3-dimethylamino-propyl)-4-[7-(3-ethynyl-phenylamino)-thiazolo[4,5-d]pyrimidin-2-ylamino]-benzenesulfonamide (Cpd 37)

4-amino-N-(3-dimethylamnino-propyl)-benzenesulfonamide was used in place of Compound 1g. Isolated as a trifluoroacetate salt. $^1$H NMR ($DMSO-d_6$) δ 11.44 (s, 1H); 9.65 (s, 1H); 9.24 (br s, 1H); 8.57 (s, 1H); 8.02 (d, J=8.7 Hz, 2H); 7.91 (s, 1H); 7.86 (d, J=8.7 Hz, 1H); 7.75-7.67 (m, 1H); 7.41

(t, J=8.0 Hz, 1H); 7.33 (d, J=8.0 Hz, 1H); 4.23 (s, 1H); 3.11-3.04 (m, 2H); 2.86-2.82 (m, 2H); 2.77 (s, 6H); 1.83-1.73 (m, 2H). MS 508 ($MH^+$).

$N^2$-(4-{[bis-(2-methoxy-ethyl)-amino]-methyl}-phenyl)-$N^7$-(3-ethynyl-phenyl)-thiazolo[4,5-d]pyrimidine-2,7-diamine (Cpd 38)

4-{[bis-(2-methoxy-ethyl)-amino]-methyl}-phenylamine was used in place of Compound 1g. Isolated as a trifluoroacetate salt. $^1H$ NMR (DMSO-$d_6$) δ 11.35 (br s, 1H); 9.76 (s, 1H); 9.72 (br s, 1H); 8.57 (s, 1H); 7.89 (m, 3H); 7.73 (d, J=8.0 Hz, 1H); 7.61 (d, J=8.4 Hz, 2); 7.41 (t, J=8.0 Hz, 1H); 7.24 (d, J=8.0 Hz, 1H); 4.41 (br s, 2H); 4.23 (s, 1H); 3.79-3.65 (m, 4H); 3.44-3.26 (m, 10H). MS 489 ($MH^+$).

4-[7-(3-chloro-4-fluoro-phenylamino)-thiazolo[4,5-d]pyrimidin-2-ylamino]-N-(2-hydroxy-ethyl)-benzenesulfonamide (Cpd 39)

4-amino-N-(2-hydroxy-ethyl)-benzenesulfonamide was used in place of Compound 1g and Compound 2g was used in place of Compound 1e. Isolated as a trifluoroacetate salt. $^1H$ NMR (DMSO-$d_6$) δ 11.43 (br s, 1H); 9.74 (s, 1H); 8.52 (s, 1H); 7.98 (dd, J=7.0 Hz, 2.7 Hz, 1H); 7.92 (d, J=8.8 Hz, 2H); 7.79 (d, J=8.8 Hz, 2H); 7.60 (ddd, J=9.1 Hz, 4.2 Hz, 2.7 Hz, 1H); 7.47 (t, J=6.1 Hz, 1H); 7.38 (t, J=9.1 Hz, 1H); 3.32 (t, J=6.1 Hz, 2H); 2.75 (q, J=6.1 Hz, 2H). MS 495, 497 ($MH^+$).

4-[7-(3-chloro-4-fluoro-phenylamino)-thiazolo[4,5-d]pyrimidin-2-ylamino]-N-(2-morpholin-4-yl-ethyl)-benzenesulfonamide (Cpd 40)

4-amino-N-(2-morpholin-4-yl-ethyl)-benzenesulfonamide was used in place of Compound 1g and Compound 2g was used in place of Compound 1e. Isolated as a trifluoroacetate salt. $^1H$ NMR (DMSO-$d_6$) δ 11.46 (br, s 1H); 10.70 (br s, 1H); 9.69 (br s, 1H); 8.53 (s, 1H); 8.00 (d, J=8.7 Hz, 2H); 7.92-7.80 (m, 3H); 7.70-7.58 (m, 1H); 7.40 (t, J=9.6Hz, 1H); 4.04-3.87 (m, 2H); 3.26-3.01 (m, 10H). MS 564, 566 ($MH^+$).

4-[7-(3-chloro-4-fluoro-phenylamino)-thiazolo[4,5-d]pyrimidin-2-ylamino]-N-(3-morpholin-4-yl-propyl)-benzenesulfonamide (Cpd 41)

4-amino-N-(3-morpholin-4-yl-propyl)-benzenesulfonamide was used in place of Compound 1g and Compound 2g was used in place of Compound 1e. Isolated as a trifluoroacetate salt. $^1H$ NMR (DMSO-$d_6$) δ 11.55 (br s, 1H); 10.73 (s, 1H); 9.80 (br s, 2H); 8.58 (s, 1H); 8.09-7.99 (m, 3H); 7.89-7.79 (m, 2H); 7.76-7.64 (m, 1H); 7.45 (t, J=9.2Hz, 1H); 3.72-3.61 (m, 2H); 3.48-3.35 (m, 2H); 3.23-3.01 (m, 4H); 2.94-2.79 (m, 2H); 1.87-1.78 (m, 2H). MS 578, 580 ($MH^+$).

$N^7$-(3-ethynyl-phenyl)-$N^2$-(4-pyrrolidin-1-ylmethyl-phenyl)-thiazolo[4,5-d]pyrimidine-2,7-diamine (Cpd 42)

4-pyrrolidin-1-ylmethyl-phenylamnine was used in place of Compound 1g. Isolated as a trifluoroacetate salt. $^1H$ NMR (DMSO-$d_6$) δ 11.33 (br s, 1H); 9.96 (br s, 1H); 9.78 (s, 1H); 8.57 (br s, 1H); 7.88-7.85 (m, 3H); 7.71 (d, J=7.7 Hz, 1H); 7.56 (d, J=8.3 Hz, 2H); 7.39 (t, J=7.7 Hz, 1 Hz); 7.23 (d, 7.7 Hz, 1H); 4.34 (s, 2H); 4.21 (s, 1H); 3.39-3.38 (m, 2H); 3.14-3.11 (m, 2H); 2.04-2.07(m, 2H); 1.90-1.86(m, 2H). MS 427 ($MH^+$).

(2S)-(1-{4-[7-(3-ethynyl-phenylamino)-thiazolo[4,5-d]pyrimidin-2-ylamino]-benzyl}-pyrrolidin-2-yl)-methanol (Cpd 44)

(2S)-[1-(4-amino-benzyl)-pyrrolidin-2-yl]-methanol was used in place of Compound 1g. Isolated as a trifluoroacetate salt. $^1H$ NMR (DMSO-$d_6$) δ 11.34 (br s, 1H); 9.77 (br s, 1H); 9.48 (br s, 1H); 8.58 (s, 1H); 7.89-7.87 (m, 3H); 7.73 (d, J=7.9 Hz, 1H); 7.60 (d, J=8.4 Hz, 2H); 7.41 (t, J=7.9 Hz, 1H); 7.25 (d, J=7.9 Hz, 1H); 4.59-4.49 (m, 1H); 4.34-4.25 (m, 1H); 4.23 (s, 1H); 3.69-3.53 (m, 2H); 3.37-3.13 (m, 3H); 2.22-1.70 (m, 4H). MS 457 ($MH^+$).

$N^7$-(3-ethynyl-phenyl)-$N^2$-[4-(morpholine-4-sulfonyl)-phenyl]-thiazolo[4,5-d]pyrimidine-2,7-diamine (Cpd 45)

4-(morpholine-4-sulfonyl)-phenylamine was used in place of Compound 1g. Isolated as a trifluoroacetate salt. $^1H$ NMR (DMSO-$d_6$) δ 11.63 (br s, 1H); 9.89 (s, 1H); 8.64 (br s, 1H); 8.06 (d, J=8.5 Hz, 2H); 7.90 (s, 1H); 7.82 (d, J=8.5 Hz, 2H); 7.73 (d, J=7.6 Hz, 1H); 7.42 (t, J=7.6 Hz, 1H); 7.27 (d, J=7.6 Hz, 1H); 4.23 (s, 1H); 3.73-3.60 (m, 4H); 2.97-2.83 (m, 4 H). MS 493 ($MH^+$).

$N^7$-(3-chloro-4-fluoro-phenyl)-$N^2$-[4-(morpholine-4-sulfonyl)-phenyl]-thiazolo[4,5-d]pyrimidine-2,7-diamine (Cpd 46)

4-(morpholine-4-sulfonyl)-phenylamine was used in place of Compound 1g and Compound 2g was used in place of Compound 1e. Isolated as a trifluoroacetate salt. $^1H$ NMR (DMSO-$d_6$) δ 11.50 (s, 1H); 9.71 (s, 1H); 8.56 (s, 1H); 8.07-8.03 (m, 3H); 7.80 (d, J=8.8 Hz, 2H); 7.67 (ddd, J=9.2 Hz, 4.3 Hz, 2.7 Hz, 1H); 7.43 (t, J=9.2 Hz, 1H); 3.75-3.58 (m, 4H); 2.91-2.84 (m, 4H). MS 521, 523 ($MH^+$).

$N^7$-(3-ethynyl-phenyl)-$N^2$-[4-(4-methyl-piperazin-1-ylmethyl)-phenyl]-thiazolo[4,5-d]pyrimidine-2,7-diamine (Cpd 47)

4-(4-methyl-piperazin-1-ylmethyl)-phenylamine was used in place of Compound 1g. Isolated as a trifluoroacetate salt. $^1H$ NMR (DMSO-$d_6$) δ 11.12 (br s, 1H); 9.63 (br s, 1H); 8.52 (s, 1H); 7.88 (s, 1H); 7.77 (d, J=8.0 Hz, 2H); 7.70 (d, J=7.3 Hz, 1H); 7.40-7.33 (m, 3H); 7.21 (d, J=7.3 Hz, 1H); 4.20 (s, 1H); 3.76-3.70 (m, 2H); 3.42-3.36 (m, 2H); 3.09-2.96 (m, 4H); 2.81-2.72 (m, 5H). MS 456 ($MH^+$).

$N^2$-[4-(2-ethyl-imidazol-1-ylmethyl)-phenyl]-$N^7$-(3-ethynyl-phenyl)-thiazolo[4,5-d]pyrimidine-2,7-diamine (Cpd 48)

4-(2-ethyl-imidazol-1-ylmethyl)-phenylamine was used in place of Compound 1g. Isolated as a trifluoroacetate salt. $^1H$ NMR (DMSO-$d_6$) δ 14.13 (br s, 1H); 11.14 (s, 1H); 9.59 (s, 1H); 8.53 (s, 1H); 7.88 (t, J=1.2 Hz, 1H); 7.82 (d, J=8.6 Hz, 2H); 7.74-7.69 (m, 2H); 7.67 (d, J=1.9 Hz, 1H); 7.40 (d, J=8.6 Hz, 2H); 7.38 (t, J=7.8 Hz, 1H); 7.21 (dt, J=7.8, 1.2 Hz, 1H); 5.41 (s, 2H); 4.21 (s, 1H); 3.01 (q, J=7.6 Hz, 2H); 1.22 (q, J=7.6 Hz, 3H). MS 452 ($MH^+$).

N$^2$-(4-dimethylaminomethyl-phenyl)-N$^7$-(3-ethynyl-phenyl)-thiazolo[4,5-d]pyriridine-2,7-diamine (Cpd 49)

4-dimethylaminomethyl-phenylamine was used in place of Compound 1g. Isolated as a trifluoroacetate salt. $^1$H NMR (DMSO-d$_6$) δ 11.23(s, 1H); 9.63 (s, 1H); 9.60 (br s, 1H); 8.54 (s, 1H); 7.92-7.86 (m, 3H); 7.72 (d, J=7.9 Hz, 1H); 7.53 (d, J=8.7 Hz, 2H); 7.39 (t, J=7.9 Hz, 1H); 7.22 (dt, J=7.9, 1.3 Hz, 1H); 4.27 (s, 2H); 4.21 (s, 1H); 2.75 (s, 6H). MS 401 (MH$^+$).

N$^7$-(3-ethynyl-phenyl)-N$^2$-[4-(2-morpholin-4-yl-ethyl)-phenyl]-thiazolo[4,5-d]pyrimidine-2,7-diamine (Cpd 50)

4-(2-morpholin-4-yl-ethyl)-phenylamine was used in place of Compound 1g. Isolated as a trifluoroacetate salt. $^1$H NMR (DMSO-d$_6$) δ 11.17(br s, 1H); 9.86 (br s, 1H); 9.71 (br s, 1H); 8.61 (s, 1H); 7.96 (br s, 1H); 7.84 (d, J=8.2 Hz, 2H); 7.79 (dd, J=8.0, 1.2 Hz, 1H); 7.47 (t, J=8.0 Hz, 1H); 7.42 (d, J=8.2 Hz, 2H); 7.29 (dd, J=8.0, 1.2 Hz, 1H); 4.29 (s, 1H); 4.12 (d, J=12.5 Hz, 2H); 3.75 (t, J=12.5 Hz, 2H); 3.61 (d, J=12.5 Hz, 2H); 3.51-3.40 (m, 2H); 3.30-3.14 (m, 2H); 3.12-3.03 (m, 2H). MS 457(MH$^+$).

N$^7$-(3-chloro-4-fluoro-phenyl)-N$^2$-(2-morpholin-4-yl-ethyl)-thiazolo[4,5-d]pyrimidine-2,7-diamine (Cpd 51)

2-morpholin-4-yl-ethylamine was used in place of Compound 1g and Compound 2g was used in place of Compound 1e. Isolated as a trifluoroacetate salt. MS 409, 411 (MH$^+$).

N$^7$-(3-chloro-4-fluoro-phenyl)-N$^2$-(3-morpholin-4-yl-propyl)-thiazolo[4,5-d]pyrimidine-2,7-diamine (Cpd 52)

3-morpholin-4-yl-propylamine was used in place of Compound 1g and Compound 2g was used in place of Compound 1e. Isolated as a trifluoroacetate salt. MS 423, 425(MH$^+$).

N$^7$-(3-chloro-4-fluoro-phenyl)-N$^2$-{4-[(2-isopropoxy-ethylamino)-methyl]-phenyl}-thiazolo[4,5-d]pyrimidine-2,7-diamine (Cpd 53)

4-[(2-isopropoxy-ethylamino)-methyl]-phenylamine was used in place of Compound 1g and Compound 2g was used in place of Compound 1e. Isolated as a trifluoroacetate salt. $^1$H NMR (DMSO-d$_6$) δ 11.18 (s, 1H); 9.65 (s, 1H); 8.79 (br s, 1H); 8.53 (s, 1H); 8.03 (dd, J=6.6, 2.6 Hz, 1H); 7.85 (d, J=8.5 Hz, 2H); 7.69-7.62 (m, 1H); 7.54 (d, J=8.5 Hz, 2H); 7.42 (t, J=9.0 Hz, 1H); 4.24-4.11 (m, 2H); 3.71-3.56 (m, 3H); 3.17-3.01 (m, 2H), 1.14 (d, J=6.1 Hz, 6H). MS 487, 489 (MH$^+$).

(2R)-(1-{4-[7-(3-ethynyl-phenylamino)-thiazolo[4,5-d]pyrimidin-2-ylamino]-benzyl}-pyrrolidin-2-yl)-methanol (Cpd 54)

(2R)-[1-(4-amino-benzyl)-pyrrolidin-2-yl]-methanol was used in place of Compound 1g. Isolated as a trifluoroacetate salt. $^1$H NMR (DMSO-d$_4$) δ 11.18 (s, 1H); 9.58 (s, 1H); 9.35 (br s, 1H); 8.53 (s, 1H); 7.86 (d, J=8.4 Hz, 2H); 7.71 (d, J=7.9 Hz, 1H); 7.57 (d, J=8.4 Hz, 2H); 7.38 (t, J=7.9 Hz, 1H); 7.21 (d, J=7.9 Hz, 1H); 4.56-4.45 (m, 1H); 4.32-4.22 (m, 1H); 4.20 (s, 1H); 3.68-3.51 (m, 2H); 3.39-3.12 (m, 3H); 2.20-1.71 (m, 4H). MS 457 (MH$^+$).

N$^7$-(3-ethynyl-phenyl)-N$^2$-{4-[(2-isopropoxy-ethylamino)-methyl]-phenyl}-thiazolo[4,5-d]pyrimidine-2,7-diamine (Cpd 55)

4-[(2-isopropoxy-ethylamino)-methyl]-phenylamine was used in place of Compound 1g. Isolated as a trifluoroacetate salt. $^1$H NMR (DMSO-d$_6$) δ 11.21(br s, 1H); 9.65 (s, 1H); 8.85-8.74 (m, 1H); 8.54 (s, 1H); 7.89 (t, J=1.7 Hz, 1H); 7.85 (d, J=8.8 Hz, 2H); 7.71 (d, J=8.0 Hz, 1H); 7.54 (d, J=8.0 Hz, 2H); 7.39 (t, J=8.0 Hz, 1H); 7.22 (d, J=8.0 Hz, 1H); 4.21 (s, 1H); 4.17 (t, J=5.5 Hz, 2H); 3.69-3.55 (m, 3H); 3.13-3.03 (m, 2H); 1.14(d, J=6.1 Hz, 6H). MS 459(MH$^+$).

N$^7$-(5-chloro-2-methoxy-phenyl)-N$^2$-(4-morpholin-4-ylmethyl-phenyl)-thiazolo[4,5-d]pyrimidine-2,7-diamine (Cpd 56)

4-morpholin-4-ylmethyl-phenylamine was used in place of Compound 1g and 5-chloro-2-methoxy-phenylamine was used in place of Compound 1e. Isolated as a trifluoroacetate salt. $^1$H NMR (DMSO-d$_6$) δ 11.19 (s, 1H); 9.91 (br s, 1H); 9.38 (s, 1H); 8.45 (s, 1H); 7.84 (d, J=8.5 Hz, 2H); 7.57-7.49 (m, 3H); 7.38 (dd, J=8.9, 2.5 Hz, 1H); 7.18 (d, J=8.9 Hz, 1H); 4.34 (s, 2H); 3.98 (d, J=12.4 Hz, 2H); 3.63 (t, J=11.1 Hz, 2H); 3.33-3.22 (m, 2H); 3.19-3.04 (m, 2H). MS 483, 485 (MH$^+$).

N$^7$-(3-chloro-phenyl)-N$^2$-(4-morpholin-4-ylmethyl-phenyl)-thiazolo[4,5-d]pyrimidine-2,7-diamine (Cpd 57)

4-morpholin-4-ylmethyl-phenylamine was used in place of Compound 1g and 3-chloro-phenylamine was used in place of Compound 1e. Isolated as a trifluoroacetate salt. $^1$H NMR (DMSO-d$_6$) δ 11.29 (br s, 1H); 10.52 (s, 1H); 9.96 (br s, 1H); 9.72 (s, 1H); 8.56 (s, 1H); 7.94 (t, J=1.9 Hz, 1H); 7.89 (d, J=8.5 Hz, 2H); 7.65 (dd, J=8.2, 1.9 Hz, 1H); 7.55 (d, J=8.5 Hz, 2H); 7.39 (t, J=8.2 Hz, 1H); 7.15 (dd, J=8.2, 1.9 Hz, 1H); 4.35 (s, 2H); 4.05-3.92 (m, 2H); 3.64 (t, J=11.7 Hz, 2H); 3.37-3.23 (m, 2H); 3.21-3.03 (m, 2H). MS 453, 455 (MH$^+$).

4-[7-(3-ethynyl-phenylamino)-thiazolo[4,5-d]pyrimidin-2-ylamino]-N-(2-hydroxy-ethyl)-benzene-sulfonamide (Cpd 58)

4-amino-N-(2-hydroxy-ethyl)-benzenesulfonamide was used in place of Compound 1g. Isolated as a trifluoroacetate salt. $^1$H NMR (DMSO-d$_6$) δ 11.55 (br s, 1H); 9.70 (s, 1H); 8.57 (s, 1H); 7.90 (d, J=8.9 Hz, 2H); 7.78 (m, 3H); 7.63 (d, J=7.9 Hz, 1H); 7.45 (t, J=6.0 Hz, 1H); 7.35 (t, J=7.9 Hz, 1H); 7.21 (d, J=7.9 Hz, 1H); 4.16 (s, 1H); 3.32 (t, J=6.0 Hz, 2H); 2.75 (q, J=6.0 Hz 1H). MS 467 (MH$^+$).

N$^7$-(3-chloro-4-fluoro-phenyl)-N$^2$-(4-{[methyl-(2R)-(tetrahydro-furan-2-ylmethyl)-amino]-methyl}-phenyl)-thiazolo[4,5-d]pyrimidine-2,7-diamine (Cpd 59)

4-{[methyl-(2R)-(tetrahydro-furan-2-ylmethyl)-amino]-methyl}-phenylamine was used in place of Compound 1g and Compound 2g was used in place of Compound 1e. Isolated as a trifluoroacetate salt. $^1$H NMR (DMSO-d$_6$) δ 11.22 (s, 1H); 9.65 (s, 1H); 9.59 (br s, 1H); 8.52 (s, 1H); 8.03 (dd, J=6.8, 2.5 Hz, 1H); 7.87 (d, J=8.6 Hz, 2H); 7.65 (ddd, J=9.1 Hz, 4.4 Hz, 2.5 Hz, 1H); 7.59-7.49 (m, 1H); 7.42 (t, J=9.1 Hz, 1H); 4.37-4.22 (m, 2H); 3.90-3.70 (m, 3H); 3.14-2.98 (m, 2H), 2.80-2.71 (m, 3H); 2.10-1.95 (m, 1H), 1.91-1.76 (m, 2H), 1.58-1.43 (m, 1H). MS 499, 501 (MH$^+$).

N$^7$-(3-chloro-4-fluoro-phenyl)-N$^2$-(4-{[methyl-(2S)-(tetrahydro-furan-2-ylmethyl)-amino]-methyl}-phenyl)-thiazolo[4,5-d]pyrimidine-2,7-diamine (Cpd 60)

4-{[methyl-(2S)-(tetrahydro-furan-2-ylmethyl)-amino]-methyl}-phenylamine was used in place of Compound 1g and Compound 2g was used in place of Compound 1e. Isolated as a trifluoroacetate salt. $^1$H NMR (DMSO-d$_6$) δ 11.21 (s, 1H); 9.64 (s, 1H); 9.58 (br s, 1H); 8.53 (s, 1H); 8.04 (dd, J=6.8, 2.5 Hz, 1H); 7.88 (d, J=8.6 Hz, 2H); 7.66 (ddd, J=9.1 Hz, 4.4 Hz, 2.5 Hz, 1H); 7.59-7.49 (m, 1H); 7.43 (t, J=9.1 Hz, 1H); 4.37-4.22 (m, 2H); 3.90-3.70 (m, 3H); 3.14-2.98 (m, 2H), 2.80-2.71 (m, 3H); 2.10-1.95 (m, 1H), 1.91-1.76 (m, 2H), 1.58-1.43 (m, 1H). MS 499, 501 (MH$^+$).

1-[{4-[7-(3-ethynyl-phenylamino)-thiazolo[4,5-d]pyrimidin-2-ylamino]-benzyl}-(2-hydroxy-propyl)-amino]-propan-2-ol (Cpd 61)

1-[(4-amino-benzyl)-(2-hydroxy-propyl)-amino]-propan-2-ol was used in place of Compound 1g. Isolated as a trifluoroacetate salt. $^1$H NMR (DMSO-d$_6$) δ 11.37 (br s, 1H); 9.77 (s, 1H); 9.07 (br s, 1H); 8.58 (s, 1H); 7.93-7.85 (m, 3H); 7.71 (d, J=7.7 Hz, 1H); 7.60 (d, J=8.3 Hz, 2H); 7.39 (t, J=7.7 Hz, 1H); 7.23 (d, J=7.7 Hz, 1H); 4.56-4.36 (m, 2H); 4.29-4.04 (m, 3H); 3.24-2.85 (m, 4H); 1.23-1.03 (m, 6H). MS 489 (MH$^+$).

N$^2$-(4-{[(2,2-dimethyl-[1,3]dioxolan-4-ylmethyl)-amino]-methyl}-phenyl)-N$^7$-(3-ethynyl-phenyl)-thiazolo[4,5-d]pyrimidine-2,7-diamine (Cpd 62)

4-{[(2,2-dimethyl-[1,3]dioxolan-4-ylmethyl)-amino]-methyl}-phenylamine was used in place of Compound 1g. Isolated as a trifluoroacetate salt. $^1$H NMR (DMSO-d$_6$) δ 12.25 (br s, 1H); 10.65 (s, 1H); 9.61 (br s, 1H); 9.35 (br s, 1H); 8.70 (s, 1H); 7.88-7.85 (m, 3H); 7.70 (d, J=7.9 Hz, 1H); 7.63 (d, J=8.6 Hz, 2H); 7.43 (t, J=7.9 Hz, 1H); 7.30 (d, J=7.9 Hz, 1H); 4.50-4.41 (m, 1H); 4.25 (s, 1H); 4.17 (br s, 2H); 4.06 (dd, J=8.7, 6.2 Hz, 1H); 3.75 (dd, J=8.7, 5.8 Hz, 1H); 3.11-3.03 (m, 1H); 2.92-2.89 (m, 1H); 1.37 (s, 3H); 1.30 (s, 3H). MS 487 (MH$^+$).

N$^7$-(3-ethynyl-phenyl)-N$^2$-(4-{[(methyl-(tetrahydro-pyran-4-yl)-amino]-methyl}-phenyl)-thiazolo[4,5-d]pyrimidine-2,7-diamine (Cpd 63)

(4-amino-benzyl)-methyl-(tetrahydro-pyran-4-yl)-amine was used in place of Compound 1g. Isolated as a trifluoroacetate salt. $^1$H NMR (DMSO-d$_6$) δ 11.21(s, 1H); 9.60 (s, 1H); 9.38 (br s, 1H); 8.53 (s, 1H); 7.93-7.84 (m, 3H); 7.71 (d, J=8.1 Hz, 1H); 7.57 (d, J=8.8 Hz, 2H); 7.38 (t, J=8.1 Hz, 1H); 7.21 (d, J=8.1 Hz, 1H); 4.53-4.43 (m, 1H); 4.21 (s, 1H); 4.08-3.84 (m, 3H); 3.58-3.26 (m, 3H); 2.64 (s, 3H); 2.10-1.64 (m, 4H). MS 471(MH$^+$).

N$^7$-(3-ethynyl-phenyl)-N$^2$-(4-{[(2R)-(tetrahydro-furan-2-ylmethyl)-amino]-methyl}-phenyl)-thiazolo[4,5-d]pyrimidine-2,7-diamine (Cpd 64)

4-{[(2R)-(tetrahydro-furan-2-ylmethyl)-amino]-methyl}-phenylamine was used in place of Compound 1g. Isolated as a trifluoroacetate salt. $^1$H NMR (DMSO-d$_6$) δ 11.18 (s, 1H); 9.61 (s, 1H); 8.89 (br s, 1H); 8.53 (s, 1H); 7.84 (d, J=8.5 Hz, 2H), 7.80 (t, J=2.0 Hz, 1H); 7.71 (dd, J=8.0, 2.0 Hz, 1H); 7.53 (d, J=8.5 Hz, 2H); 7.38 (t, J=8.0 Hz, 1H); 7.21 (dd, J=8.0, 2.0 Hz, 1H), 4.20 (s, 1H); 4.19-4.05 (m, 3H); 3.81 (q, J=6.9 Hz, 1H); 3.73 (q, J=6.9 Hz, 1H); 3.11-2.98 (m, 1H); 2.95-2.79 (m, 1H); 2.07-1.95 (m, 1H); 1.91-1.79(m, 2H), 1.61-1.47(m, 1H). MS 457 (MH$^+$).

N$^7$-(4-fluoro-3-nitro-phenyl)-N$^2$-(4-morpholin-4-ylmethyl-phenyl)-thiazolo[4,5-d]pyrimidine-2,7-diamine (Cpd 65)

4-morpholin-4-ylmethyl-phenylamine was used in place of Compound 1g and 4-fluoro-3-nitro-phenylamine was used in place of Compound 1e. Isolated as a trifluoroacetate salt. $^1$H NMR (DMSO-d$_6$) δ 11.28 (s, 1H); 9.89 (s, 2H); 9.80 (br s, 1H); 8.63 (dd, J=7.1, 3.4 Hz, 1H); 8.57 (s, 1H); 8.22-8.16 (m, 1H); 7.89 (d, J=7.7 Hz, 2H); 7.60 (t, J=9.4 Hz, 2H); 7.54 (d, J=7.7 Hz, 2H); 7.54 (d, J=8.4 Hz, 2H); 4.35 (s, 2H); 4.01-3.94 (m, 2H) 3.67-3.58 (m, 2H); 3.33-3.25 (m, 2H); 3.18-3.07 (m, 2H). MS 482 (MH$^+$).

3-{4-[7-(3-ethynyl-phenylamino)-thiazolo[4,5-d]pyrimidin-2-ylamino]-benzylamino}-propane-1,2-diol (Cpd 66)

Cpd 62 was deprotected with 1N HCl in THF. Isolated as a hydrochloride salt. $^1$H NMR (DMSO-d$_6$) δ 12.12 (br s, 1H); 10.58 (br s, 1H); 9.25-9.16 (m, 1H); 9.06-8.90 (m, 1H); 8.71 (s, 1H); 7.88-7.84 (m, 3H); 7.71 (d, J=7.8 Hz, 1H); 7.64 (d, J=8.5 Hz, 2H); 7.45 (t, J=7.8 Hz, 1H); 7.32 (d, J=7.8 Hz, 1H); 4.27 (s, 1H); 4.18 (br s, 2H); 3.86-3.82 (m, 1H); 3.44 (dd, J=11.0, 4.8 Hz, 1H); 3.30 (dd, J=11.0, 6.6 Hz, 1H); 3.06-3.00 (m, 1H); 2.78-2.75 (m, 1H). MS 447(MH$^+$).

N$^7$-(3-chloro-4-fluoro-phenyl)-N$^2$-(4-{[(2R)-(tetrahydro-furan-2-ylmethyl)-amino]-methyl}-phenyl)-thiazolo[4,5-d]pyrimidine-2,7-diamine (Cpd 67)

4-{[(2R)-(tetrahydro-furan-2-ylmethyl)-amino]-methyl}-phenylamine was used in place of Compound 1g and Compound 2g was used in place of Compound 1e. Isolated as a trifluoroacetate salt. $^1$H NMR (DMSO-d$_6$) δ 11.27 (br s, 1H); 9.78 (s, 1H); 8.56 (s, 1H); 8.02 (dd, J=6.8 Hz, 2.9 Hz, 1H); 7.83 (d, J=8.4 Hz, 2H); 7.65 (ddd, J=9.1 Hz, 4.2 Hz, 2.9 Hz, 1H); 7.54 (d, J=8.4 Hz, 2H); 7.43 (t, J=9.1 Hz, 1H); 4.25-4.07 (m, 3H); 3.81 (q, J=7.3 Hz, 1H); 3.73 (q, J=7.3 Hz, 1H); 3.10-2.99 (m, 1H); 2.95-2.81 (m, 1H); 2.08-1.96 (m, 1H); 1.91-1.79 (m, 2H); 1.62-1.49 (m, 1H). MS 457, 459 (MH$^+$).

N$^7$-[3-chloro-4-(3-fluoro-benzyloxy)-phenyl]-N$^2$-[4-(4-methyl-piperazin-1-ylmethyl)-phenyl]-thiazolo[4,5-d]pyrimidine-2,7-diamine (Cpd 68)

4-(4-methyl-piperazin-1-ylmethyl)-phenylamine was used in place of Compound 1g and 3-chloro-4-(3-fluoro-benzyloxy)-phenylamine was used in place of Compound 1e. Isolated as a hydrochloride salt. $^1$H NMR (DMSO-d$_6$) δ 12.12 (br s, 1H); 10.59 (br s, 1H); 8.69 (s, 1H); 7.89 (d, J=8.5 Hz, 2H); 7.84 (d, J=2.4 Hz, 1H); 7.71 (d, J=8.5 Hz, 2H); 7.58-7.47 (m, 2H); 7.37-7.30 (m, 3H); 7.22 (dt, J=8.5, 2.6 Hz, 1H); 5.30 (s, 2H); 4.42-4.28 (m, 2H); 3.70-3.21 (m, 8H); 2.84 (s, 3H). MS 590, 592 (MH$^+$).

N$^7$-(3-ethynyl-phenyl)-N$^2$-(6-methoxy-pyridin-3-yl)-thiazolo[4,5-d]pyrinidine-2,7-diamine (Cpd 69)

3-amino-6-methoxypyridine was used in place of Compound 1g. Isolated as a hydrochloride salt. $^1$H NMR (DMSO-d$_6$) δ 11.03 (s, 1H); 8.77 (s, 1H); 8.56 (s, 1H); 8.11 (d, J=8.9 Hz, 1H); 7.83 (s, 1H); 7.68 (d, J=7.8 Hz, 1H); 7.47 (t, J=7.8

Hz, 1H); 7.37 (d, J=7.8 Hz, 1H); 6.97 (d, J=8.9 Hz, 1H); 4.29 (s, 1H); 3.18 (s, 3H). MS 424 ($MH^+$).

N7-(3-chloro-4-fluoro-phenyl)-N2-(6-methoxy-pyridin-3-yl)-thiazolo[4,5-d]pyrimidine-2,7-diamnine (Cpd 70)

6-methoxy-pyridin-3-ylamine was used in place of Compound 1g and Compound 2g was used in place of Compound 1e. Isolated as a trifluoroacetate salt. $^1$H NMR (DMSO-$d_6$) δ 11.11 (s, 1H); 9.77 (s, 1H); 8.56 (s, 1H); 8.50 (s, 1H); 8.14 (d, J=8.4 Hz, 1H); 8.04 (d, J=6.4 Hz, 1H); 7.70-7.62 (m, 1H); 7.44 (t, J=8.4 Hz, 1H); 6.95 (d, J=6.4 Hz, 1H); 3.88 (s, 3 H). MS 403, 405 ($MH^+$).

N2-(6-amino-pyridin-3-yl)-N7-(3-chloro-4-fluoro-phenyl)-thiazolo[4,5-d]pyrimidine-2,7-diamine (Cpd 71)

Pyridine-2,5-diamine was used in place of Compound 1g and Compound 2g was used in place of Compound 1e. Isolated as a trifluoroacetate salt. $^1$H NMR (DMSO-$d_6$) δ 11.26 (br s, 1H); 9.68 (s, 1H); 8.69 (d, J=2.4 Hz, 1H); 8.53 (s, 1H); 8.03 (dd, J=6.8, 2.7 Hz, 1H); 7.97 (dd, J=9.4, 2.4 Hz, 1H); 7.91 (br s, 2H); 7.65 (ddd, J=9.0, 4.4, 2.7 Hz, 1H); 7.42 (t, J=9.0 Hz, 1H); 7.06 (d, J=9.4 Hz, 1H). MS 388, 390 ($MH^+$).

N7-(3-ethynyl-phenyl)-N2-[6-(3-morpholin-4-yl-propylamino)-pyridin-3-yl]-thiazolo[4,5-d]pyrimidine-2,7-diamine (Cpd 72)

N2-(3-morpholin-4-yl-propyl)-pyridine-2,5-diamine was used in place of Compound 1g. Isolated as a hydrochloride salt. $^1$H NMR (DMSO-$d_6$) δ 12.30 (br s, 1H); 11.11 (br s, 1H); 10.36 (s, 1H); 8.96 (br s, 1H); 8.64 (s, 2H); 8.05 (dd, J=9.6, 2.0 Hz, 1H); 7.88 (s, 1H); 7.72 (d, J=8.0 Hz, 1H); 7.41 (t, J=8.0 Hz, 1H); 7.26 (d, J=8.0 Hz, 1H); 7.20 (d, J=9.6 Hz, 1H); 4.23 (s, 1H); 4.00-3.79 (m, 4H); 3.60-3.00 (m, 8H); 2.08 (p, J=7.2 Hz, 2H). MS 487 ($MH^+$).

N2-[4-(4-methyl-piperazin-1-ylmethyl)-phenyl]-N7-(4-phenoxy-phenyl)-thiazolo[4,5-d]pyrimidine-2,7-diamine (Cpd 94)

4-(4-methyl-piperazin-1-ylmethyl)-phenylamine was used in place of Compound 1g and 4-phenoxy-phenylamine was used in place of Compound 1e. Isolated as a hydrochloride salt. LC/MS 524($MH^+$).

EXAMPLE 2

4-[7-(3-chloro-4-fluoro-phenylamino)-thiazolo[4,5-d]pyrimidin-2-ylamino]-benzenesulfonamnide (Cpd 73)

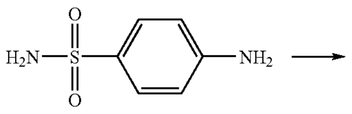

2a

-continued

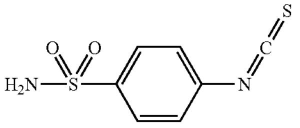

2b 4-amino-benzenesulfonamide Compound 2a (40 g, 240 mmol) in water (400 mL) in the presence of concentrated hydrochloric acid (100 mL) was reacted with thiophosgene (26.8 g, 240 mmol) at r.t. for 30 mins to provide 4-isothiocyanato-benzenesulfonamide Compound 2b (85% yield) (procedure described in McKee R L and Bost R W, *J. Am. Chem. Soc.,* 1946, 68, 2506-7).

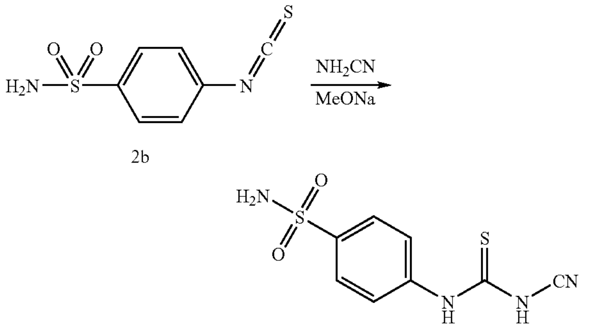

2b

2c

A solution of MeONa in methanol (25% by wt., 17.5 mL, 75 mmol) at 0° C. was added dropwise to a suspension of Compound 2b (10.72 g, 50 mmol) and $NH_2CN$ (2.31 g, 55 mmol) in methanol (230 mL). The mixture was stirred at r.t. until Compound 2b was no longer detected (about 3 hrs) to provide in situ 4-(cyanoaminothiocarbonyl)amino-benzenesulfonamide Compound 2c.

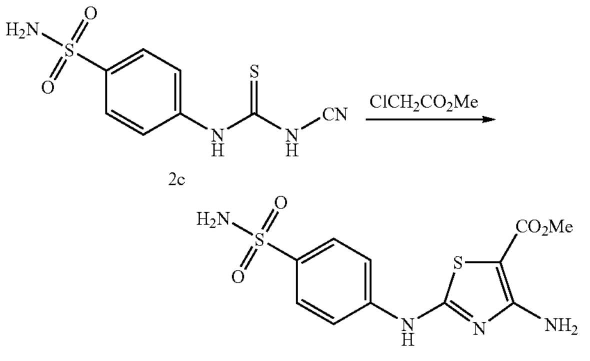

2c

2d

Methyl chloroacetate (5.3 mL, 1.2 eq) at r.t. was added to the mixture containing Compound 2c. The mixture was warmed to about 50-60° C. and stirred for 3 hrs, then stirred at r.t. overnight. The mixture was evaporated to dryness in vacuo and the residual solid was thoroughly washed with water, methylene chloride and a small amount of methanol to give 4-amino-2-(4-sulfamoyl-phenylamino)-thiazole-5-carboxylic acid methyl ester Compound 2d as a yellow powder (9.9 g, 60%). $^1$H NMR (($(CD_3)_2CO$) δ 9.80 (s, br, 1H), 7.80 (m,4H), 6.6 (s, br, 2H), 6.4 (s, br, 2H), 3.7 (s, 3H); MS 329 ($M+H^+$), 351 ($M+Na^+$).

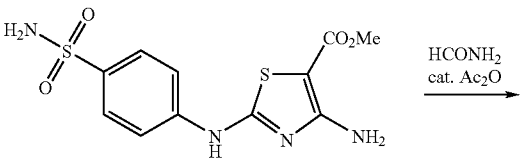

2d

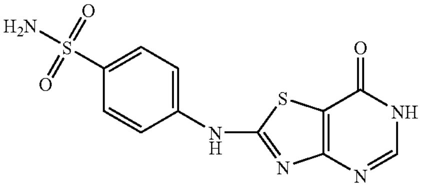

2e

Acetic anhydride (20 drops) was added to a suspension of Compound 2d (5 g, 15.2 mmol) in formamide (25 mL) and stirred at about 170-190° C. until the starting material was no longer detected (about 7 hrs). The mixture was evaporated to dryness in vacuo and the resultant solid was rinsed with water, methylene chloride and a small amount of methanol to give 4-(7-oxo-6,7-dihydro-thiazolo[4,5-d]pyrimidin-2-ylamino)-benzenesulfonamide Compound 2e as a yellow or brown solid (4.36 g, 88%). $^1$HNMR (($(CD_3)_2SO$) δ 12.5 (s, br, 1H), 11.3 (s, br, 1H), 8.10 (s, 1H), 7.80 (m,4H), 7.2 (s, br, 2H); MS 324 ($M+H^+$), 351 ($M+Na^+$).

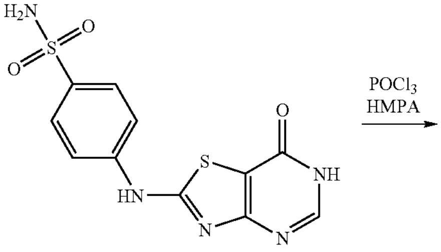

2e

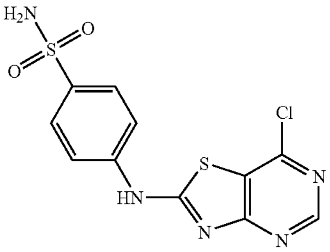

2f $POCl_3$ (25 mL) was added dropwise to a solution of Compound 2e (4.315 g, 13.3 mmol) in HMPA (25 mL) in an ice-water bath. The mixture was stirred at about 70-80° C. for about 4 hrs. $POCl_3$ (50 mL) at r.t. was added and the mixture was stirred at 70-80° C. overnight, then concentrated in vacuo. The residue was placed in an ice-water bath and ice-water was carefully added. The solid was collected by vacuum filtration, then rinsed with water and methylene chloride to provide a crude yellow-green solid (3.27 g, 69%). The solid was purified by column chromatography (eluted with a 10% methanol:methylene chloride mixture) to give 4-(7-chloro-thiazolo[4,5-d]pyrimidin-2-ylamino)-benzenesulfonamide Compound 2f as a yellow powder. $^1$HNMR (($(CD_3)_2SO$) δ 11.8 (s, br, 1H), 8.80 (s, 1H), 7.9 (d, 2H), 7.8 (d, 2H), 7.3 (s, br, 2H); MS 342 ($M+H^+$).

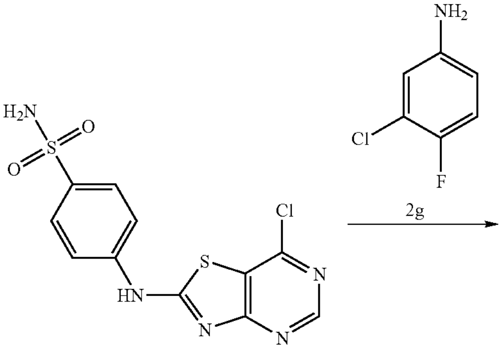

2f

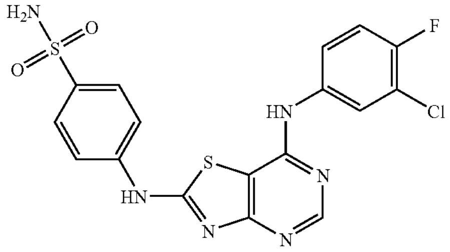

Cpd 73

A suspension of Compound 2f (68 mg, 0.2 mmol) and 3-chloro-4-fluoro-phenylamine Compound 2g (58 mg, 0.4 mmol) in butoxyethanol (1 mL) was stirred at about 180° C. for about 6 hrs then evaporated to dryness in vacuo. The resultant solid was rinsed sequentially with water and methylene chloride to give Compound 73 (21 mg, 20%) as a yellow solid. $^1$HNMR (($(CD_3)_2CO$) δ 10.3 (s, br, 1H), 8.7 (s, 1H), 8.6 (s, 1H), 8.0 (m, 3H), 7.9 (m, 2H), 7.7 (m, 1H), 7.3 (m, 2H), 6.5 (s, 2H); MS 451 ($M+H^+$).

Using the procedure of Example 2 and varying the starting materials, reagent(s) and conditions used, those skilled in the art may prepare other representative compounds of the present invention including, but not limited to:

4-[7-(3-chloro-phenylamino)-thiazolo[4,5-d]pyrimidin-2-ylamno]-benzenesulfonamide (Cpd 74)

3-chloro-phenylamine was used in place of Compound 2g (28%); $^1$H NMR ($(CD_3)_2SO$) δ 11.4 (s, 1H), 9.6 (s, 1H), 8.55 (s, 1H), 8.0-7.85 (m, 5H), 7.70 (d, 1H), 7.40 (t, 1H), 7.30 (s, 2H), 7.10 (d, 1H); MS 433 ($MH^+$).

4-[7-(2,6-difluoro-phenylamino)-thiazolo[4,5-d]pyrimidin-2-ylamino]-benzenesulfonamide (Cpd 75)

2,6-difluoro-phenylamine was used in place of Cpd 2g (37%); $^1$H NMR (($CD_3OD$) δ 8.6 (s, 1H), 7.9 (m, 4H), 7.5 (m, 1H), 7.2 (m, 2H); MS 435 ($MH^+$).

4-[7-(4-chloro-2-fluoro-phenylamino)-thiazolo[4,5-d]pyrimidin-2-ylamino]-benzenesulfonamide (Cpd 76)

4-chloro-2-fluoro-phenylamine was used in place of Compound 2g (14%); $^1$H NMR ($(CD_3)_2CO$) δ 10.3 (s, br, 1H), 8.5 (m, 2H), 8.0 (m, 3H), 7.9 (m, 2H), 7.7 (m, 1H), 7.3 (m, 2H), 6.5 (s, 2H); MS 451 ($MH^+$).

4-[7-(4-bromo-2-fluoro-phenylamino)-thiazolo[4,5-d]pyrimidin-2-ylamino]-benzenesulfonamide (Cpd 77)

4-bromo-2-fluoro-phenylamine was used in place of Compound 2g (13%); $^1$H NMR ($(CD_3)_2CO$) δ 10.4 (s, br, 1H), 8.4 (s, 1H), 8.3 (s, 1H), 8.0 (d, 2H), 7.9 (d, 2H), 7.8 (m, 1H), 7.4 (m, 2H), 6.5 (s, 2H); MS 496 ($MH^+$).

4-[7-(3-bromo-phenylamino)-thiazolo[4,5-d]pyrimidin-2-ylamino]-benzenesulfonamide (Cpd 78)

3-bromo-phenylamine was used in place of Compound 2g (31%); $^1$H NMR ($(CD_3)_2SO$) δ 11.3 (s, 1H), 9.6 (s, 1H), 8.55 (s, 1H), 8.10 (s, 1H), 7.90 (d, 2H), 7.85 (d, 2H), 7.70 (d, 1H), 7.30 (m, 4H); MS 477 ($MH^+$).

4-[7-(3-methyl-phenylamino)-thiazolo[4,5-d]pyrimidin-2-ylamino]-benzenesulfonamide (Cpd 79)

m-tolylamine (also referred to as m-toluidine) was used in place of Compound 2g (44%); $^1$H NMR ($(CD_3)_2SO$) δ 11.3 (s, 1H), 9.4 (s, 1H), 8.6 (s, 1H), 7.9 (d, 2H), 7.80 (d, 2H), 7.5 (d, 2H), 7.30 (m, 3H), 6.9 (d, 1H), 2.3 (s, 3H); MS 413 ($MH^+$).

4-[7-(phenylamino)-thiazolo[4,5-d]pyrimidin-2-ylamino]-benzenesulfonamide (Cpd 80)

phenylamine was used in place of Compound 2g (44%); $^1$H NMR ($(CD_3)_2SO$) δ 11.3 (s, 1H), 9.5 (s, 1H), 8.5 (s, 1H), 8.0 (d, 2H), 7.9 (d, 2H), 7.6 (d, 2H), 7.4 (t, 2H), 7.3 (s, 2H), 7.1 (t, 1H); MS 399 ($MH^+$).

4-[7-(3,5-dichloro-phenylamino)-thiazolo[4,5-d]pyrimidin-2-ylamino]-benzenesulfonamide (Cpd 81)

3,5-dichloro-phenylamine was used in place of Compound 2g (11%); $^1$H NMR ($CD_3OD$) δ 8.56 (s, 1H), 8.00 (d, 2H), 7.90 (d, J=8.9 Hz, 2H), 7.80 (d, 2H), 7.57 (d, 1H), 7.14 (t, 1H); MS 468 ($MH^+$).

4-[7-(4-bromo-3-chloro-phenylamino)-thiazolo[4,5-d]pyrimidin-2-ylamino]-benzenesulfonamide (Cpd 82)

4-bromo-3-chloro-phenylamine was used in place of Compound 2g (20%); $^1$H NMR ($(CD_3)_2SO$) δ 11.35 (s, 1H), 9.73 (s, 1H), 8.57 (s, 1H), 8.17 (s 1H), 7.94 (s, 1H), 7.86 (d, 2H), 7.70 (d, 2H), 7.28 (s, 2H); MS 512 ($MH^+$).

4-[7-(3-chloro-4-(morpholin-4-yl)-phenylamino)-thiazolo[4,5-d]pyrimidin-2-ylamino]-benzenesulfonamide (Cpd 83)

3-chloro-4-morpholin-4-yl-phenylamine was used in place of Compound 2g (51%); $^1$H NMR ($(CD_3)_2SO$) δ 11.35 (s, 1H), 9.73 (s, 1H), 8.57 (s, 1H), 8.17 (s 1H), 7.94 (s, 1H), 7.86 (d, 2H), 7.70 (d, 2H), 7.28 (s, 2H); MS 519 ($MH^+$).

4-[7-(3-(morpholin-4-yl)methyl-phenylamino)-thiazolo[4,5-d]pyrimidin-2-ylamino]-benzenesulfonamide (Cpd 84)

methyl-(4-morpholin-4-yl-phenyl)-amine was used in place of Compound 2g (20%); $^1$H NMR ($(CD_3)_2SO$) δ 11.35 (s, 1H), 9.50 (s, 1H), 8.47 (s, 1H), 7.93 (d, 2H), 7.84 (d, 2H), 7.65 (d, 1H), 7.53 (s, 1H), 7.30 (m, 3H), 7.04 (d, 1H), 3.58 (t, J=8.9 Hz, 4 H); MS 498 ($MH^+$).

4-[7-(4-(morpholin-4-yl)ethyl-phenylamino)-thiazolo[4,5-d]pyrimidin-2-ylamino]-benzenesulfonamide (Cpd 85)

ethyl-(4-morpholin-4-yl-phenyl)-amine was used in place of Compound 2g (46%); $^1$H NMR ($(CD_3)_2SO$) δ 11.35 (s, 1H), 9.44 (s, 1H), 8.44 (s, 1H), 7.94 (d, 2H), 7.84 (d, 2H), 7.52 (d, 2H), 7.28 (s, 2H), 7.21 (d, 2H), 3.58 (t, 4H), 2.73 (t, 2H), 2.53 (s, 2H), 2.43 (s, 4H); MS 512 ($MH^+$).

4-[7-(4-(morpholin-4-yl)-phenylamino)-thiazolo[4,5-d]pyrimidin-2-ylamino]-benzenesulfonamide (Cpd 86)

4-morpholin-4-yl-phenylamine was used in place of Compound 2g (17%); $^1$H NMR ($(CD_3)_2SO$) δ 11.25 (s, 1H), 9.32 (s, 1H), 8.39 (s, 1H), 7.91 (d, 2H), 7.82 (d, 2H), 7.38 (d, 2H), 7.27 (s, 2H), 6.96 (d, 2H), 3.75 (t, 4H), 3.11 (t, 4H); MS 484 ($MH^+$).

4-[7-(4-methoxy-3-(morpholin-4-yl)methyl-phenylamino)-thiazolo[4,5-d]pyrimidin-2-ylamino]-benzenesulfonamide (Cpd 87)

(4-methoxy-3-morpholin-4-yl-phenyl)-methyl-amine was used in place of Compound 2g (36%); $^1$H NMR ($(CD_3)_2SO$) δ 11.21 (s, 1H), 9.38 (s, 1H), 8.40 (s, 1H), 7.92 (d, J=8.9 Hz, 2H), 7.83 (d, 2H), 7.46 (d, 2H), 7.27 (s, 2H), 7.01 (d, 1H), 3.81 (s,3H), 3.57 (s, 4H), 3.48 (s, 2H), 2.42 (s, 4H); MS (ESI) 528 ($M+H^+$).

EXAMPLE 3

$N^7$-(3-chloro-4-fluoro-phenyl)-$N^2$-phenyl-thiazolo[4,5-d]pyrimidine-2,7-diamine (Cpd 88)

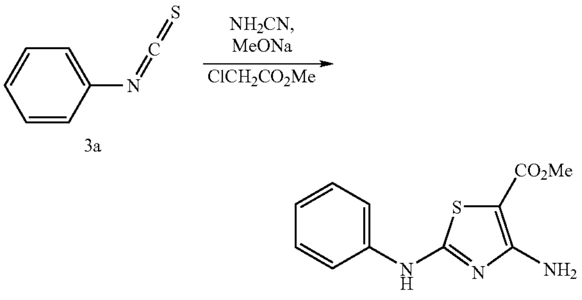

3a
3b

A 0.5 M solution of sodium methoxide in methanol (44.4 mL, 22.19 mmol) was added dropwise to a suspension of isothiocyanato-benzene Compound 3a (2.0 g, 14.79 mmol) and $NH_2CN$ (0.684 g, 16.27 mmol) in methanol (50 mL) at 0° C. The mixture was stirred at r.t. until Compound 3a was no longer detected (about 3 hrs). Methyl chloroacetate (1.56 mL, 17.75 mmol) was added at r.t. and the mixture was warmed to 50-60° C. and stirred at 50-60° C. for about 3 hrs, then stirred at r.t. overnight. The mixture was evaporated to dryness in vacuo and the resultant solid was thoroughly washed with water, methylene chloride and a small amount of methanol to give 4-amino-2-phenylamino-thiazole-5-carboxylic acid methyl ester Compound 3b (1.12 g, 60%) as a yellow powder. MS 250 ($M+H^+$), 248 ($M-H^+$)

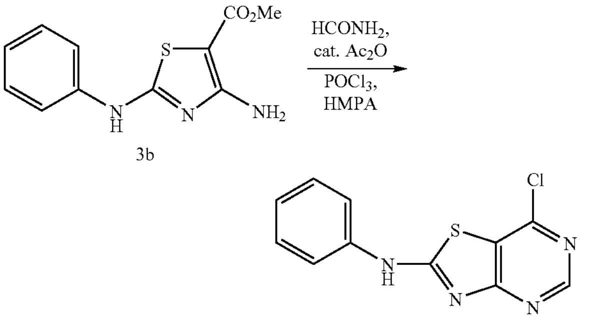

3b
3c

A catalytic amount of $Ac_2O$ (acetic anhydride) (25 drops) was added to a suspension of Compound 3b (5.33 g, 21.4 mmol) in $HCONH_2$ (formamide) (25 mL) and the mixture was stirred at 180° C. for about 16 hrs. The mixture was concentrated by distillation and the residual solids were suspended in $POCl_3$ (100 mL) and stirred at 80° C. for 16 hrs. The mixture was evaporated to dryness in vacuo and purified via column chromatography (2% methanol:dichloromethane) to give (7-chloro-thiazolo[4,5-d]pyrimidin-2-yl)-phenyl-amine Compound 3c (0.402 g, 29% yield) as a yellow solid. MS 263($M+H^+$), 261 ($M-H^+$)

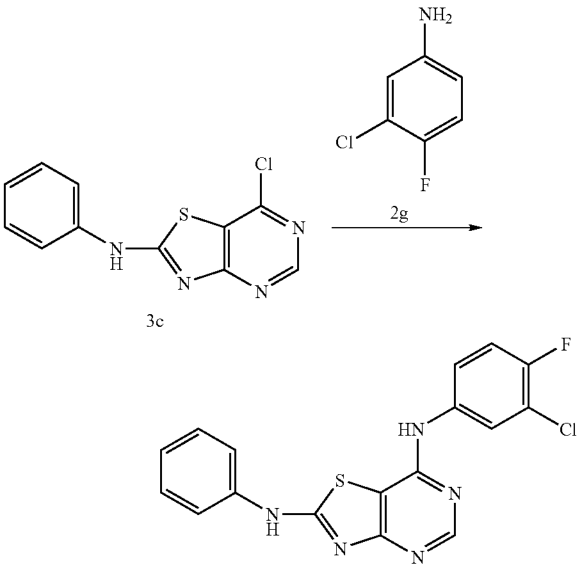

3c
Cpd 88

A suspension of Compound 3c (39.5 mg, 0.15 mmol) and 3-chloro-4-fluoro-phenylamine Compound 2g (43.8 mg, 0.30 mmol) in butoxyethanol (1 mL) was stirred at about 180° C. for about 6 hrs, then evaporated to dryness in vacuo. The resultant solid was rinsed sequentially with water and methylene chloride to give Compound 88 (37.9 mg, 68%) as a white solid. $^1H$ NMR ($(CD_3)_2SO$) δ 10.13 (s, 1H), 8.61 (s, 1H), 8.02 (d, 1H), 7.77 (d, 2H), 7.65 (m, 1H), 7.44 (m, 3H), 7.15 (t, 1H); MS 372 ($M+H^+$).

Using the procedure of Example 3 and varying the starting materials, reagent(s) and conditions used, those skilled in the art may prepare other representative compounds of the present invention including, but not limited to:

$N^7$-(3-chloro-phenyl)-$N^2$-phenyl-thiazolo[4,5-d]pyrirnidine-2,7-diamine (Cpd 89)

3-chloro-phenylamine was used in place of Compound 2g (68%); $^1H$ NMR ($(CD_3)_2SO$) δ 11.00 (s, 1H), 9.55 (s, 1H), 8.52 (s, 1H), 7.94 (t, 1H), 7.77 (d, 2H), 7.65 (m, 1H), 7.39 (m, 3H), 7.12 (m, 2H); MS 354 ($M+H^+$), 352 ($M-H^+$).

$N^7$-(3-bromo-phenyl)-$N^2$-phenyl-thiazolo[4,5-d]pyrimidine-2,7-diamine (Cpd 90)

3-bromo-phenylamine was used in place of Compound 2g (51%); $^1H$ NMR ($(CD_3)_2SO$) δ 11.00 (s, 1H), 9.53 (s, 1H), 8.52 (s, 1H), 8.06 (t, 1H), 7.74 (m, 3H), 7.42 (t, 1H), 7.28 (m, 2H), 7.12 (t, 1H); MS 398 ($M+H^+$).

$N^7$-(3,5-dichloro-phenyl)-$N^2$-phenyl-thiazolo[4,5-d]pyrimidine-2,7-diamine (Cpd 91)

3,5-dichloro-phenylamine was used in place of Compound 2g (32%); $^1H$ NMR ($(CD_3)_2SO$) δ 11.00 (s, 1H), 9.66 (s, 1H), 8.57 (s, 1H), 7.92 (d, 2H), 7.77 (d, 2H), 7.42 (t, 2H), 7.22 (t, 1H), 7.13 (t, 1H); MS 387 ($M-H^+$).

EXAMPLE 4

4-[7-(3-chloro-4-fluoro-phenylamino)-thiazolo[4,5-d]pyrimidin-2-ylamino]-benzonitrile (Cpd 92)

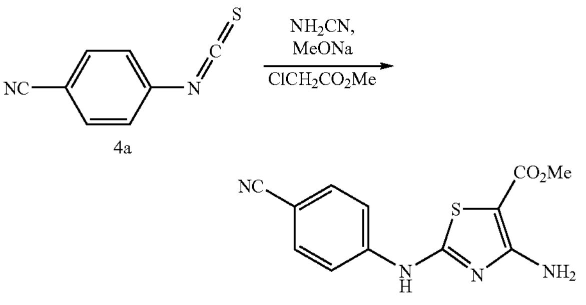

4a
4b

A solution of MeONa in methanol (25% by wt., 2.0 mL, 9.36 mmol) was added dropwise to a suspension of 4-isothiocyanato-benzonitrile Compound 4a (1.0 g, 6.24 mmol) and $NH_2CN$ (0.289 g, 6.87 mmol) in methanol (25 mL) at 0° C. The mixture was stirred at r.t. until Compound 4a was no longer detected (about 3 hrs). Methyl chloroacetate (0.657 mL, 7.49 mmol) was added at r.t. and the mixture was stirred at 50-60° C. for 3 hrs, then at r.t. overnight. The mixture was evaporated to dryness in vacuo, then the residual solid was thoroughly washed with water, methylene chloride and a small amount of methanol to give 4-amino-2-(4-cyano-phenylamino)-thiazole-5-carboxylic acid methyl ester Compound 4b (1.06 g, 62%) as a yellow powder. MS 273 (M−H$^+$)

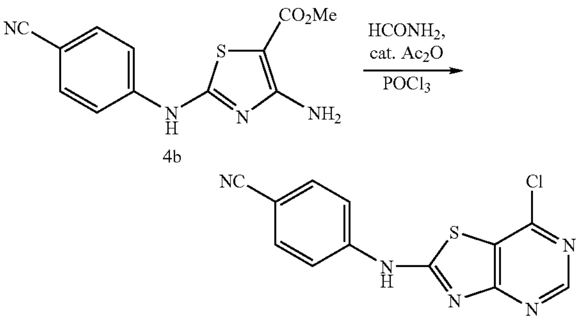

4b

4c

Acetic anhydride (25 drops) was added to a suspension of Compound 4b (1.062 g, 3.87 mmol) in formamide (25 mL). The mixture was stirred at 180° C. for 16 hrs, concentrated by distillation, then the residual solids were suspended in $POCl_3$ (100 mL) and stirred at 80° C. for 16 hrs. After evaporation to dryness in vacuo, purification by column chromatography (2% methanol:dichloromethane) gave 4-(7-chloro-thiazolo[4,5-d]pyrimidin-2-ylamino)-benzonitrile Compound 4c as a yellow solid (0.120 g, 11% yield). MS 286 (M−H$^+$)

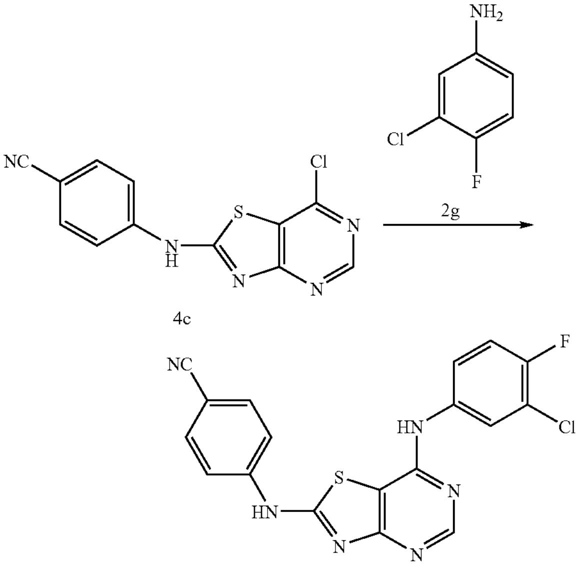

4c

Cpd 92

A suspension of Compound 4c (50.0 mg, 0.17 mmol) and 3-chloro-4-fluoro-phenylamine Compound 2g (43.8 mg, 0.30 mmol) in butoxyethanol (1 mL) was stirred at about 180° C. for about 6 hrs then evaporated to dryness in vacuo. The resultant solid was rinsed sequentially with water and methylene chloride to give Compound 92 (31.6 mg, 46%) as an off-white solid. $^1$H NMR (($(CD_3)_2SO$) δ 11.42 (s, 1H), 9.66 (s, 1H), 8.54 (s, 1H), 8.03 (m, 1H), 7.97 (d, 2H), 7.87 (d, 2H), 7.66 (m, 1H), 7.42 (t, 1H); MS 395 (M−H$^+$).

Using the procedure of Example 4 and varying the starting materials, reagent(s) and conditions used, those skilled in the art may prepare other representative compounds of the present invention including, but not limited to:

4-[7-(3-chloro-phenylamino)-thiazolo[4,5-d]pyrimidin-2-ylamino]-benzonitrile (Cpd 93)

3-chloro-phenylamine was used in place of Compound 2g (52%). $^1$H NMR $(CD_3)_2SO$) δ 11.42 (s, 1H), 9.67 (s, 1H), 8.56 (s, 1H), 7.96 (m, 3H), 7.87 (d, 2H), 7.65 (m, 1H), 7.38 (t, 1H), 7.13 (m, 1H); MS 377 (M−H$^+$).

BIOLOGICAL EXAMPLES

The ability of the compounds to treat or ameliorate protein kinase mediated disorders was determined using the following procedures.

EXAMPLE 5

EGFR Kinase Assay

The EGFR kinase used was a fusion of Glutathione-S-Transferase (GST) and a PCR amplified intracellular portion of EGFR (NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a, GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf 9 cells and the supernatant containing the baculovirus was collected. The GSTEGFR protein was purified using large cultures of Sf 9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating polyGluTyr (128 mg) (Sigma, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 μM final from 10 mM stock), biotinylated polyGluTyr (10 μg/μL stock), γ-$^{33}$P ATP (10 μCi/μL stock) and water was added to each well (90 μL/well) of a Streptavidin Flashplate (Perkin Elmer, Wellesley, Mass.).

Test compound in 100% DMSO (2 μL) was added to the appropriate wells. Diluted GSTEGFR (1:300 dilution in 50 mM Tris at pH 8.0 and 0.1% bovine serum albumin) (10 μL) was added to the wells to initiate the reactions.

The plates were incubated at 30° C. for 1 hr with shaking. The reacted contents were removed and the plates were sequentially washed three times with a 1×PBS stop buffer (300 μL without Magnesium and Calcium) and 100 mM EDTA. After the final wash, the same stop buffer (200 μL) was added to the wells. The plates were then sealed and read on the TopCount scintillation counter.

Test compounds were assayed in triplicate at 16 concentrations at half-log dilutions starting at 200 uM. A maximum and minimum signal for the assay was determined on each plate. The percent inhibition of a test compound was calculated according to the formula $$\left[\frac{(\text{max signal} - \text{test compound})}{(\text{max signal} - \text{min signal})}\right](100) = \%\ \text{inhibition}$$

For a series of test concentrations, the $IC_{50}$ was derived by graphing percent inhibition against the log of the concentrations tested for a given compound. The $IC_{50}$ results are showm in Table 1. For those compounds without an $IC_{50}$, the percent inhibition result are shown at a test concentration of 2 μM.

TABLE 1

| EGFR $IC_{50}$ (nM) | |
|---|---|
| Cpd | $IC_{50}$ (avg) |
| 1 | 44 |
| 2 | 8.9 |
| 3 | 119 |
| 4 | 21.7 |
| 5 | 18.4 |
| 6 | 20 |
| 7 | 13 |
| 8 | 34.7 |
| 9 | 18 |
| 10 | 12.3 |
| 11 | 12.8 |
| 12 | 117 |
| 13 | 95 |
| 14 | 59.4 |
| 15 | 90.1 |
| 16 | 165 |
| 17 | 4.2 |
| 18 | 15.4 |
| 19 | 6 |
| 20 | 49.3 |
| 21 | 13.3 |
| 22 | 9.3 |
| 23 | 6.3 |
| 24 | 21.6 |
| 25 | 10.9 |
| 26 | 11.8 |
| 27 | 15 |
| 28 | 57 |
| 29 | 27.8 |
| 30 | 5.5 |
| 31 | 10.3 |
| 32 | 20.8 |
| 33 | 25.3 |
| 34 | 6.4 |
| 35 | 30 |
| 36 | 1019 |
| 37 | 25.3 |
| 38 | 28.5 |
| 39 | 2.5 |
| 40 | 9 |
| 41 | 10 |
| 42 | 5.42 |
| 43 | 7.8 |
| 44 | 10 |
| 45 | 22.5 |
| 46 | 15.5 |
| 47 | 18.2 |
| 48 | 9 |
| 49 | 11.8 |
| 50 | 13 |
| 51 | 918 |
| 52 | 698 |
| 53 | 7.73 |
| 54 | 10 |

TABLE 1-continued

| EGFR $IC_{50}$ (nM) | |
|---|---|
| Cpd | $IC_{50}$ (avg) |
| 55 | 8.25 |
| 56 | 36 |
| 57 | 7 |
| 58 | 6.5 |
| 59 | 11 |
| 60 | 23.9 |
| 61 | 27.5 |
| 62 | 6.95 |
| 63 | 10.7 |
| 64 | 3.96 |
| 65 | 43.4 |
| 66 | 7.28 |
| 67 | 3.7 |
| 68 | 20.3 |
| 69 | 28.6 |
| 70 | 19.6 |
| 71 | 44 |
| 72 | 28.2 |
| 73 | 9.52 |
| 74 | 6.6 |
| 75 | 187 |
| 76 | 40.2 |
| 77 | 87 |
| 78 | 10.5 |
| 79 | 14.3 |
| 80 | 82.5 |
| 81 | 116 |
| 82 | 5 |
| 83 | 3800 |
| 84 | 3300 |
| 85 | 10100 |
| 86 | 17900 |
| 87 | 13% |
| 88 | 59.3 |
| 89 | 27.1 |
| 90 | 16.5 |
| 91 | 733 |
| 92 | 15.4 |
| 93 | 25.5 |
| 94 | 319 |

EXAMPLE 6 c-Src Kinase Assay

A mixure of a 10× kinase buffer (80 mM MOPS at pH 7.0, 2 mM EDTA and 100 mM Magnesium Chloride), ATP (5 μM final from a 10 mM stock), a Cdc2 peptide KVEKIGEG-TYGVVYK (100 μM final from a 2.5 mM stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted c-Src kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%), and 1 mg/mL bovine serum albumin) (2.5 μL) was added to the wells to initiate the reactions. The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

Percent inhibition was derived according to the procedure described in Example 5. The results for those compounds tested are shown in Table 2 at a test concentration of 1 μM.

TABLE 2

| c-SRC % Inhibition | |
|---|---|
| Cpd | % Inh |
| 64 | 21% |
| 66 | 15% |
| 73 | 65% |

EXAMPLE 7

Lyn Kinase Assay

A mixture of a 10× kinase buffer (500 mM MOPS at pH 7.5, 1 mM EGTA, 1 mM Sodium Vanadate, 1% β-mercaptoethanol and 100 mM Magnesium Acetate), ATP (5 μM final from a 10 mM stock), polyGluTyr (0.1 mg/mL final from a 1 mg/mL stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted Lyn kinase (human) (Upstate biotechnology, Lake Placid, N.Y) (diluted in a buffer consisting of 50 mM Tris at pH 7.5, 0.1 mM EGTA, Sodium Vanadate (0.1 mM), β-mercaptoethanol (0.1%) and 1 mg/mL bovine serum albumin) (2.5 μL) was added to the wells to initiate the reactions.

The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

Percent inhibition was derived according to the procedure described in Example 5. The results for those compounds tested are shown in Table 3 at a test concentration of 1 μM.

TABLE 3

| Lyn % Inhibition | |
|---|---|
| Cpd | % Inh |
| 64 | 17% |
| 66 | 25% |

EXAMPLE 8

HER-2 Kinase Assay

The HER-2 kinase used was purified at Proqinase (Freiburg, Germany) from a construct that consisted of a fusion of GST (Glutathione-S-Transferase), HIS6-Thrombin and the nucleotides encoding amino acids 679 to 1255 of HER-2.

A mixture of a 10× kinase reaction buffer (600 mM Hepes at pH 7.5, 30 mM Magnesium Chloride, 0.03 mM Sodium Vanadate and 500 μg/nL PEG 20,000), DTT (1.2 mM final from a 10 mM stock), ATP (1 μM from a 10 mM stock), biotinylated polyGluTyr (1.5 ng/μL final from stock of 1 μg/μL prepared by Upstate Biotechnologies, Lake Placid, N.Y.), Manganese Chloride (3 mM final from a 1 M stock), γ-$^{33}$P-ATP (10 μCi/μL stock) and water (70 μL/well) was added to each well of a Streptavidin Flashplate (Cat. # SMP103, NEN, Boston, Mass.).

Test compound stock (1 μL) was added to the appropriate wells. Diluted GSTHER2 kinase (6.7 ng/μL diluted into 50 mM Tris-HCl at pH 8.0 and 0.1% bovine serum albumin) (30 μL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 μL) and 100 mM EDTA. After the final wash, the same stop buffer (200 μL) was again added to the wells. The plates were then sealed and read on the TopCount scintillation counter.

The $IC_{50}$ was derived according to the procedure described in Example 5. The $IC_{50}$ results are shown in Table 4.

TABLE 4

| HER-2 $IC_{50}$ (μM) | |
|---|---|
| Cpd | $IC_{50}$ |
| 68 | 0.276 |
| 94 | 1.87 |

EXAMPLE 9 c-Abl Kinase Assay

A mixture of a 10× kinase buffer (80 mM MOPS at pH 7.0, 2 mM EDTA and 100 mM Magnesium Acetate), ATP (5 μM final from a 10 mM stock), a peptide EAIYAAPFAKKK (50 μM final from a 0.5 mM stock), γ-$^{33}$P ATP (10 μCi/μL stock) and water is added to each well (20 μl/well) of a Streptavidin Flashplate.

Test compound in 100% DMSO (0.5 μL) is added to the appropriate wells. Diluted c-Abl kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%) and 1 mg/ml bovine serum albumin) (2.5 μL) is added to the wells to initiate the reactions.

The reaction plates are incubated at 30° C. for 40 min. The reaction is terminated by the addition of a 3% phosphoric acid solution (5 μL). The reaction product (10 μL) is spotted onto a P30 filtermat and is washed for 5 minutes in phosphoric acid (75 mM). The wash sequence is repeated two more times and is followed with one final wash in methanol. The plates are then dried, sealed and read on the TopCount scintillation counter after 30 μL scintillation fluid is added.

The 1% percent inhibition value for Compound 64 was derived according to the procedure described in Example 5 at a test concentration of 1 μM.

EXAMPLE 10

Cell Proliferation Inhibition Assay

The ability of a test compound to inhibit unregulated cell proliferation may be determined by measuring incorporation of $^{14}$C-labelled thymidine into newly synthesized DNA within cell lines derived from carcinomas originating from several tissues. Accordingly, the anti-proliferative effect of a compound on cells with a variety of phenotypes may be determined.

Carcinoma cell lines include those such as HeLa cervical adenocarcinoma (American Type Culture Collection (ATCC), Virginia, Cat. #CCL-2), A375 malignant melanoma (ATCC CRL-1619), SK-OV-3 ovarian adenocarcinoma (ATCC HTB-77), HCT-116 colon carcinoma (CCL-247), PC-3 prostate adenocarcinoma (ATCC CRL-1435), and MDA-MB-231 (Xenogen Corp.)

The carcinoma cells are trypsinized and counted. The cells (3000-8000 count) are added to each well of a 96-well CytoStar tissue culture treated scintillating microplate (Amersham #RPNQ0160) in complete medium (100 μL) and the plate is then incubated in complete medium for 24 hrs at 37° C. in an inert atmosphere containing 5% $CO_2$. Test compound (1 μL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) and complete medium (20 uL to provide 0.2 μCi/well) is then added to each well and the plate is incubated for a third 24 hr period at 37° C. in an atmosphere containing 5% $CO_2$. The plate contents are then discarded, the plate is washed twice with PBS (200 μL) and then PBS (200 μL) is added to each well. The plate is sealed and the degree of methyl $^{14}$C-thyrnidine incorporation is quantified on a Packard Top Count.

HeLa and A375 Cell Proliferation Inhibition $IC_{50}$ (μM)

| HeLa and A375 Cell Proliferation Inhibition $IC_{50}$ (μM) | | |
|---|---|---|
| Cpd | HeLa | A375 |
| 18 | >100 | >100 |
| 68 | 2.189 | 2.031 |

SK-OV-3 Cell Proliferation Inhibition $IC_{50}$ (μM)

| SK-OV-3 Cell Proliferation Inhibition $IC_{50}$ (μM) | |
|---|---|
| Cpd | SK-OV-3 |
| 2 | 0.49 |
| 4 | 0.62 |
| 10 | 0.56 |
| 11 | 0.6 |
| 17 | 0.62 |
| 18 | 0.57 |

SK-OV-3 Cell Migration Inhibition $IC_{50}$ (μM)

| SK-OV-3 Cell Migration Inhibition $IC_{50}$ (μM) | |
|---|---|
| Cpd | SK-OV-3 Migration |
| 4 | 0.735, 0.520 |
| 18 | 0.186, 0.156, 0.141 |
| 31 | 0.138, 0.180, 0.191 |
| 32 | >5 |
| 33 | 0.252 |
| 34 | 0.210 |
| 35 | 0.474, 0.380 |

HCT-116 Cell Proliferation Inhibition $IC_{50}$ (μM)

| HCT-116 Cell Proliferation Inhibition $IC_{50}$ (μM) | |
|---|---|
| Cpd | HCT-116 |
| 18 | >100 |
| 68 | 3.085 |

EXAMPLE 11

In Vivo Models—Inhibution Tumor Growth

The ability of a test compound to inhibit unregulated growth of human tumor cells in vivo may be evaluated by implanting human tumor cells into the hindflank of athymic mice, administering a test compound and then quantifying any change in tumor size.

Human epidermoid A431 carcinoma cells ($10^6$ count) are implanted subcutaneously into the hindflank of female athymic mice (Charles River) and allowed to grow for 6-10 days. After a measurable tumor is established (as determined by baseline caliper measurement), the animal is administered an oral dose of the test compound (in 10% solutol) daily for a period of 30 days. Tumor size is measured every five days and the degree of inhibition is determined by comparing drug-treated animals to vehicle-treated animals.

Variations of this method are intended to include intraperitoneal injection or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. The compound of the following formula:

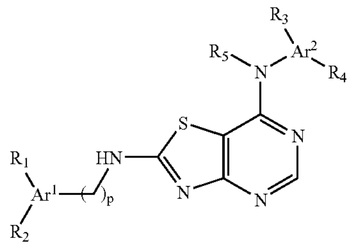

wherein p is 0, 1, 2 or 3, $R_5$ is hydrogen or $C_{1-8}$alkyl, $Ar^1$ is phenyl, $R_1$ and $R_2$ is each independently selected from the group consisting of (1) hydrogen, (2) $C_{1-8}$alkyl, (3) $C_{1-8}$alkoxy, wherein (2) and (3) is each optionally substituted with a substituent selected from the group consisting of (i) heteroaryl, (ii) heterocyclyl, wherein (i) and (ii) are optionally substituted with one or two substituents independently selected from the group consisting of (a) $C_{1-8}$alkyl, (c) $C_{1-8}$alkyl($C_{1-8}$alkoxy), (d) $C_{1-8}$alkyl(hydroxy)$_{1-3}$, (e) $CO_2$($C_{1-8}$alkyl), (g) $C_{1-8}$alkyl(amino), and (h) aryl optionally substituted with halogen, and (iii) amino optionally mono or disubstituted with a substituent independently selected from the group consisting of (a) $C_{1-8}$alkyl, (b) $C_{1-8}$alkyl($C_{1-8}$alkoxy), (c) $C_{1-8}$alkyl(hydroxy)$_{1-3}$, (d) $C_{3-8}$cycloalkyl, (e) heterocyclyl optionally substituted with one or two $C_{1-8}$alkyl substituents, and (f) $C_{1-8}$alkyl(heterocyclyl) optionally substituted on heterocyclyl with one or two $C_{1-8}$alkyl substituents, (4) amino optionally mono or disubstituted with $C_{1-8}$alkyl (heterocyclyl), (5) cyano, (6) hydroxy, (7) heterocyclyl, (8) $SO_2$(heterocyclyl), (9) C(O)amino optionally mono or disubstituted on amino with $C_{1-8}$alkyl, and

(10) $SO_2$(amino) optionally mono or disubstituted on amino with a substituent independently selected from the group consisting of (i) $C_{1-8}$alkyl($C_{1-8}$alkoxy), (ii) $C_{1-8}$alkyl(amino) optionally mono or disubstituted on amino with $C_{1-8}$alkyl, (iii) $C_{1-8}$alkyl(hydroxy)$_{1-3}$, and (iv) $C_{1-8}$alkyl(heterocyclyl), $Ar^2$ is phenyl, and $R_3$ and $R_4$ is each independently selected from the group consisting of (1) hydrogen, (2) $C_{1-8}$alkyl, (3) $C_{2-8}$alkynyl, (4) $C_{1-8}$alkoxy, (5) $C_{1-8}$alkoxy(aryl), wherein aryl is optionally substituted with one, two or three halogen substinients, (5) cyano, (6) halogen, (7) nitro, and (8) heterocyclyl.

2. The compound of claim 1 wherein the compound is selected from the group consisting of:

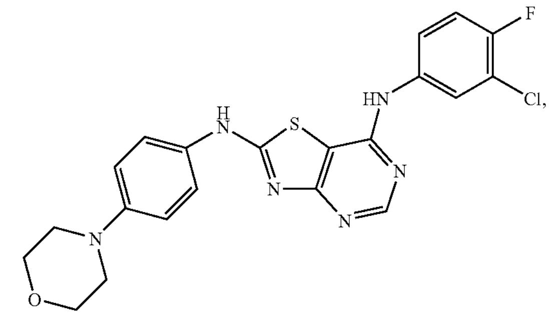

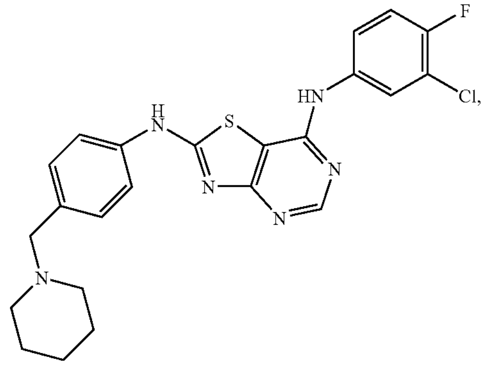

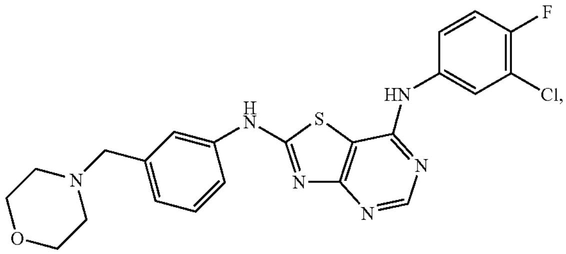

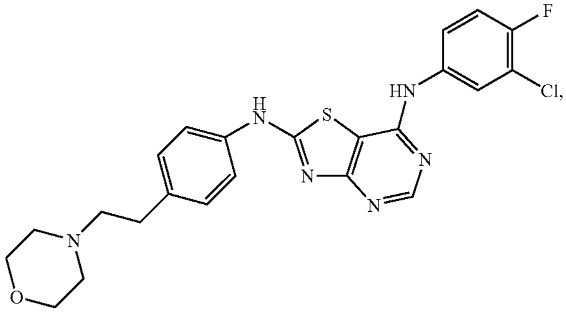

-continued
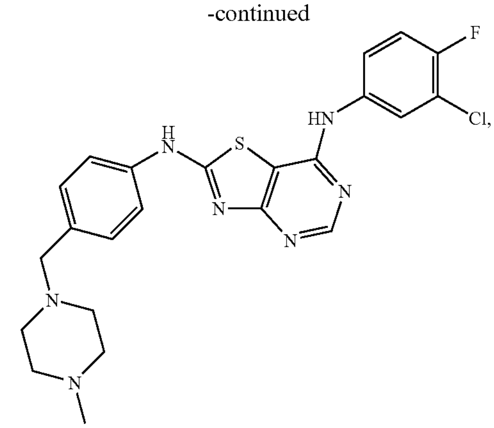
,
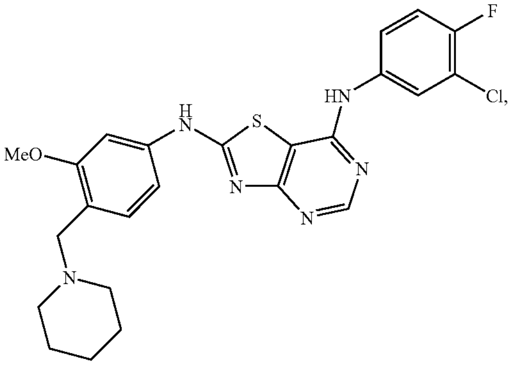
,
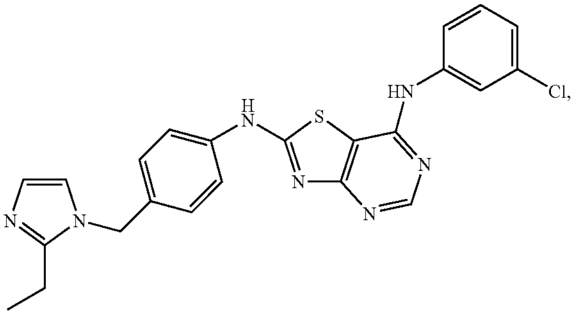
,
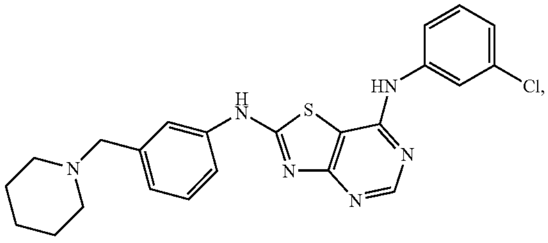
,
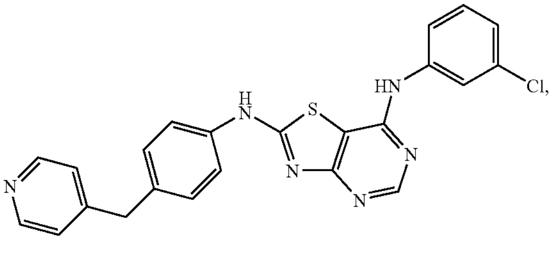
,
-continued
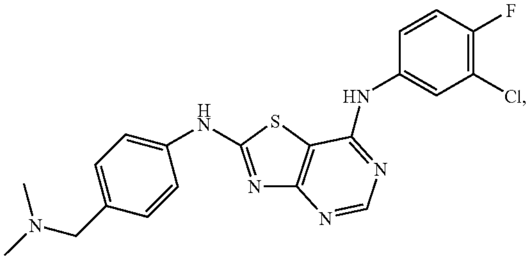
,
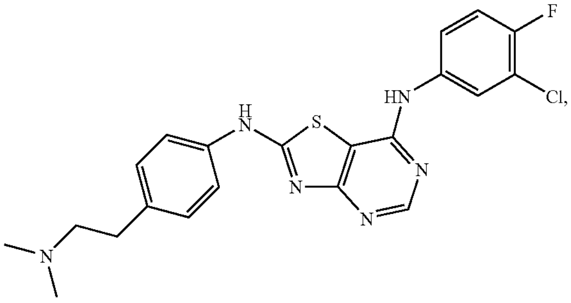
,
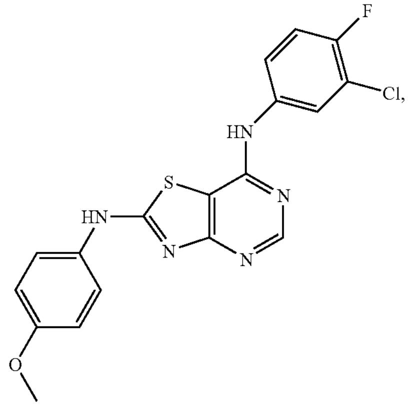
,
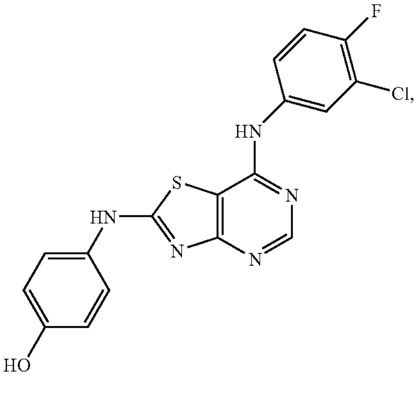

-continued
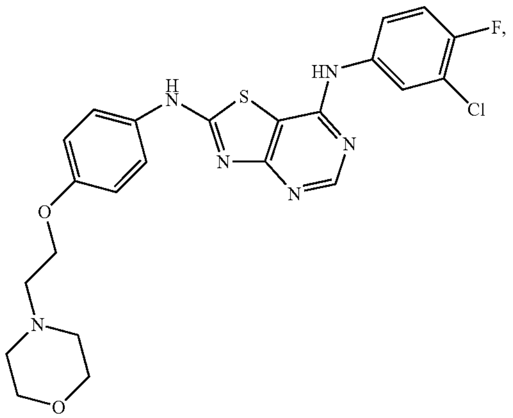
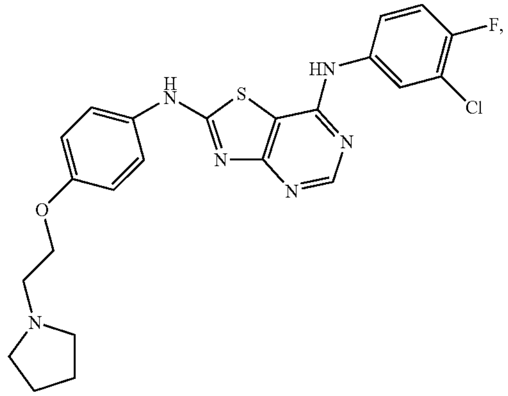
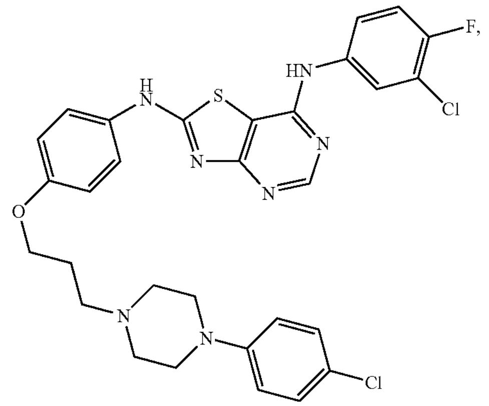
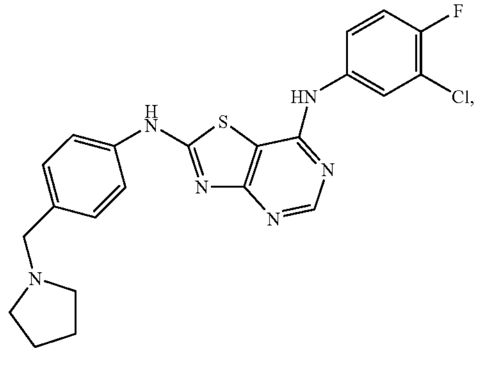
-continued
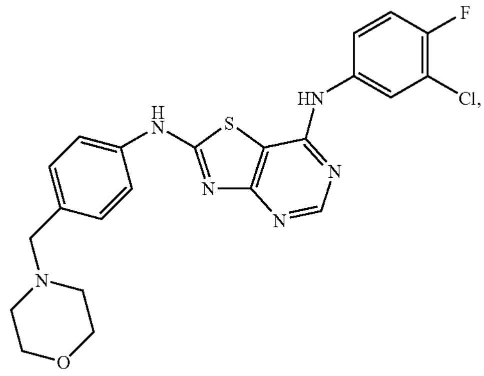
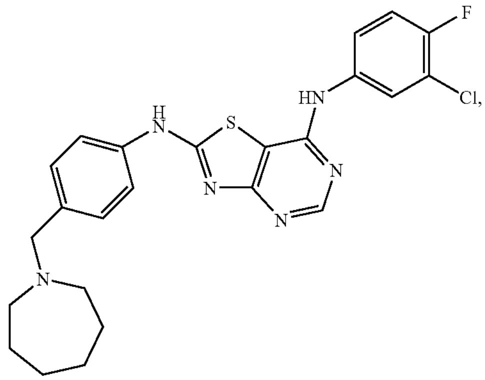
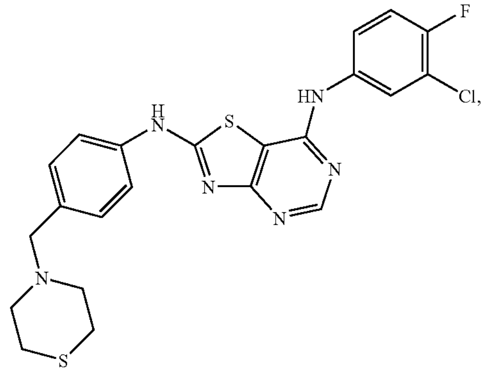
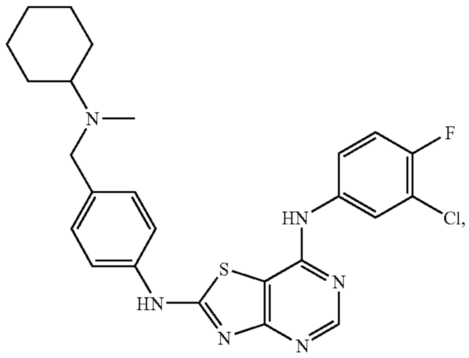

-continued
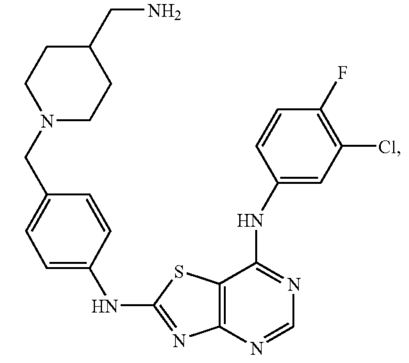
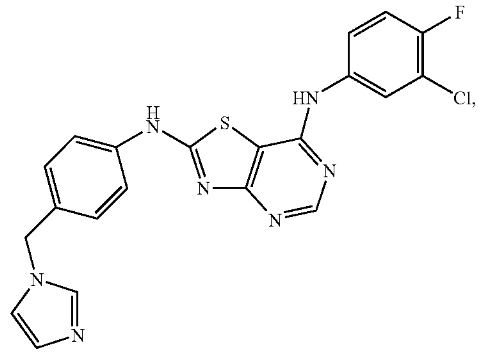
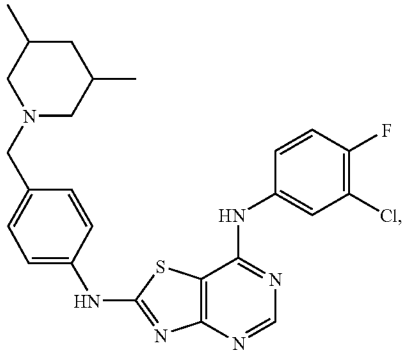
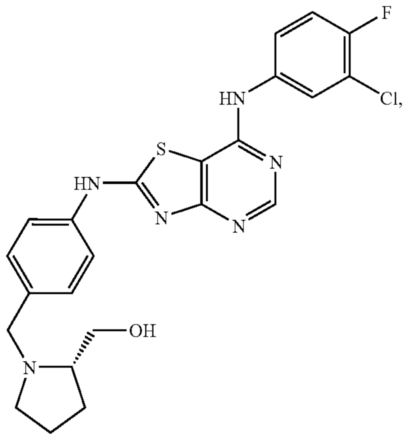
-continued
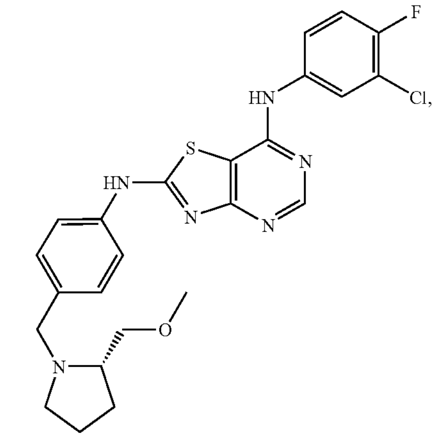
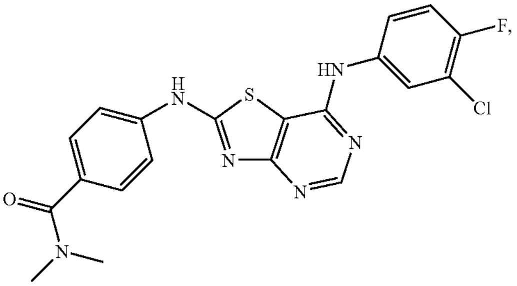
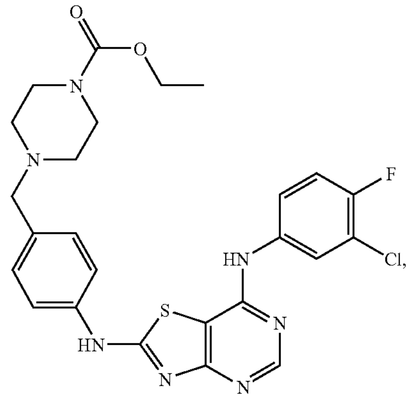
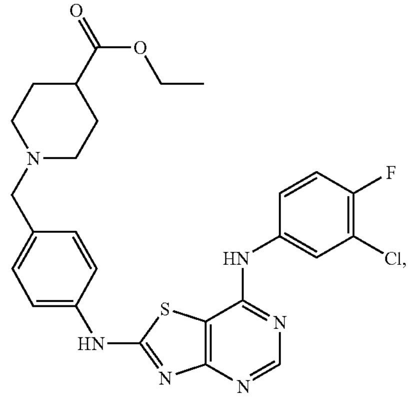

-continued
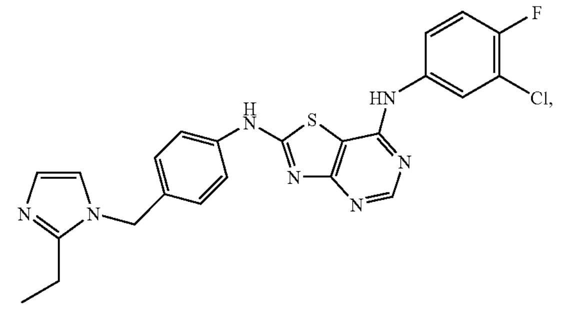
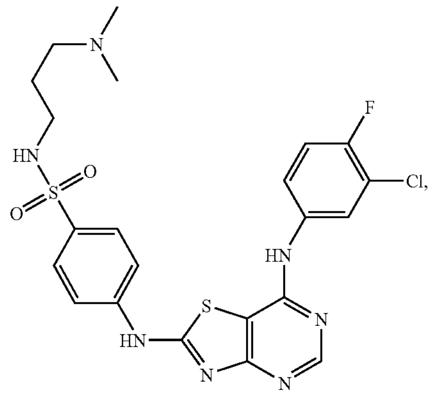
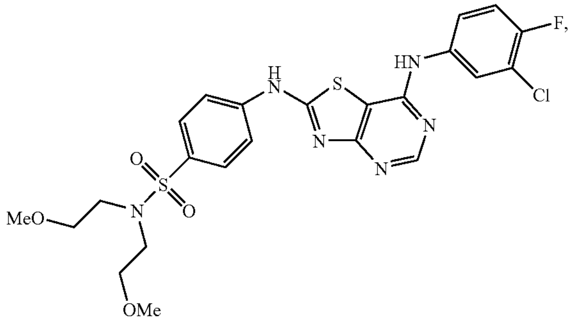
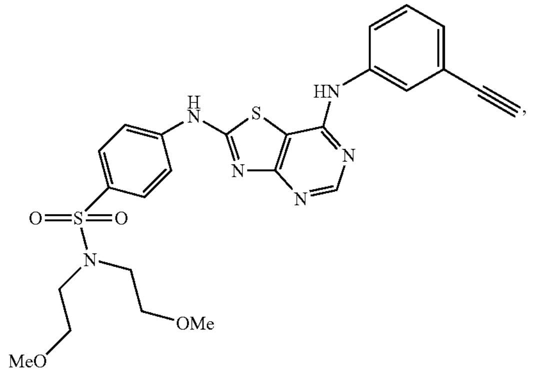
-continued
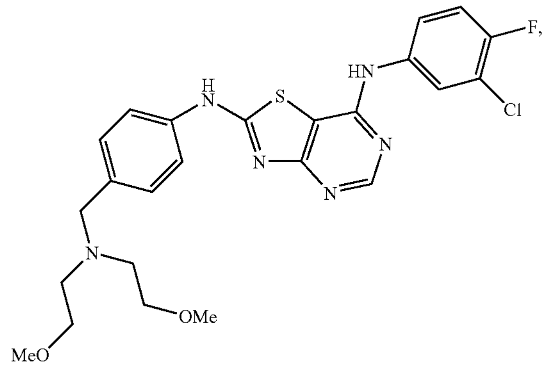
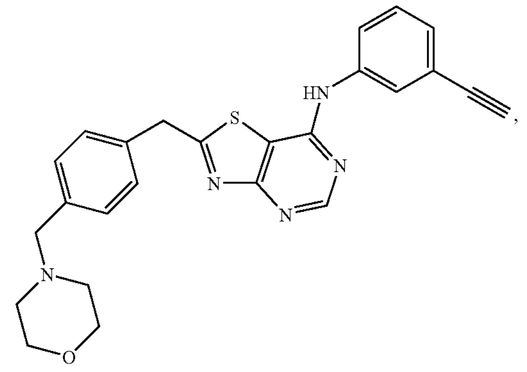
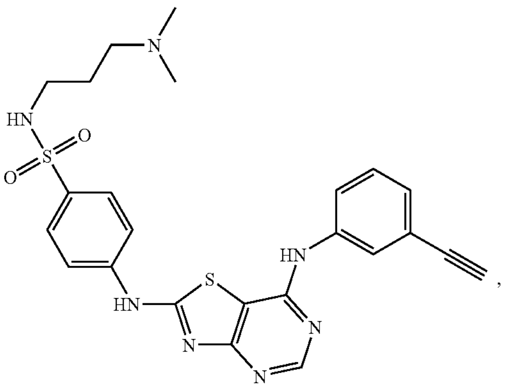
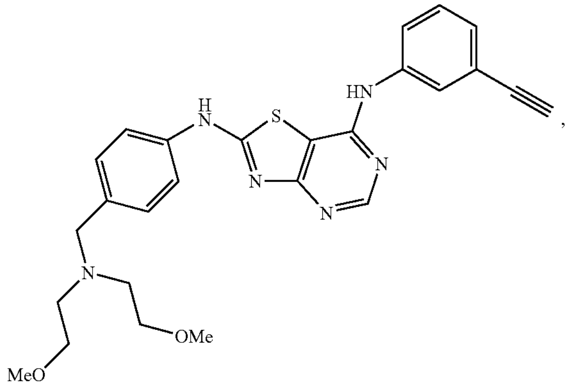

-continued
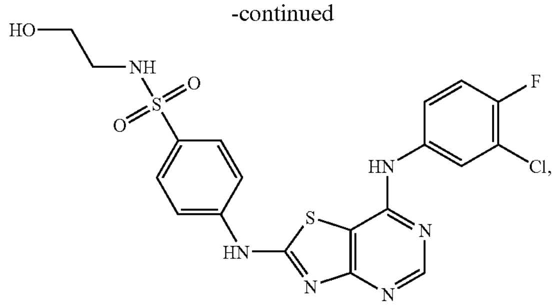
,
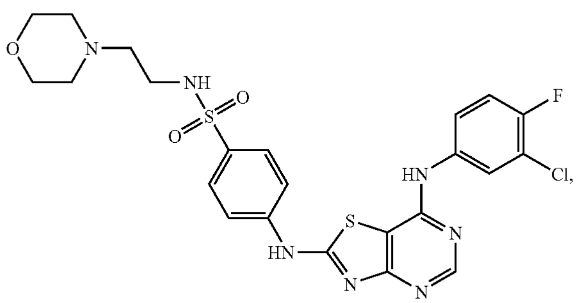
,
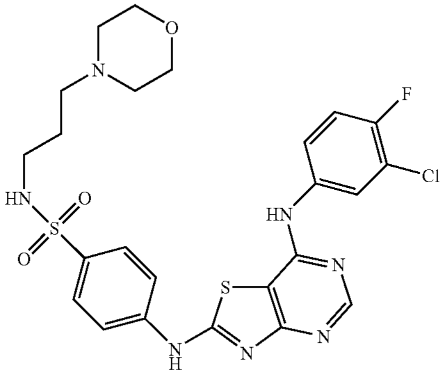
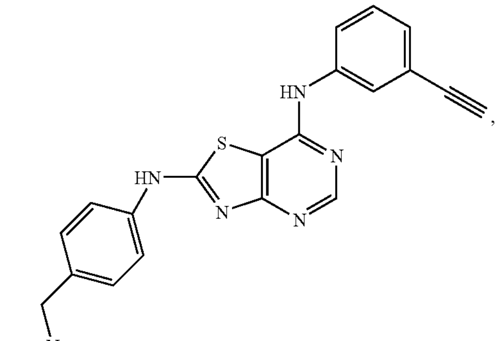
,
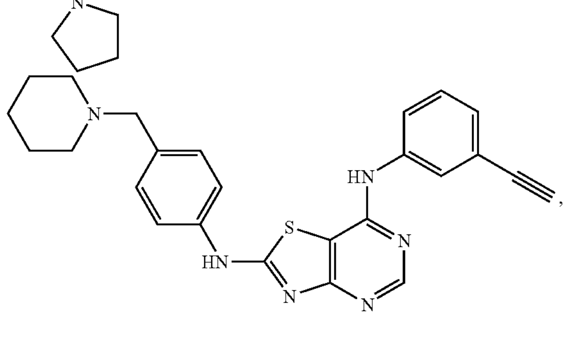
,
-continued
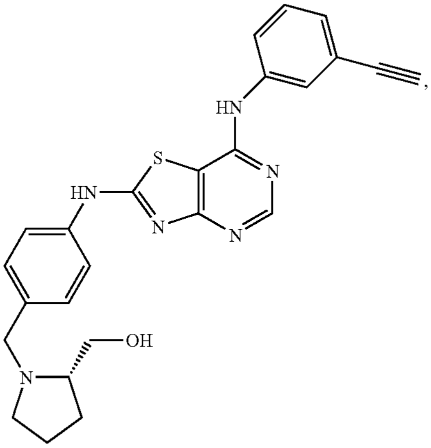
,
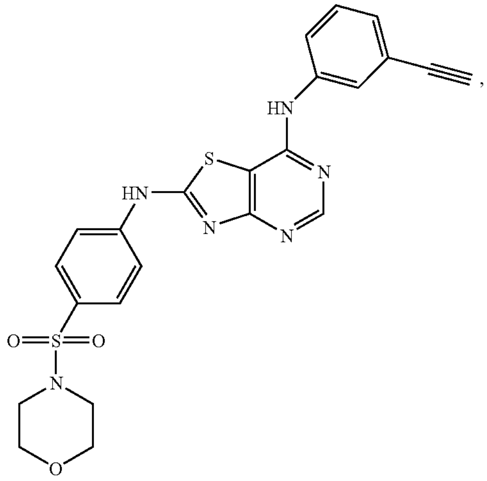
,
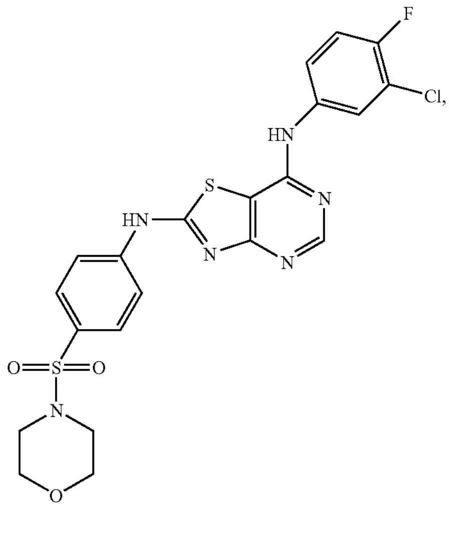
, -continued
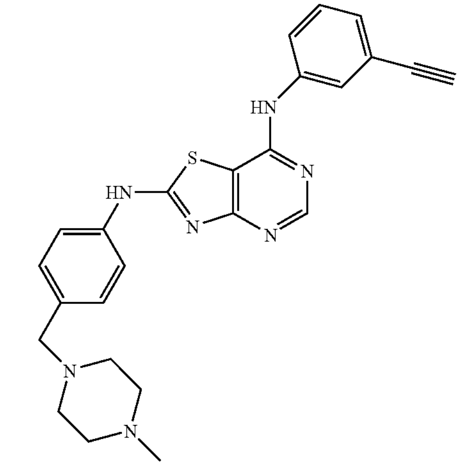
,
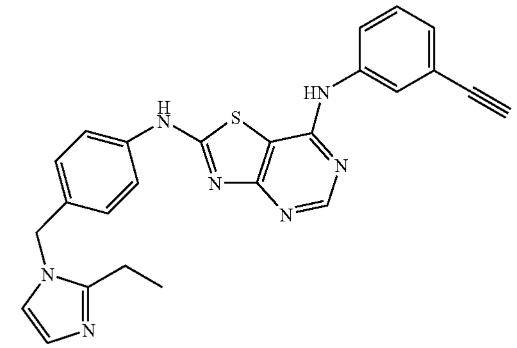
,
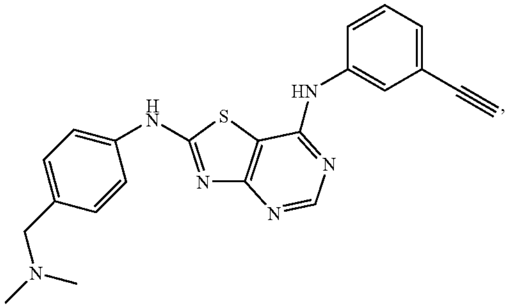
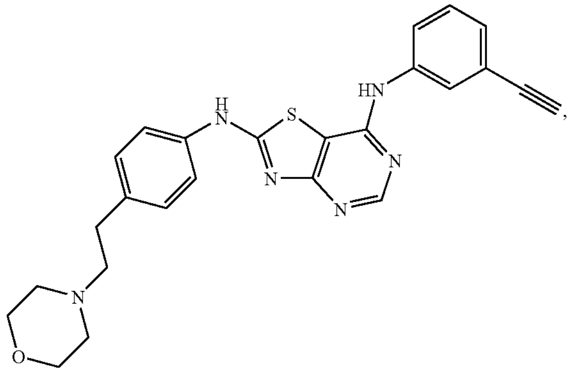
,
-continued
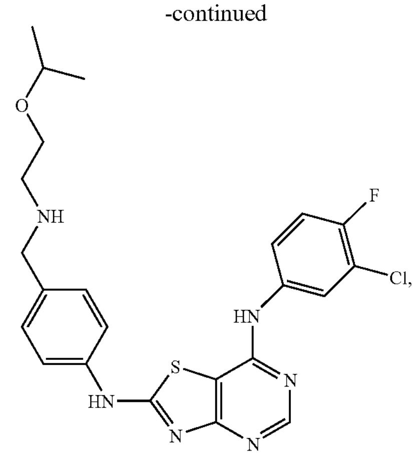
,
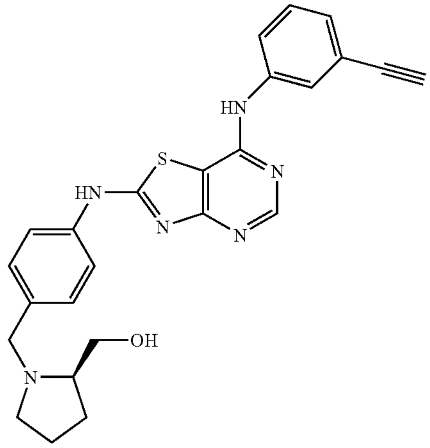
,
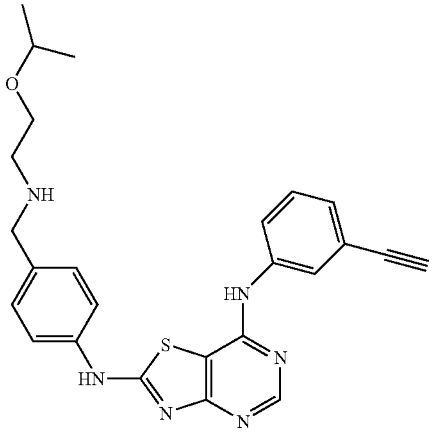
,
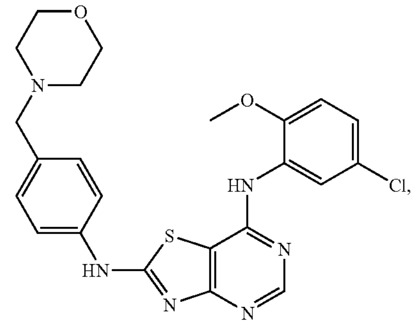
, -continued
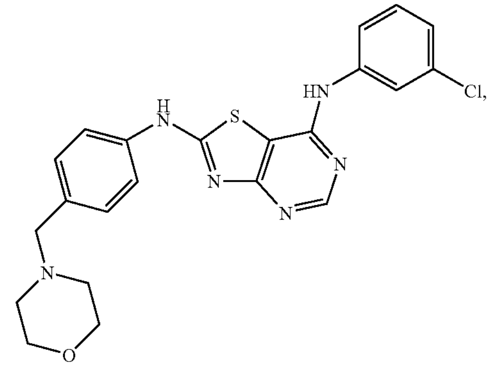
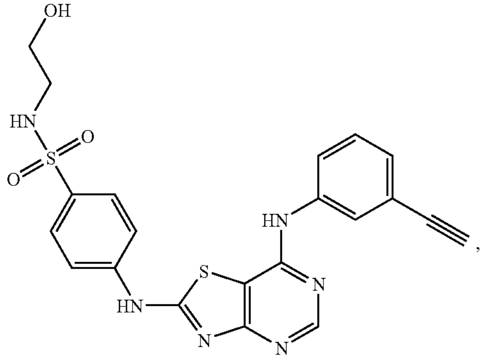
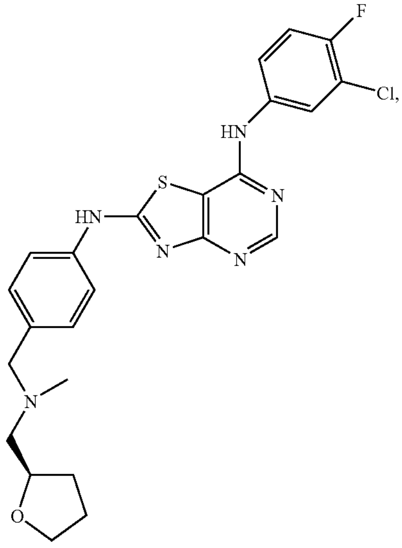
-continued
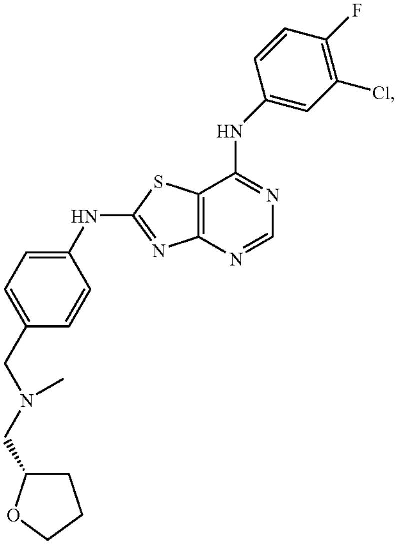
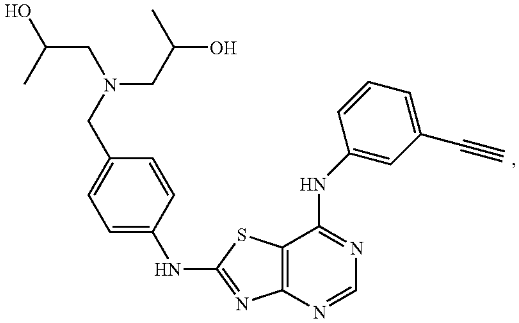
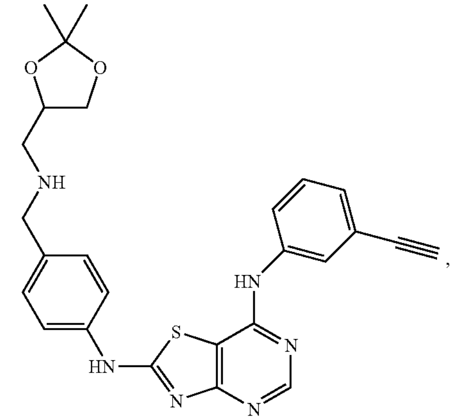
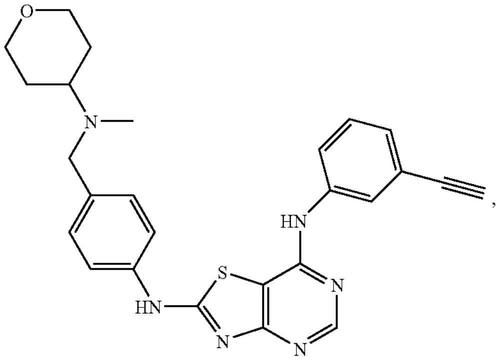

-continued
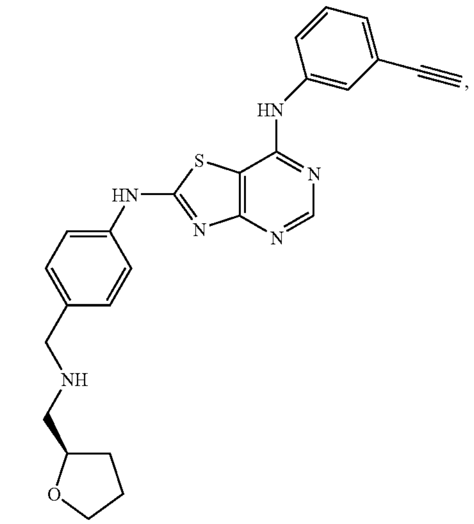
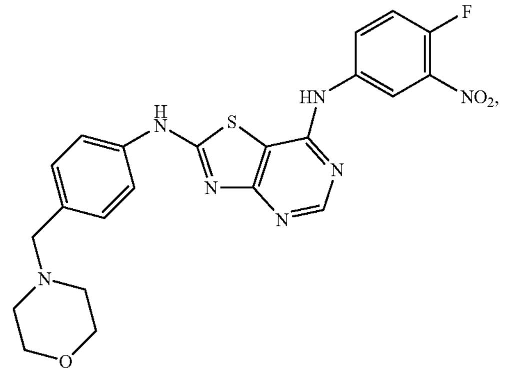
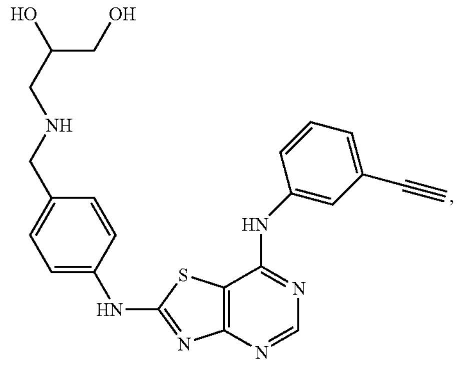
-continued
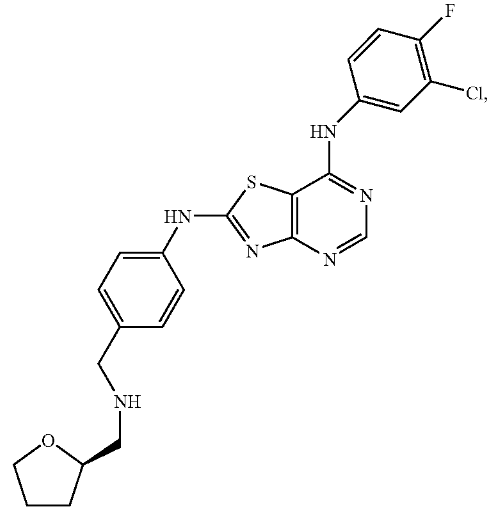
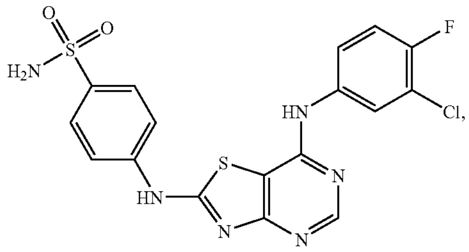
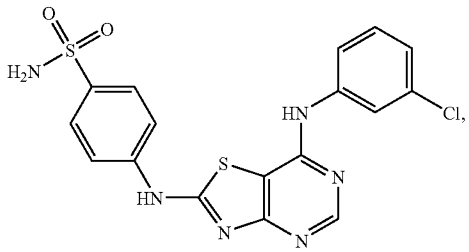
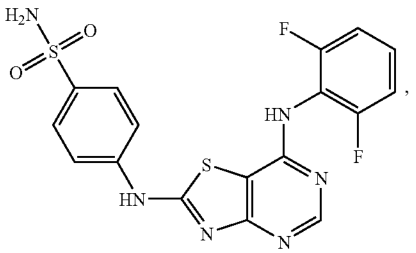
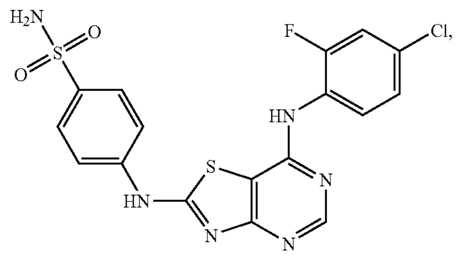

-continued
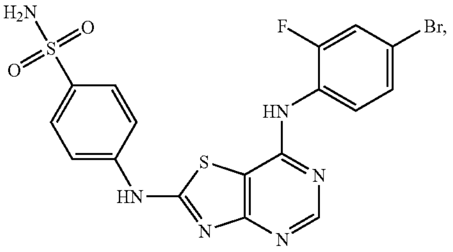
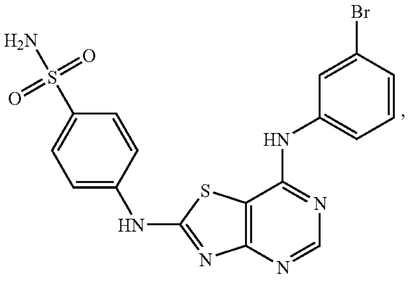
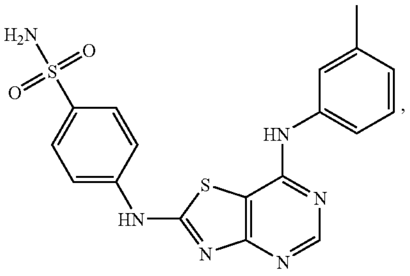
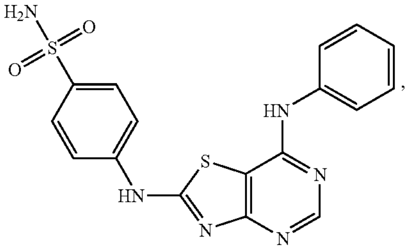
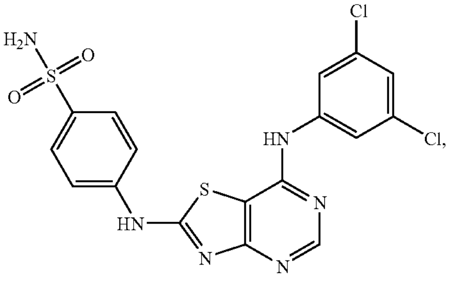
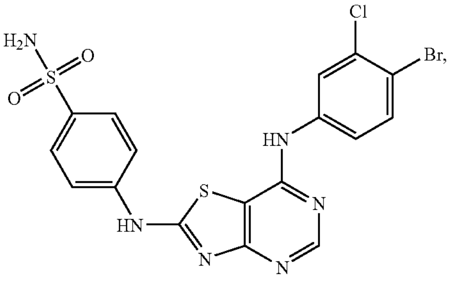
-continued
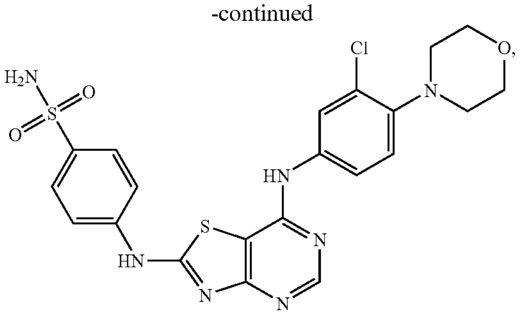
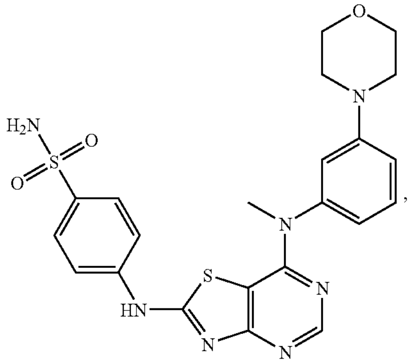
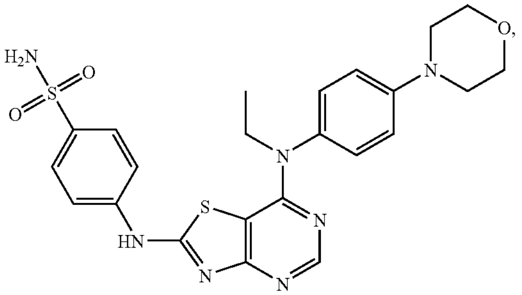
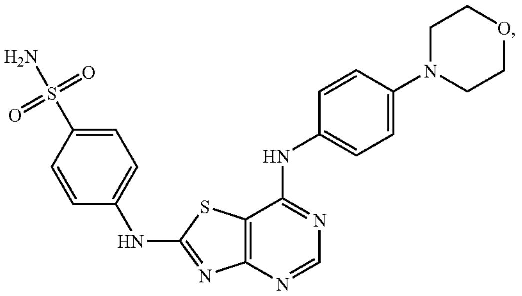
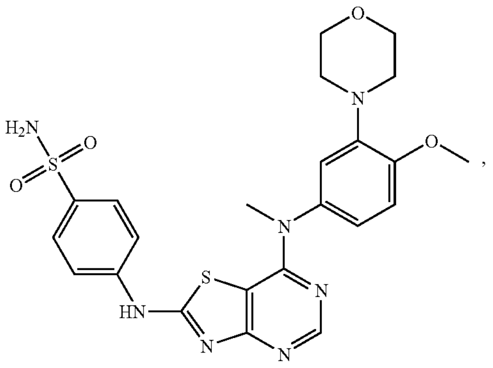

-continued
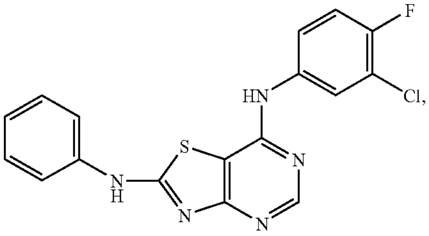
,
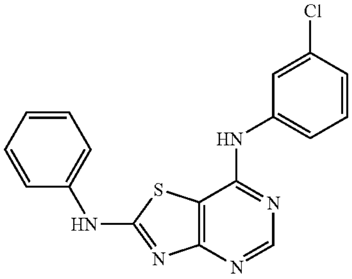
,
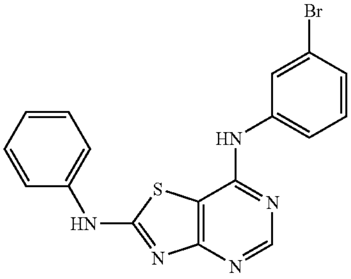
,
-continued
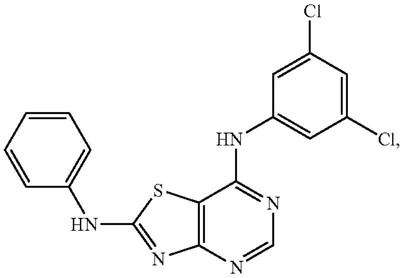
,
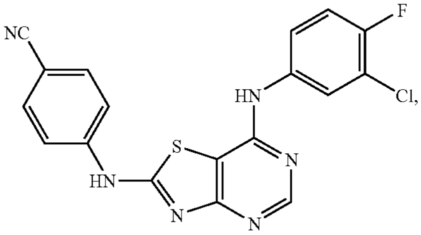
, and
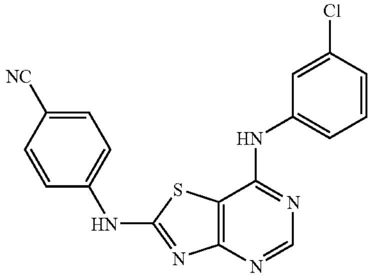
.
3. The compound of claim 1 in an isolated form.
4. A pharmaceutical composition comprising a pharmaceutically acceptable carrier and an effective amount of the compound of claim 1.
5. A process for preparing a pharmaceutical composition comprising the step of mixing the compound of claim 1 with a pharmaceutically acceptable carrier.
* * * * *

UNITED STATES PATENT AND TRADEMARK OFFICE

CERTIFICATE OF CORRECTION

PATENT NO. : 7,605,154 B2
APPLICATION NO. : 11/498221
DATED : October 20, 2009
INVENTOR(S) : Binnun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this

Fifth Day of October, 2010

David J. Kappos
*Director of the United States Patent and Trademark Office*